US007371862B2

(12) United States Patent
Vanotti et al.

(10) Patent No.: US 7,371,862 B2
(45) Date of Patent: May 13, 2008

(54) AZAINDOLYLIDENE DERIVATIVES AS KINASE INHIBITORS, PROCESS FOR THEIR PREPARATION AND PHARMACEUTICAL COMPOSITIONS COMPRISING THEM

(75) Inventors: Ermes Vanotti, Milan (IT); Francesco Angelucci, Milan (IT); Alberto Bargiotti, Milan (IT); Maria Gabriella Brasca, Cusago (MI) (IT); Antonella Ermoli, Buccinasco (MI) (IT); Maria Menichincheri, Milan (IT)

(73) Assignee: Pfizer Italia S.r.l., Rome (IT)

( * ) Notice: Subject to any disclaimer, the term of this patent is extended or adjusted under 35 U.S.C. 154(b) by 8 days.

(21) Appl. No.: 11/271,191

(22) Filed: Nov. 11, 2005

(65) Prior Publication Data

US 2007/0112020 A1 May 17, 2007

(51) Int. Cl.
*C07D 471/02* (2006.01)
*C07D 233/00* (2006.01)
(52) U.S. Cl. .................................. 546/113; 548/322.5
(58) Field of Classification Search ................ 546/113; 548/322.5
See application file for complete search history.

(56) References Cited

U.S. PATENT DOCUMENTS

2002/0022624 A1   2/2002   Dinnell et al.

FOREIGN PATENT DOCUMENTS

| GB | 2 298 198 A | 8/1996 |
|---|---|---|
| GB | 2 298 199 A | 8/1996 |
| WO | WO 94/14808 | 7/1994 |
| WO | WO 96/00226 | 1/1996 |
| WO | WO 97/49703 | 12/1997 |
| WO | WO 01/09121 A2 | 2/2001 |
| WO | WO 01/98299 A1 | 12/2001 |
| WO | WO 02/16348 A1 | 2/2002 |
| WO | WO 03/000688 A1 | 1/2003 |
| WO | WO 2006/040049 A1 | 4/2006 |

OTHER PUBLICATIONS

Cohen P., "The Development and Therapeutic Potential of Protein Kinase Inhibitors", *Current Opinion in Chemical Biology*, 3:459-465 (1999).
Hosoi T. et al., "Evidence for cdk5 as a Major Activity Phosphorylating Tau Protein in Porcine Brain Extract", *J. Biochem.*, 117(4):741-749 (1995).
Patani G.A. et al., "Bioisosterism: A Rational Approach in Drug Design", *Chem. Rev.*, 96:3147-3176 (1996).
Fleisher D. et al., "Improved Oral Drug Delivery: Solubility Limitations Overcome by the Use of Prodrugs", *Advanced Drug Delivery Reviews*, 19:115-130 (1996).
Robinson R.P. et al., "Discovery of the Hemifumarate and (α-L-Alanyloxy)Methyl Ether as Prodrugs of an Antirheumatic Oxindole: Prodrugs for the Enolic OH Group", *J. Med. Chem.*, 39:10-18 (1996).
Verbiscar A.J., "Sythesis of 1-p-Chlorobenzyl-7-Azaindole-3-α-Piperidylmethanol as a Potential Antimalarial Agent", *Journal of Medicinal Chemistry*, 15(2):149-152 (1972).
Gálvez C. et al., "Reactivity of 1H-Pyrrolo[2,3-b]Pyridine. I. Synthesis of 3-Acetyl-7-Azaindole and Related Compounds", *J. Heterocyclic Chem.*, 19:665-667 (1982).
Williams D.L. et al., "The Glyoxalines. V. The Bromination of 2-Phenyl-4-Benzal-5-Glyoxalidone", *J. Am. Chem. Soc.*, 68:647-649 (1946).
Khodair A.I. et al., "Synthesis, Conformational Analysis and Antitumor Testing of 5-(Z)-Arylidene-4-Imidazolidinone Derivatives", *Phosphorus, Sulfur and Silicon*, 140:159-181 (1998).

*Primary Examiner*—D. Margaret Seaman
*Assistant Examiner*—Nizal S. Chandrakumar
(74) *Attorney, Agent, or Firm*—Scully, Scott, Murphy & Presser, P.C.

(57) ABSTRACT

The present invention is directed to compounds of the formula

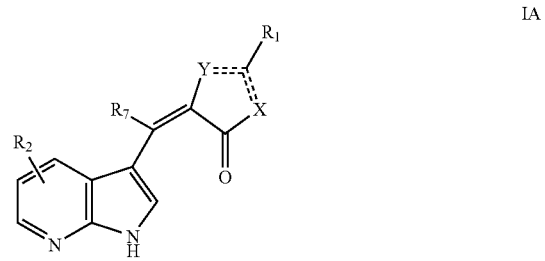

IA

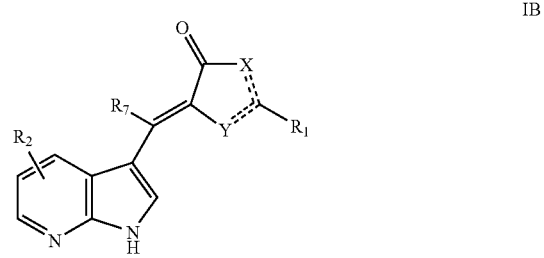

IB or pharmaceutically acceptable salts, prodrug, solvate or optical isomer thereof, pharmaceutical compositions containing same and use thereof for treating diseases linked to disregulated cell proliferation or to disregulated protein kinase.

27 Claims, No Drawings

AZAINDOLYLIDENE DERIVATIVES AS KINASE INHIBITORS, PROCESS FOR THEIR PREPARATION AND PHARMACEUTICAL COMPOSITIONS COMPRISING THEM

BACKGROUND OF THE INVENTION

1. Field of the Invention

The present invention relates to azaindolylidene derivatives active as kinase inhibitors and, more in particular, it relates to substituted azaindolylidene derivatives, a process for their preparation, pharmaceutical compositions comprising them and their use as therapeutic agents, particularly in the treatment of diseases linked to abnormal cell growth, such as cancer, in a mammal, including a human.

2. Discussion of the Background

The over-expression of protein kinases (PKs) is the hallmark of numerous diseases. A large share of oncogenes and proto-oncogenes are involved in human cancers code for PKs. The enhanced activities of PKs are also implicated in many non-malignant diseases such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or disregulation, See, for instance, *Current Opinion in Chemical Biology* 1999, 3, 459-465.

Several azaindoles and analogues thereof are known in the art, even as therapeutic agents.

As an example, azaindole derivatives possessing cell cycle dependent kinase activity have been described in WO01/98299 to Pevarello et al., vinylene-azaindole derivatives and azaindolylidene derivatives have been described for use as tyrosine kinase inhibitors, respectively in WO94/14808 and in WO96/00226 to Buzzetti et al., while antiangiogenic bicyclic derivatives are claimed by Hennequin et al. in WO02/16348.

Azaindoles as kinase inhibitors are also presented in WO03/000688 by P. Cox et al., and preparation of indoles and azaindoles as tachykinin antagonists is reported by Dinnell et al. in US2002/0022624, claiming activity against depression, anxiety, pain, inflammation.

Azaindole-Oxazolone derivatives and their use as anti- (*Helicobacter pylori*) agents are shown in PCT Int. Appl. WO 9749703 (Kanamaru et al.), preparation of azaidole-pyrazolinones as inhibitors of serine/threonine and tyrosine kinase activity is reported by Moset, M. et al. in PCT Int. Appl. WO 2001009121, the synthesis of azaindoles by Bishop, B. et al. in UK Pat. Appl. GB 2298199, while the use of new and known pyrrolo-pyridine derivatives as selective dopamine D4 receptor subtype antagonists—useful in treatment of psychotic disorders and alleviating symptoms of schizophrenia, without side-effects of classical neuroleptic drugs is described to Kulagowski, J. et al. in GB 2298198.

New 2-pyrazin-5-ones are serine/threonine and tyrosine kinase inhibitors, useful for treating e.g. cancer, hyperproliferative disorders, angiogenesis, inflammatory diseases and vascular hyperpermeability by Arnold, L. D. et al. in WO 2001009121.

SUMMARY OF THE INVENTION

The present invention relates to azaindolylidene derivatives which are multiple protein kinase inhibitors and are useful in the treatment of diseases caused by and/or associated with over expression of protein kinases and/or diseases driven by protein kinases activity.

An object of the present invention is to provide compounds which are useful as therapeutic agents against a host of diseases caused by over expression of protein kinase activity and/or diseases driven by protein kinases activity.

Another object of the present invention is to provide compounds, which are multiple protein kinase inhibitors.

Another object of the present invention is to provide compounds, which are useful for treating abnormal cell growth such as cancer.

More specifically, the azaindolylidene derivatives of the present invention are useful in the treatment of a variety of cancers, including, but not limited to: lung cancer, including small lung cancer, bone cancer, pancreatic cancer, skin cancer, including squamous cell carcinoma, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the liver, cancer of the gall bladder, hemoatopoietic tumors of lymphoid lineage, including leukemia, such as acute lymphocitic leukemia, or acute lymphoblastic leukemia, B-cell lymphoma, T-cell lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; lymphocytic lymphomas, cancer of the bladder, cancer of the kidney, renal cell carcinoma, carcinoma of the renal pelvis, primary CNS lymphoma, spinal axis tumors, brain stem glioma, pituitary adenoma, other tumors including melanoma, seminoma, teratocarcinoma, osteosarcoma, xenoderma pigamentosum, keratocanthoma, thyroid follicular cancer, Kaposi's sarcoma, or a combination of one or more of the foregoing cancers. In another embodiment, due to the key role of PKs in the regulation of cellular proliferation, these azaindolylidene derivatives an also useful in the treatment of cell proliferative disorders, including, but not limited to, psoriasis, benign prostate hyperplasia, vascular smooth cell proliferation associated with atherosclerosis, pulmonary fibrosis, arthritis glomerulonephritis, and post-surgical stenosis and restenosis.

The compounds of the present invention are also useful in the treatment of Alzheimer's disease, as suggested by the fact that cdk5 is involved in the phosphorylation of tau protein (*J. Biochem.*, 1995, 117, 741-749).

In addition, the compounds of the present invention are modulators of apoptosis, are useful in the treatment of cancer, as indicated hereinabove, viral infections, prevention of AIDS development in HIV-infected individuals, autoimmune diseases and neurodegenerative disorders.

The compounds of this invention are useful in inhibiting tumor angiogenesis and metastasis.

The compounds of this invention act as inhibitors of other protein kinases, e.g. protein kinase C in different isoforms, such as cdc7, her2, raf1, MEK1, MAPK, EGF-R, PDGF-R, FGF-R, IGF-R, PI-3K, wee1 kinase, Src, Abl, AKT, ILK, PAK, CDKs/Cyclins, Chk, Plk, Nek, bub1, aurora1, aurora2, GSK3, PKA, SULU1; and thus the compounds of the present invention are effective in the treatment of diseases associated with or caused by other protein kinases malfunctioning.

The present invention provides compounds of the following formulas hereinbelow:

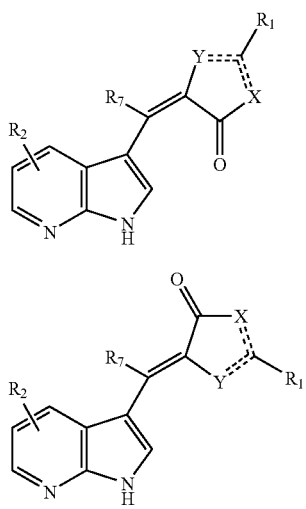

IA

IB or pharmaceutically acceptable salts, solvates or prodrugs thereof, wherein
$R_1$ is optionally substituted aryl, optionally substituted heteroaryl, $SR_5$, or $NR_3R_4$;
$R_3$ and $R_4$ are independently hydrogen, optionally substituted $C_1$-$C_8$ alkyl, optionally substituted $C_1$-$C_8$ hydroxyalkyl, optionally substituted $C_1$-$C_8$ alkoxy $C_1$-$C_8$ alkyl, optionally substituted $C_1$-$C_8$ alkylamino $C_1$-$C_8$ alkyl, optionally substituted $C_1$-$C_8$ dialkylamino $C_1$-$C_8$ alkyl, optionally substituted saturated or unsaturated $C_3$-$C_{12}$ cycloalkyl, optionally substituted saturated or unsaturated $C_3$-$C_{12}$ cycloalkyl $C_1$-$C_8$ alkyl, optionally substituted $C_2$-$C_8$ alkenyl, optionally substituted aryl, optionally substituted aryl $C_1$-$C_8$ alkyl, optionally substituted heterocyclyl, or optionally substituted heterocyclyl $C_1$-$C_8$ alkyl; or
$R_3$ and $R_4$ taken together with the nitrogen atom to which they are attached form a heterocyclic ring containing 1 ring nitrogen atom and up to 1 or 2 additional ring heteroatoms selected from oxygen, nitrogen and sulfur;
$R_5$ is optionally substituted $C_1$-$C_8$ alkyl, optionally substituted saturated or unsaturated $C_3$-$C_{12}$ cycloalkyl, optionally substituted saturated or unsaturated $C_3$-$C_{12}$ cycloalkyl $C_1$-$C_8$ alkyl, optionally substituted aryl, optionally substituted aryl $C_1$-$C_8$ alkyl, optionally substituted heterocyclyl, optionally substituted heterocyclyl $C_1$-$C_8$ alkyl, optionally substituted aryloxy $C_1$-$C_8$ alkyl, or optionally substituted $C_1$-$C_8$ alkyloxy $C_1$-$C_8$ alkyl;

$R_2$ is hydrogen, nitro, amino or —NH-Z-$R_6$;
Z is CO, $SO_2$, or $CH_2$;
$R_6$ is optionally substituted $C_1$-$C_8$ alkyl, optionally substituted aryl, optionally substituted aryl $C_1$-$C_8$ alkyl, optionally substituted heterocyclyl, optionally substituted heterocyclyl $C_1$-$C_8$ alkyl, optionally substituted $C_1$-$C_8$ hydroxyalkyl, optionally substituted $C_1$-$C_8$ alkoxy $C_1$-$C_8$ alkyl, optionally substituted $C_1$-$C_8$ dialkylamino $C_1$-$C_8$ alkyl, optionally substituted $C_1$-$C_8$ alkyl amino $C_1$-$C_8$ alkyl, optionally substituted $C_1$-$C_8$ alkylamino, optionally substituted $C_1$-$C_8$ dialkylamino, amino, optionally substituted $C_1$-$C_8$ alkyloxy, optionally substituted aryl $C_1$-$C_8$ alkyloxy, optionally substituted arylamino, optionally substituted aryloxy, optionally substituted aryl $C_1$-$C_8$ alkylamino;
$R_7$ is hydrogen or optionally substituted $C_1$-$C_8$ alkyl;
X is N, $NR_8$, O or S;
Y is N, $NR_9$, O or S; and the dotted lines between the carbon atom with the $R_1$ substituent and X or Y represent a single or double bond, provided that the carbon atom having the $R_1$ substituent does not have a double bond between X and Y simultaneously, where the alkyl, aryl, cycloalkyl or heterocyclic group, when used alone or in combination, are each independently optionally substituted with halogen, amino, mono $C_1$-$C_8$ alkyl amino, di $C_1$-$C_8$ alkyl amino, $C_1$-$C_8$ alkyl carbonyl amino, $C_1$-$C_8$ alkoxy, $C_1$-$C_8$ hydroxy $C_1$-$C_8$ alkyl, halo $C_1$-$C_8$ alkyl, hydroxy, heterocyclic, mercapto, thio $C_1$-$C_8$ alkyl, $C_1$-$C_8$ alkoxy, $C_1$-$C_8$ alkoxy $C_1$-$C_8$ alkyl, aryl, aryl $C_1$-$C_8$ alkyl, aryloxy, aryl $C_1$-$C_8$ alkoxy, heterocyclic $C_1$-$C_8$ alkyl, carbamoyl, $C_3$-$C_{12}$ saturated or unsaturated cycloalkyl, $C_3$-$C_{12}$ saturated or unsaturated cycloalkyl $C_1$-$C_8$ alkyl, $C_3$-$C_{12}$ saturated or unsaturated cycloalkoxy, heterocyclic carbonyl, aryl carbonyl, $C_1$-$C_8$ alkyl amino carbonyl $C_1$-$C_8$ alkyl, di $C_1$-$C_8$ alkyl amino carbonyl $C_1$-$C_8$ alkyl, $C_1$-$C_8$ alkyl amino carbonyl, di $C_1$-$C_8$ alkyl amino carbonyl, $C_1$-$C_8$ alkyl carbonyl or $C_2$-$C_8$ alkenyl; and
$R_8$ and $R_9$ are independently hydrogen or $C_1$-$C_8$ alkyl.

The compounds of Formulae IA and IB are used for treating diseases caused by and/or associated with an altered kinase activity in a mammal. Thus, an embodiment of the present invention is directed to a method of treating a disease in a mammal caused by or associated with an altered kinase activity which comprises administering to said mammal in need thereof an effective amount of the compound of Formula IA or IB depicted hereinabove.

It is to be noted that, as depicted, the structure IA is the 5E diastereomer, while IB represents the 5Z diastereomer. Both the 5E and 5Z diastereomers and/or mixtures thereof are contemplated to be within the scope of the present invention. Although both 5Z and 5E diastereomers exhibit the utilities described herein, the preferred diastereomer is the 5Z diastereomer. Since the 5E and 5Z diastereomer can be separated by techniques known to one of ordinary skill in the art, such as chromatography, e.g., column chromatography, it is preferred that if the 5Z isomer is utilized, then they are substantially free of the E isomer. For example, it is preferred that the 5Z diastereomers are comprised of less than about 25% E isomer and more preferably less than about 15% E isomer and even more preferably less than about 10% E isomer and most preferably less than about 5% E isomers and even most preferably less than about 1% E isomer. Also substantially pure 5E isomer can be utilized. If substantially pure 5E isomer is utilized, it is preferred that the 5E isomers are substantially free of the 5Z isomer. For example, it is preferred that the 5E diastereomers are comprised of less than about 25% 5Z isomer and more preferably less than about 15% Z isomer and even more preferable less than about 10% Z isomer and especially more preferably less than about 5% Z isomer and most preferably less than about 1% E isomer. Nevertheless, as indicated hereinabove, a mixture of 5Z and 5E isomers can be utilized in the present invention.

It is preferred that when Z is CO or $SO_2$, then $R_6$ is amino, optionally substituted $C_1$-$C_8$ alkylamino, optionally substituted $C_1$-$C_8$ dialkylamino, optionally substituted $C_1$-$C_8$ alkoxy, optionally substituted aryloxy, optionally substituted aryl $C_1$-$C_8$ alkoxy, optionally substituted arylamino or optionally substituted aryl $C_1$-$C_8$ alkylamino.

The compounds of Formula IA and IB are azaindoles having the following nucleus:

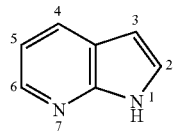

According to IUPAC nomenclature, also used in the present specification, the name is 1H-pyrrolo[2,3-b]pyridine.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or over expression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The term "treating", as used herein, unless otherwise indicated, means reversing, alleviating, inhibiting the progress of, or preventing the disorder or condition to which such term applies, or one or more symptoms of such disorder or condition.

The term "treatment", as used herein, unless otherwise indicated, refers to the act of treating as "treating" is defined immediately above.

The term "halo", as used herein, unless otherwise indicated, includes fluoro, chloro, bromo or iodo. Preferred halo groups are fluoro and chloro.

The term "alkyl", as used herein, alone or in combination, unless otherwise indicated, includes saturated monovalent hydrocarbon radicals having straight or branched moieties having the number of carbon atoms designated. Examples include methyl, ethyl, propyl, isopropyl, butyl, isobutyl, sec-butyl, tert-butyl, pentyl, isopentyl, neopentyl, hexyl and the like. The preferred alkyl contains 1-6 carbon atoms.

The term "hydroxyalkyl" when used alone or in combination, refers to an alkyl group, as defined herein substituted by at least one hydroxy group and preferably no more than 3 hydroxy group and more preferably only 1 hydroxy group. The hydroxy group may be substituted on any of the carbon atoms in the chain.

As used herein, the term "alkoxy" when used alone or in combination refers to an O-alkyl group, i.e., alkyl bonded to the main chain through an oxygen bridge. Examples include methoxy, ethoxy, propoxy, isopropyloxy, butoxy, isobutoxy, sec-butoxy, t-butoxy and the like.

"Alkoxyalkyl", when used alone or in combination, refers to an alkyl group, as defined herein, substituted by an alkoxy group, as defined herein. More specifically, it refers to an alkoxy group substituted to the main claim by an alkylene group.

An "alkylamino", in combination or alone, is an amino group ($NH_2$) in which one of the hydrogen atoms is replaced by an alkyl group as defined herein and in which the N atom is bonded to the main chain. Examples include methylamino, ethylamino, propylamino, isopropylamino, butylamino, t-butylamino and the like.

The term "dialkylamino" when used alone or in combination refers to an amino group ($NH_2$) in which both hydrogens atoms of the amino group is substituted by two alkyl groups. Examples include dimethylamino, ethylmethylamino, diethylamino, dipropylamino, methylpropylamino, and the like.

An "alkylaminoalkyl" group refers to an alkyl group which is substituted by an alkylamino, as defined herein. In other words, it refers to an aminoalkyl group attached to the main chain through an alkylene group.

A "cycloalkyl" group, when used alone or in combination, as defined herein, refers to a cyclic group containing only 3-12 ring carbon atoms. It may contain 1 ring, 2 rings, or 3 or more rings. The cycloalkyl group may be completely saturated or partially unsaturated, but it excludes completely aromatic compounds, i.e., aryl compounds. Examples include cyclopropyl, cyclopentyl, cyclohexyl, cyclohexen-1-yl, 1,3-cyclohexadienyl, adamantyl, 2,6,6-trimethylbicyclo[3.1.1]hept-3-yl, 1,7,7-trimethylbicyclo[2.2.1]hept-2-yl, bicyclo[2.2.1]hept-2-yl, and the like. As defined herein, the cycloalkyl group include benzo fused systems but it is to be understood that at least one of the rings is not aromatic. Thus, the term "cycloalkyl" also includes dihydronaphthyl, indanyl, indenyl, and the like.

"Cycloalkyl alkyl" is an alkyl group bonded to a cycloalkyl group, i.e., the alkyl group bridges the cycloalkyl group, as defined herein, to the main chain. Examples include cyclopentyl methyl, cyclohexyl ethyl, cyclohexylmethyl, cyclobutylethyl, cyclohexylisopropyl, cyclopen-1-tenylmethyl, cyclo1-2-hexenylmethyl, and the like.

The term "alkenyl", as used herein, unless otherwise indicated, is alkyl groups, as defined above, having at least one carbon-carbon double bond. Examples include vinyl, 1 or 2-propenyl, 1 or 2-butenyl, 1,2, or 3-pentenyl, 1-2-or 3-hexenyl, 1,2, -3- or 4-heptenyl, 1-, 2-, 3-, or 4-octenyl, and the like.

The term "alkynyl", as used herein, unless otherwise indicated, includes alkyl groups, as defined above, having at least one carbon-carbon triple bond. Examples include ethynyl, 1-propynyl, 1-butynyl and the like.

The term "aryl", as used herein, unless otherwise indicated, includes an organic radical derived from an aromatic hydrocarbon by removal of one hydrogen, such as phenyl or naphthyl. It contains 6-14 ring carbon atoms and preferably 6, 10 or 14 ring atoms. It may contain one ring, or two or three rings. Examples include phenyl, α-naphthyl, β-naphthyl and the like.

"Aralkyl" refers to an alkyl group bonded to an aryl group in which the alkyl group bridges the aryl group to the main chain. Examples include benzyl, phenethyl, phenylpropyl, α-naphthylethyl, β-naphthylmethyl and the like.

The term "heterocyclic", as used herein, unless otherwise indicated, includes non-aromatic and aromatic heterocyclic groups containing one or more ring heteroatoms, each selected from O, S and N, wherein each heterocyclic group has from 3 to 18 ring atoms in its ring system, but more preferably 3 to 10 ring atoms. The heterocyclic group may be monocyclic or bicyclic. It may be completely saturated, partially unsaturated or fully heteroaromatic. As defined herein, the term heterocyclic includes the heteroaromatic group. It is preferred that the heterocyclic group contains at most 4 ring heteroatoms and most preferably 1 or 2 ring heteroatoms: It is preferred that at least one of the ring heteroatoms is nitrogen. The heterocyclic groups include benzo-fused ring systems and ring systems substituted with one or more oxo moieties. An example of a 4 membered heterocyclic group is azetidinyl (derived from azetidine). An example of a 5 membered heterocyclic group is pyrrolidine. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiopanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo [3.1.0]hexanyl, 3-azabicyclo[4.1.0]heptanyl, 3H-indolyl and quinolizinyl, and the like. Preferred non-aromatic heterocyclic groups include pyrrolidine, pyrroline, imidazolidine, tetrahydrofuran, imidazoline, piperidine, piperazine, morpholine, tetrahydropyran, tetrahydrothiopyran, 1-azabicyclo [2.2.2] oct-3-yl, 8-methyl-8-azabicyclo [3.3.1]oct-3-yl and the like.

However, as defined herein, the term "heterocyclic" includes heteroaryl. As defined herein, the term "heteroaryl" refers to a heteroaromatic group containing 5 to 18 ring atoms and more preferably 5 to 10 ring atoms, and 1, 2 or 3 ring heteroatoms selected from the group consisting of oxygen, sulfur or nitrogen and the remaining ring atoms are carbon atoms. The heteroaryl group may contain 1, 2 or 3 heteroring atoms, and more preferably 1 or 2 ring heteroring atoms. It may be monocyclic, bicyclic, tricyclic or tetracyclic. It is preferred that one of the ring heteroatoms is a nitrogen atom. The heteroaryl group also includes benzofused rings, but the ring to which the benzo group is fused must be a heteroaryl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl, and the like.

Both the heterocyclic and the heteroaryl groups may be C-attached or N-attached where such is possible. For instance, a group derived from pyrrole may be pyrrol-1-yl (N-attached) or pyrrol-3-yl (C-attached).

The term "heterocyclic alkyl" refers to an alkyl group bonded to a heterocyclic group, as defined herein i.e., an alkyl group bridging the heterocyclic group to the main chain. Examples include piperazinemethyl, morpholinoethyl, pyrrolidinylmethyl, indolyinylethyl and the like.

"Heteroaromatic alkyl" or "heteroaryl alkyl" as used herein refers to an alkyl group bonded to a heteroaryl group, i.e., an alkyl group bridges the heteroaromatic group to the main chain. Examples include pyridinyl methyl, pyrrolethyl, quinolylmethyl, furylmethyl, thienylethyl, and the like.

The term "aryloxy" refers to an O-aryl bond as defined herein, i.e., an oxygen atom bridging an aryl group, as defined herein, to the main chain.

The term "arylalkoxy" refers to an alkoxy group bridging an aryl group, as defined herein to the main chain. Examples include benzyloxy, phenethoxy, phenylpropoxy, and the like.

"Heterocyclicoxy" as used herein refers to an oxygen atom bonded to the heterocyclic group, as defined herein, i.e., a O-heterocyclic group bonded to the main chain through the oxygen atom. Examples include quinolyloxy, piperidyloxy and the like.

"Heterocyclic alkoxy" refers to an alkoxy group bridging the heterocyclic group to the main chain. Examples include morpholinyl methoxy, pyridylethoxy and the like.

"Heteroaryloxy" refers to an oxygen atom bridging the heteroaryl group, as defined herein to the main chain. "Heteroaryl alkoxy" refers to an alkoxy group, as defined herein, bridging the heteroaryl group to the main chain.

Carbalkoxy when used alone or in combination refers to an acyl group (CO) bonded to an alkoxy group, as defined herein.

An "alkanoyl group" refers to an alkyl group in which at least one of the carbon atoms in the "alkyl" chain is replaced by a carbonyl group (CO). It is preferred, however, that only one of the carbon atoms is replaced by (CO). It is also preferred that the first carbon atom in the chain is replaced by (CO), i.e., an alkylcarbonyl. Examples include 1-propanoyl, 2-butanoyl, 3-pentanoyl, 3,3-dimethyl-2-butanoyl, and the like.

The term "optionally substituted", as used herein relating to alkyl, alkenyl, cycloalkyl, aryl, heteroaryl or heterocyclic alone or in combination refers to the optional substituents on each of the aforementioned moieties. If the term "optionally substituted" precedes one of the aforementioned moieties or a combination of one or more of the aforementioned moieties, the optional substituent may be present on either one of the moieties or on both. For example, when optionally substituted is used before arylalkyl, it signifies that both the aryl and alkyl group may be optionally substituted. The same is true for the other groups listed hereinabove in combination. As used herein, the optional substituents are as defined hereinabove. The preferred optional substituents are halogen, amino, alkylcarbonyl amino (e.g., acetylamino), hydroxy, $(C_1-C_8)$ alkyl, halo $(C_1-C_8)$alkyl, (e.g., fluoro $C_1-C_8$ alkyl, trifluoromethyl), hydroxy $(C_1-C_8)$alkyl, $(C_1-C_8)$ alkoxy, $(C_1-C_8)$ alkoxy $(C_1-C_8)$alkyl, aryl (e.g., phenyl, naphthyl, and the like), aryl $(C_1-C_8)$alkyl, (e.g., benzyl, phenethyl, and the like), heterocyclic, as defined herein, carbamoyl, heterocyclic carbonyl, $C_3-C_{12}$ saturated or unsaturated cycloalkyl, $C_3-C_{12}$ saturated or unsaturated cycloalkyl $C_1-C_8$ alkyl, $C_1-C_8$ alkyl amino carbonyl $C_1-C_8$ alkyl, di $C_1-C_8$ alkyl amino carbonyl $C_1-C_8$ alkyl, or di $C_1-C_8$ alkyl amino carbonyl or $C_2-C_8$ alkenyl.

As defined herein, $R_1$ is a substituent on the diazole moiety of the compounds of Formula IA or IB. It is preferred to be an optionally substituted aryl or optionally substituted heteroaryl or $NR_3R_4$, wherein aryl and heterocyclic are as defined herein.

Preferred values of $R_3$ and $R_4$ are independently hydrogen, saturated or unsaturated $C_3-C_{12}$ cycloalkyl, saturated or unsaturated $C_3-C_{12}$ cycloalkyl $C_1-C_8$ alkyl, aryl, aryl $C_1-C_8$ alkyl, heterocyclic, heterocyclic $C_1-C_8$ alkyl and $C_1-C_8$ alkyl or $R_3$ and $R_4$ taken together with the nitrogen atom to which they are attached form a heterocyclic ring. It is preferred that $NR_3R_4$ is $NHR_3$, with $R_3$ as defined herein.

It is even more preferred that $R_1$ is phenyl, heteroaryl or $NR_3R_4$ wherein $R_3$ and $R_4$ are as defined herein. It is especially preferred that $R_1$ is optionally substituted phenyl or optionally substituted heteroaryl, containing 1 or 2 ring heteroatoms, wherein at least one of the ring heteroatoms is nitrogen. In another embodiment, $R_1$ is $NR_3R_4$ wherein $R_3$ and $R_4$ taken together with the nitrogen atom to which they are attached form a heterocyclic group, as defined herein, containing a nitrogen ring heteroatom and 0 or 1 additional ring heteroatoms selected from oxygen, nitrogen and sulfur.

It is preferred that $R_2$ is on position 5 of the azaindole ring. The preferred substituent for $R_2$ is hydrogen or $NHZR_6$ wherein Z and $R_6$ are as defined herein. It is more preferred that $R_2$ is hydrogen or $NHC(O)R_6$, where $R_6$ is optionally substituted alkyl, an optionally substituted heterocyclic, optionally substituted heterocyclic lower alkyl, optionally substituted aryl, or optionally substituted aryl lower alkyl. It is most preferred that $R_2$ is hydrogen.

In another embodiment, $R_1$ is optionally substituted aryl and $R_2$ is hydrogen, —$NHZR_6$, Z is —C(O)—, and $R_6$ is optionally substituted heterocyclic or optionally substituted heterocyclic $C_1$-$C_8$ alkyl, optionally substituted $C_1$-$C_8$ alkyl, optionally substituted aryl, optionally substituted heterocyclic, or optionally substituted di ($C_1$-$C_8$)alkyl amino $C_1$-$C_8$ alkyl. In still another embodiment, $R_1$ is an optionally substituted phenyl, optionally substituted 5 or 6 membered heteroaryl group having 1 or 2 ring heteroatoms selected from nitrogen, oxygen or sulfur or $NR_3R_4$ wherein $R_3$ and $R_4$ taken together with the nitrogen atom to which they are attached form a 4-8 membered heterocyclic group having a nitrogen ring heteroatom and 0 or 1 additional ring heteroatoms selected from the group consisting of nitrogen, oxygen or sulfur. It is preferred that wherein $R_2$ is hydrogen.

Furthermore, it is preferred that $R_1$ is —$NHR_3$, wherein $R_3$ is optionally substituted phenyl or optionally substituted heterocyclic ring containing 1 or 2 ring heteroatoms, wherein at least one ring heteroatom is nitrogen and $R_2$ is hydrogen.

It is preferred that $R_7$ is $CH_3$ and more especially hydrogen.

The ring containing X and Y either has no double bonds between the carbon bearing the $R_1$ substituent and X or Y or 1 double bond therebetween. The carbon bearing the $R_1$ substituent cannot be double bonded between Y and X at the same time. X can be either N, $NR_8$, S or O, and Y can be N, $NR_9$, O or S, wherein $R_8$ and $R_9$ are independently H or $C_1$-$C_8$ alkyl. But if X is $NR_8$, O or S, then it is single bonded; and if Y is O, S or $NR_9$, it is single bonded. If X is N, then the bond between X and the carbon atom bearing the $R_1$ substituted is a double bond and Y is single bonded (and Y≠N). On the other bond, with Y is N, then there is a double bond between the carbon atom bearing the $R_1$ substituent and Y, and there is a single bond between the carbon atom bearing the $R_1$ substituent and X (and X≠N). The preferred value of $R_8$ and $R_9$ are independently H or $CH_3$.

The preferred X is N, $NR_8$, or O, and the preferred Y is S, N, or $NR_9$, wherein $R_8$ and $R_9$ are independently hydrogen or lower alkyl, especially methyl. For example, when X is NH or N and Y is N, NH or NMe or S, the heterocyclic ring containing Y and X becomes, e.g.,

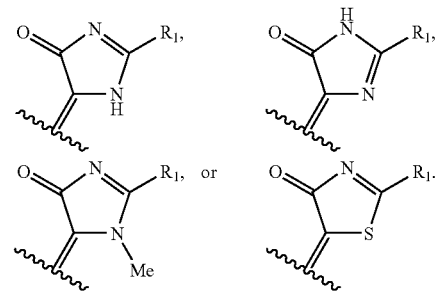

All of these embodiments are contemplated to be within the scope of the present invention.

other preferred embodiments of the present invention include compounds of the formulae:

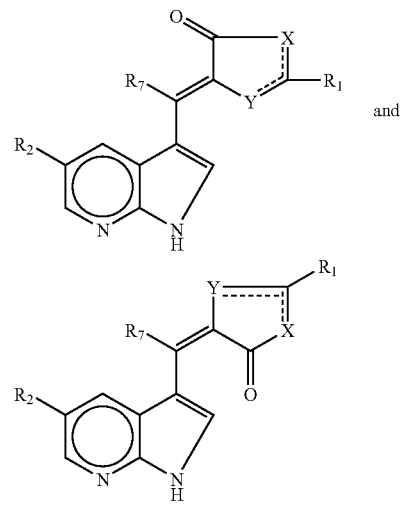

wherein $R_2$, $R_1$, $R_7$ and Y and X are as defined above.

It is more preferred that the compounds of the present invention have the formula,

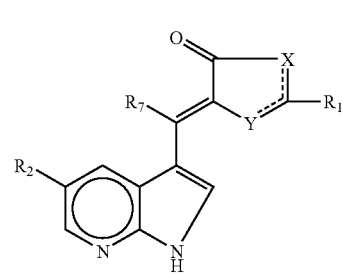

IC i.e., a compound of Formula IC, wherein $R_2$ is on the 5-position of the azaindole.

Preferred compounds are those of formula (IC) wherein $R_1$ is an optionally substituted aryl or an optionally substituted heteroaryl, or $R_1$ is a group —$NR_3R_4$ where one of $R_3$ and $R_4$ is hydrogen and the other is an optionally substituted saturated or unsaturated $C_3$-$C_{12}$ cyclo-alkyl, an optionally substituted saturated or unsaturated $C_3$-$C_{12}$ cycloalkyl $C_1$-$C_8$ alkyl, optionally substituted aryl $C_1$-$C_8$ alkyl group, an optionally substituted heterocyclyl group, or an optionally substituted heterocyclyl $C_1$-$C_8$ alkyl group, and $R_2$ is —NH-Z-$R_6$ where Z is CO and $R_6$ is an optionally substituted $C_1$-$C_8$ alkyl, an optionally substituted aryl or an optionally substituted heterocyclic especially heteroaryl, or optionally substituted $C_1$-$C_8$ dialkylamino $C_1$-$C_8$ alkyl group;

$R_7$ is H, X is NH or N and Y is N, NH or S.

In a preferred embodiment, of Formula IC, $R_1$ is $NHR_3$, wherein $R_3$ is benzyl, cyclohexyl, piperidinylbenzyl, methylbenzyl, $C_1$-$C_6$ alkyl, furylmethyl, thienylmethyl, bicyclo [2.2.2] octyl, where $R_3$ is unsubstituted or substituted with $C_1$-$C_6$ alkyl, or hydroxyl and $R_2$ is H.

In another preferred embodiment of Formula IC, $R_1$ is $NR_3R_4$ and $R_3$ and $R_4$ taken together with the nitrogen atom form a nitrogen containing heterocyclic ring. It is preferred that the heterocyclic ring is completely saturated or heteroaromatic. Moreover, it is preferred that the heterocyclic ring is a 5 or 6 membered heterocyclic ring containing 1 nitrogen ring atom and 1 or 2 additional ring nitrogen atoms, selected from nitrogen, oxygen or sulfur with the remaining ring atoms being carbon atoms. It is even more preferred that the ring heteroatoms are nitrogen or oxygen. The preferred heterocyclic rings formed are morpholinyl, piperazinyl, piperidinyl, pyrrolidino, azapanyl, diazapanyl, imidazolyl, azetidinyl and dihydropyrrolyl. The preferred heterocyclic groups formed from $NR_3R_4$ are pyridyl, pyrrolidinyl, piperazinyl, piperidinyl and morpholinyl. In this preferred embodiment, this heterocyclic group is unsubstituted or substituted with hydroxyalkyl or alkyl, as defined herein especially $C_1$-$C_6$ alkyl or $C_1$-$C_6$ hydroxyalkyl.

In another preferred embodiment of Formula IC, $R_1$ is aryl, arylalkyl, heteroaryl, heteroarylalkyl or alkyl which $R_1$ is unsubstituted or substituted with alkyl or hydroxyalkyl, as defined herein. The preferred aryl group is phenyl and the preferred alkyl groups are $C_1$-$C_6$ alkyl and the preferred heteroaryl are furyl or pyridyl. In this embodiment the preferred $R_1$ groups are phenyl, benzyl, furylmethyl, which $R_1$ group are either unsubstituted or substituted with hydroxyalkyl, as defined herein.

Other embodiments of the present invention are compounds of Formula IA or IB, wherein $R_1$ is NHAD wherein A is $(CHR_{10})_m$—$(CH_2)_n$, n is 0-5, m is 0-5, $R_{10}$ is $C_1$-$C_8$ alkyl, or aryl $C_1$-$C_8$ alkyl, and D is optionally substituted alkyl, optionally substituted cycloalkyl, optionally substituted aryl or optionally substituted heterocyclic wherein the optional substituents on alkyl, cycloalkyl, aryl, or heterocyclic are halogen, hydroxyl, $C_1$-$C_8$ alkyl, amino, $C_1$-$C_8$ alkyl amino, di $C_1$-$C_8$ alkyl amino, $C_1$-$C_8$ alkoxy, halo $C_1$-$C_8$ alkyl, aryloxy, aryl $C_1$-$C_8$ alkoxy, cycloalkyl, heterocyclic, haloaryl, halocycloalkyl, $C_1$-$C_8$ alkylaryl, $C_1$-$C_8$ alkylcycloalkyl, haloheterocyclic $C_1$-$C_8$ alkyl. It is to be noted that when n and m are both 0, A is a chemical bond. In this embodiment, D is preferably optionally substituted phenyl, optionally substituted cycloalkyl selected from the group consisting of cyclohexyl, cycloheptyl, dihydronaphthyl, bicyclo[2.2.1]heptyl 1,7,7-trimethyl bicyclo [2.2.1]heptyl, indanyl, dihydroindanyl, dihydronaphthyl, tetrahydronaphthyl, indenyl and adamantyl or optionally substituted heterocyclic selected from the group consisting of furyl, thienyl, piperidinyl, morpholinyl, tetrahydrofuryl, azabicyclo [2.2.2.]octyl, azabicyclo [3.2.1]octyl, benzothienyl or piperazinyl optionally substituted $C_1$-$C_8$ alkoxy.

Another embodiment of the present invention is directed to compounds of Formula IA or IB wherein $R_1$ is optionally substituted aryl or optionally substituted heteroaryl wherein aryl is phenyl and heteroaryl is furyl or pyridyl.

It is more preferred that the compounds of the present invention are the preferred embodiments of Formula IB depicted hereinbelow:

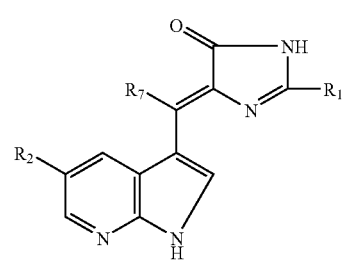

ID

The preferred compounds are those of of formula (ID) wherein $R_1$ is an optionally substituted aryl or an optionally substituted heteroaryl, or $R_1$ is a group —$NR_3R_4$, where $R_3$ and $R_4$ taken together with the nitrogen atom form an optionally substituted heterocyclyl group or where one of $R_3$ and $R_4$ is hydrogen and the other is an optionally substituted saturated or unsaturated $C_3$-$C_{12}$ cycloalkyl, an optionally substituted saturated or unsaturated $C_3$-$C_{12}$ cycloalkyl $C_1$-$C_8$ alkyl, an optionally substituted aryl, an optionally subsituted aryl $C_1$-$C_8$ alkyl group, or an optionally substituted heterocyclyl group, or an optionally substituted heterocyclic $C_1$-$C_8$ alkyl, and $R_2$ and $R_7$ are hydrogen atoms.

It is especially preferred that the compounds of the present invention have the formula

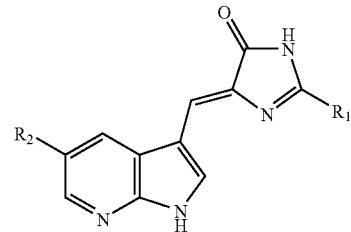

or pharmaceutically acceptable salts, prodrug, or solvate thereof wherein $R_1$ is —$NR_3R_4$ and $R_2$ is H, and $R_3$ and $R_4$ taken together form a heterocyclic ring, as defined herein.

In another embodiment, the compounds of the present invention have the formula

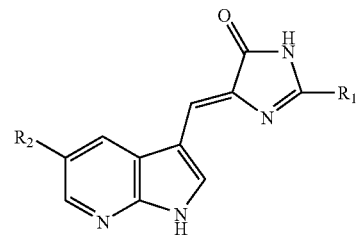

or pharmaceutically acceptable salt, prodrug or solvate, wherein $R_1$ is —$NHR_3$ and $R_2$ is H, and $R_3$ is as defined hereinabove.

In another embodiment the preferred compounds have the formula depicted hereinabove.

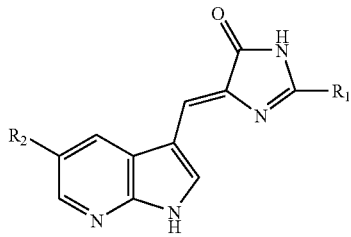

where R$_2$ is H and R$_1$ is optionally substituted aryl or optionally substituted heteroaryl.

The preferred compounds of the present invention are
(5E)-2-phenyl-5-(1H-pyrrolo[2,3-b]pyridin-3-ylmethylene)-3,5-dihydro-4H-imidazol-4-one;
(5Z)-2-phenyl-5-(1H-pyrrolo[2,3-b]pyridin-3-ylmethylene)-3,5-dihydro-4H-imidazol-4-one;
(5Z)-2-(3-methylphenyl)-5-(1H-pyrrolo[2,3-b]pyridin-3-ylmethylene)-3,5-dihydro-4H-imidazol-4-one;
(5Z)-2-(4-methylphenyl)-5-(1H-pyrrolo[2,3-b]pyridin-3-ylmethylene)-3,5-dihydro-4H-imidazol-4-one;
(5Z)-2-(4-bromophenyl)-5-(1H-pyrrolo[2,3-b]pyridin-3-ylmethylene)-3,5-dihydro-4H-imidazol-4-one;
(5Z)-2-(4-fluorophenyl)-5-(1H-pyrrolo[2,3-b]pyridin-3-ylmethylene)-3,5-dihydro-4H-imidazol-4-one hydrochloride;
(5E)-2-(4-acetylaminophenyl)5-(1H-pyrrolo[2,3-b]pyridin-3-ylmethylene-(2-benzylamino)-3,5-dihydro-4-H-imidazol-4-one;
(5Z)-2-(4-acetylaminophenyl)5-(1H-pyrrolo[2,3-b]pyridin-3-ylmethylene-(2-benzylamino)-3,5-dihydro-4-H-imidazol-4-one;
(5Z)-2-[4-(hydroxymethyl)phenyl]-5-(1H-pyrrolo[2,3-b]pyridin-3-ylmethylene)-3,5-dihydro-4H-imidazol-4-one;
(5Z)-2-pyridin-3-yl-5-(1H-pyrrolo[2,3-b]pyridin-3-ylmethylene)-3,5-dihydro-4H-imidazol-4-one;
(5Z)-2-(2-furyl)-5-(1H-pyrrolo[2,3-b]pyridin-3-ylmethylene)-3,5-dihydro-4H-imidazol-4-one;
(5Z)-2-[3-(4-methylpiperazin-1-yl)phenyl]-5-(1H-pyrrolo[2,3-b]pyridin-3-ylmethylene)-3,5-dihydro-4H-imidazol-4-one;
(5E)-2-[4-(4-methylpiperazin-1-yl)phenyl]-5-(1H-pyrrolo[2,3-b]pyridin-3-ylmethylene)-3,5-dihydro-4H-imidazol-4-one dihydrochloride;
(5Z)-2-[4-(4-methylpiperazin-1-yl)phenyl]-5-(1H-pyrrolo[2,3-b]pyridin-3-ylmethylene)-3,5-dihydro-4H-imidazol-4-one dihydrochloride;
(5Z)-2-{4-[(1-methylpiperidin-4-yl)oxy]phenyl}-5-(1H-pyrrolo[2,3-b]pyridin-3-ylmethylene)-3,5-dihydro-4H-imidazol-4-one dihydrochloride;
(5Z)-2-morpholin-4-yl-5-(1H-pyrrolo[2,3-b]pyridin-3-ylmethylene)-3,5-dihydro-4H-imidazol-4-one dihydrochloride;
(5Z)-2-(4-methylpiperazin-1-yl)-5-(1H-pyrrolo[2,3-b]pyridin-3-ylmethylene)-3,5-dihydro-4H-imidazol-4-one dihydrochloride;
(5Z)-2-(4-phenylpiperazin-1-yl)-5-(1H-pyrrolo[2,3-b]pyridin-3-ylmethylene)-3,5-dihydro-4H-imidazol-4-one trihydrochloride;
(5Z)-2-piperidin-1-yl-5-(1H-pyrrolo[2,3-b]pyridin-3-ylmethylene)-3,5-dihydro-4H-imidazol-4-one dihydrochloride;
(5Z)-2-[3-(hydroxymethyl)piperidin-1-yl]-5-(1H-pyrrolo[2,3-b]pyridin-3-ylmethylene)-3,5-dihydro-4H-imidazol-4-one dihydrochloride;
(5Z)-2-pyrrolidin-1-yl-5-(1H-pyrrolo[2,3-b]pyridin-3-ylmethylene)-3,5-dihydro-4H-imidazol-4-one dihydrochloride;
(5Z)-2-(4-benzylpiperazin-1-yl)-5-(1H-pyrrolo[2,3-b]pyridin-3-ylmethylene)-3,5-dihydro-4H-imidazol-4-one trihydrochloride;
(5Z)-2-(4-isopropylpiperazin-1-yl)-5-(1H-pyrrolo[2,3-b]pyridin-3-ylmethylene)-3,5-dihydro-4H-imidazol-4-one dihydrochloride;
(5Z)-5-(1H-pyrrolo[2,3-b]pyridin-3-ylmethylene)-2-[4-(tetrahydrofuran-2-ylmethyl)piperazin-1-yl]-3,5-dihydro-4H-imidazol-4-one dihydrochloride;
(5Z)-2-[4-(2-hydroxyethyl)piperazin-1-yl]-5-(1H-pyrrolo[2,3-b]pyridin-3-ylmethylene)-3,5-dihydro-4H-imidazol-4-one dihydrochloride;
(5Z)-2-(4-phenylpiperidin-1-yl)-5-(1H-pyrrolo[2,3-b]pyridin-3-ylmethylene)-3,5-dihydro-4H-imidazol-4-one ditrifluoroacetate;
(5Z)-2-(1,4'-bipiperidin-1'-yl)-5-(1H-pyrrolo[2,3-b]pyridin-3-ylmethylene)-3,5-dihydro-4H-imidazol-4-one trihydrochloride;
(5Z)-2-azepan-1-yl-5-(1H-pyrrolo[2,3-b]pyridin-3-ylmethylene)-3,5-dihydro-4H-imidazol-4-one dihydrochloride;
(5Z)-1-[5-oxo-4-(1H-pyrrolo[2,3-b]pyridin-3-ylmethylene)-4,5-dihydro-1H-imidazol-2-yl]piperidine-3-carboxamide ditrifluoroacetate;
(5Z)-2-(piperazin-1-yl)-5-(1H-pyrrolo[2,3-b]pyridin-3-ylmethylene)-3,5-dihydro-4H-imidazol-4-one tritrifluoroacetate;
(5Z)-2-[4-(2-furoyl)piperazin-1-yl]-5-(1H-pyrrolo[2,3-b]pyridin-3-ylmethylene)-3,5-dihydro-4H-imidazol-4-one dihydrochloride;
(5Z)-2-(1,3-dihydro-2H-isoindol-2-yl)-5-(1H-pyrrolo[2,3-b]pyridin-3-ylmethylene)-3,5-dihydro-4H-imidazol-4-one dihydrochloride;
(5Z)-2-(2-methylmorpholin-4-yl)-5-(1H-pyrrolo[2,3-b]pyridin-3-ylmethylene)-3,5-dihydro-4H-imidazol-4-one dihydrochloride;
(5Z)-2-(4-propylpiperazin-1-yl)-5-(1H-pyrrolo[2,3-b]pyridin-3-ylmethylene)-3,5-dihydro-4H-imidazol-4-one dihydrochloride;
(5Z)-2-(4-methylpiperidin-1-yl)-5-(1H-pyrrolo[2,3-b]pyridin-3-ylmethylene)-3,5-dihydro-4H-imidazol-4-one dihydrochloride;
(5Z)-2-(2,6-dimethylmorpholin-4-yl)-5-(1H-pyrrolo[2,3-b]pyridin-3-ylmethylene)-3,5-dihydro-4H-imidazol-4-one dihydrochloride;
(5Z)-2-(3,5-dimethylpiperidin-1-yl)-5-(1H-pyrrolo[2,3-b]pyridin-3-ylmethylene)-3,5-dihydro-4H-imidazol-4-one ditrifluoroacetate;
(5Z)-2-[4-(cyclohexylmethyl)piperazin-1-yl]-5-(1H-pyrrolo[2,3-b]pyridin-3-ylmethylene)-3,5-dihydro-4H-imidazol-4-one trihydrochloride;
(5Z)-2-(4-benzylpiperidin-1-yl)-5-(1H-pyrrolo[2,3-b]pyridin-3-ylmethylene)-3,5-dihydro-4H-imidazol-4-one dihydrochloride;
(5Z)-2-(4-pyrrolidin-1-ylpiperidin-1-yl)-5-(1H-pyrrolo[2,3-b]pyridin-3-ylmethylene)-3,5-dihydro-4H-imidazol-4-one trihydrochloride;
(5Z)-2-(1,4-diazepan-1-yl)-5-(1H-pyrrolo[2,3-b]pyridin-3-ylmethylene)-3,5-dihydro-4H-imidazol-4-one trihydrochloride;

(5Z)-2-[4-(3,4-dichlorophenyl)piperazin-1-yl]-5-(1H-pyrrolo[2,3-b]pyridin-3-ylmethylene)-3,5-dihydro-4H-imidazol-4-one trihydrochloride;

(5Z)-(2-[4-(2-fluorophenyl)piperazin-1-yl]-5-(1H-pyrrolo[2,3-b]pyridin-3-ylmethylene)-3,5-dihydro-4H-imidazol-4-one trihydrochloride;

(5Z)-2-[4-(2-methoxyethyl)piperazin-1-yl]-5-(1H-pyrrolo[2,3-b]pyridin-3-ylmethylene)-3,5-dihydro-4H-imidazol-4-one trihydrochloride;

(5Z)-2-[4-(4-fluorophenyl)piperazin-1-yl]-5-(1H-pyrrolo[2,3-b]pyridin-3-ylmethylene)-3,5-dihydro-4H-imidazol-4-one trihydrochloride;

(5Z)-2-[(2R)-2-benzylmorpholin-4-yl]-5-(1H-pyrrolo[2,3-b]pyridin-3-ylmethylene)-3,5-dihydro-4H-imidazol-4-one hydrochloride trifluoroacetate;

(5Z)-2-(cyclohexylamino)-5-(1H-pyrrolo[2,3-b]pyridin-3-ylmethylene)-3,5-dihydro-4H-imidazol-4-one hydrochloride;

(5Z)-2-[(1-benzylpiperidin-4-yl)amino]-5-(1H-pyrrolo[2,3-b]pyridin-3-ylmethylene)-3,5-dihydro-4H-imidazol-4-one trihydrochloride;

(5Z)-2-(benzylamino)-5-(1H-pyrrolo[2,3-b]pyridin-3-ylmethylene)-3,5-dihydro-4H-imidazol-4-one hydrochloride;

(5Z)-2-[(2-hydroxyethyl)amino]-5-(1H-pyrrolo[2,3-b]pyridin-3-ylmethylene)-3,5-dihydro-4H-imidazol-4-one dihydrochloride;

(5Z)-2-[(3,3-dimethylbutyl)amino]-5-(1H-pyrrolo[2,3-b]pyridin-3-ylmethylene)-3,5-dihydro-4H-imidazol-4-one dihydrochloride;

(5Z)-2-[(2-furylmethyl)amino]-5-(1H-pyrrolo[2,3-b]pyridin-3-ylmethylene)-3,5-dihydro-4H-imidazol-4-one dihydrochloride;

(5Z)-2-(cyclopropylamino)-5-(1H-pyrrolo[2,3-b]pyridin-3-ylmethylene)-3,5-dihydro-4H-imidazol-4-one dihydrochloride;

(5Z)-5-(1H-pyrrolo[2,3-b]pyridin-3-ylmethylene)-2-[(thien-2-ylmethyl)amino]-3,5-dihydro-4H-imidazol-4-one dihydrochloride;

(5Z)-2-(propylamino)-5-(1H-pyrrolo[2,3-b]pyridin-3-ylmethylene)-3,5-dihydro-4H-imidazol-4-one dihydrochloride;

(5Z)-2-[(2-piperidin-1-ylethyl)amino]-5-(1H-pyrrolo[2,3-b]pyridin-3-ylmethylene)-3,5-dihydro-4H-imidazol-4-one dihydrochloride;

(5Z)-2-[(3-furylmethyl)amino]-5-(1H-pyrrolo[2,3-b]pyridin-3-ylmethylene)-3,5-dihydro-4H-imidazol-4-one dihydrochloride;

(5Z)-2-[(2-morpholin-1-ylethyl)amino]-5-(1H-pyrrolo[2,3-b]pyridin-3-ylmethylene)-3,5-dihydro-4H-imidazol-4-one dihydrochloride;

(5Z)-5-(1H-pyrrolo[2,3-b]pyridin-3-ylmethylene)-2-[(tetrahydrofuran-2-ylmethyl)amino]-3,5-dihydro-4H-imidazol-4-one hydrochloride;

(5Z)-2-(pentylamino)-5-(1H-pyrrolo[2,3-b]pyridin-3-ylmethylene)-3,5-dihydro-4H-imidazol-4-one dihydrochloride;

(5Z)-2-(heptylamino)-5-(1H-pyrrolo[2,3-b]pyridin-3-ylmethylene)-3,5-dihydro-4H-imidazol-4-one ditrifluoroacetate;

(5Z)-2-[(cyclohexylmethyl)amino]-5-(1H-pyrrolo[2,3-b]pyridin-3-ylmethylene)-3,5-dihydro-4H-imidazol-4-one dihydrochloride;

(5Z)-2-[(2-methylbutyl)amino]-5-(1H-pyrrolo[2,3-b]pyridin-3-ylmethylene)-3,5-dihydro-4H-imidazol-4-one dihydrochloride;

(5Z)-2-[(cyclopropylmethyl)amino]-5-(1H-pyrrolo[2,3-b]pyridin-3-ylmethylene)-3,5-dihydro-4H-imidazol-4-one dihydrochloride;

(5Z)-2-[(3-isopropoxypropyl)amino]-5-(1H-pyrrolo[2,3-b]pyridin-3-ylmethylene)-3,5-dihydro-4H-imidazol-4-one dihydrochloride;

(5Z)-2-(ethylamino)-5-(1H-pyrrolo[2,3-b]pyridin-3-ylmethylene)-3,5-dihydro-4H-imidazol-4-one dihydrochloride;

(5Z)-2-[(2-phenylethyl)amino]-5-(1H-pyrrolo[2,3-b]pyridin-3-ylmethylene)-3,5-dihydro-4H-imidazol-4-one dihydrochloride;

(5Z)-2-[(4-fluorobenzyl)amino]-5-(1H-pyrrolo[2,3-b]pyridin-3-ylmethylene)-3,5-dihydro-4H-imidazol-4-one dihydrochloride;

(5Z)-2-[(3-fluorobenzyl)amino]-5-(1H-pyrrolo[2,3-b]pyridin-3-ylmethylene)-3,5-dihydro-4H-imidazol-4-one dihydrochloride;

(5Z)-2-[(2-fluorobenzyl)amino]-5-(1H-pyrrolo[2,3-b]pyridin-3-ylmethylene)-3,5-dihydro-4H-imidazol-4-one dihydrochloride;

(5Z)-2-[(3-chlorobenzyl)amino]-5-(1H-pyrrolo[2,3-b]pyridin-3-ylmethylene)-3,5-dihydro-4H-imidazol-4-one dihydrochloride;

(5Z)-2-[(4-chlorobenzyl)amino]-5-(1H-pyrrolo[2,3-b]pyridin-3-ylmethylene)-3,5-dihydro-4H-imidazol-4-one dihydrochloride;

(5Z)-2-[(3,4-dichlorobenzyl)amino]-5-(1H-pyrrolo[2,3-b]pyridin-3-ylmethylene)-3,5-dihydro-4H-imidazol-4-one dihydrochloride;

(5Z)-2-[(3-bromobenzyl)amino]-5-(1H-pyrrolo[2,3-b]pyridin-3-ylmethylene)-3,5-dihydro-4H-imidazol-4-one dihydrochloride;

(5Z)-2-[(3-methylbenzyl)amino]-5-(1H-pyrrolo[2,3-b]pyridin-3-ylmethylene)-3,5-dihydro-4H-imidazol-4-one dihydrochloride;

(5Z)-2-[(4-methylbenzyl)amino]-5-(1H-pyrrolo[2,3-b]pyridin-3-ylmethylene)-3,5-dihydro-4H-imidazol-4-one dihydrochloride;

(5Z)-5-(1H-pyrrolo[2,3-b]pyridin-3-ylmethylene)-2-{[4-(trifluoromethyl)benzyl]amino}-3,5-dihydro-4H-imidazol-4-one dihydrochloride;

(5Z)-2-[(4-methoxybenzyl)amino]-5-(1H-pyrrolo[2,3-b]pyridin-3-ylmethylene)-3,5-dihydro-4H-imidazol-4-one dihydrochloride;

(5Z)-2-[(3,4-dimethoxybenzyl)amino]-5-(1H-pyrrolo[2,3-b]pyridin-3-ylmethylene)-3,5-dighydro-4H-imidazol-4-one dihydrochloride;

(5Z)-5-(1H-pyrrolo[2,3-b]pyridin-3-ylmethylene)-2-{[(1R,2R,3R)-2,6,6-trimethylbicyclo[3.1.1]hept-3-yl]amino}-3,5-dihydro-4H-imidazol-4-one dihydrochloride;

(5Z)-2-[(3,4-difluorobenzyl)amino]-5-(1H-pyrrolo[2,3-b]pyridin-3-ylmethylene)-3,5-dihydro-4H-imidazol-4-one dihydrochloride;

(5Z)-2-(cycloheptylamino)-5-(1H-pyrrolo[2,3-b]pyridin-3-ylmethylene)-3,5-dihydro-4H-imidazol-4-one dihydrochloride;

(5Z)-2-[(2-methylcyclohexyl)amino]-5-(1H-pyrrolo[2,3-b]pyridin-3-ylmethylene)-3,5-dihydro-4H-imidazol-4-one dihydrochloride;

(5Z)-2-[(3-methylcyclohexyl)amino]-5-(1H-pyrrolo[2,3-b]pyridin-3-ylmethylene)-3,5-dihydro-4H-imidazol-4-one dihydrochloride;

(5Z)-2-[(2,2'-bithien-5-ylmethyl)amino]-5-(1H-pyrrolo[2,3-b]pyridin-3-ylmethylene)-3,5-dihydro-4H-imidazol-4-one dihydrochloride;

(5Z)-2-{[(3-methylthien-2-yl)methyl]amino}-5-(1H-pyrrolo[2,3-b]pyridin-3-ylmethylene)-3,5-dihydro-4H-imidazol-4-one dihydrochloride;

(5Z)-5-(1H-pyrrolo[2,3-b]pyridin-3-ylmethylene)-2-(1,2,3,4-tetrahydronaphthalen-1-ylamino)-3,5-dihydro-4H-imidazol-4-one dihydrochloride;

(5Z)-2-{[(5-pyridin-2-ylthien-2-yl)methyl]amino}-5-(1H-pyrrolo[2,3-b]pyridin-3-ylmethylene)-3,5-dihydro-4H-imidazol-4-one dihydrochloride;

(5Z)-2-[(4-tert-butylcyclohexyl)amino]-5-(1H-pyrrolo[2,3-b]pyridin-3-ylmethylene)-3,5-dihydro-4H-imidazol-4-one dihydrochloride;

(5Z)-5-(1H-pyrrolo[2,3-b]pyridin-3-ylmethylene)-2-{[(1R,2S,4R)-1,7,7-trimethylbicyclo[2.2.1]hept-2-yl]amino}-3,5-dihydro-4H-imidazol-4-one dihydrochloride;

2-(cyclopentylamino)-5-(1H-pyrrolo[2,3-b]pyridin-3-ylmethylene)-3,5-dihydro-4H-imidazol-4-one dihydrochloride;

(5Z)-2-[(4-methylcyclohexyl)amino]-5-(1H-pyrrolo[2,3-b]pyridin-3-ylmethylene)-3,5-dihydro-4H-imidazol-4-one dihydrochloride;

(5Z)-2-[(2,3-dimethylcyclohexyl)amino]-5-(1H-pyrrolo[2,3-b]pyridin-3-ylmethylene)-3,5-dihydro-4H-imidazol-4-one dihydrochloride;

(5Z)-2-[(1-phenylethyl)amino]-5-(1H-pyrrolo[2,3-b]pyridin-3-ylmethylene)-3,5-dihydro-4H-imidazol-4-one dihydrochloride;

(5Z)-2-{[1-(4-fluorophenyl)ethyl]amino}-5-(1H-pyrrolo[2,3-b]pyridin-3-ylmethylene)-3,5-dihydro-4H-imidazol-4-one dihydrochloride;

(5Z)-2-[(2,3-dihydro-1H-inden-1-ylmethyl)amino]-5-(1H-pyrrolo[2,3-b]pyridin-3-ylmethylene)-3,5-dihydro-4H-imidazol-4-one trifluoroacetate;

(5Z)-2-{[4-(4-methylpiperazin-1-yl)benzyl]amino}-5-(1H-pyrrolo[2,3-b]pyridin-3-ylmethylene)-3,5-dihydro-4H-imidazol-4-one dihydrochloride;

(5Z)-2-[(1-phenyl propyl)amino]-5-(1H-pyrrolo[2,3-b]pyridin-3-ylmethylene)-3,5-dihydro-4H-imidazol-4-one trifluoroacetate;

(5Z)-5-(1H-pyrrolo[2,3-b]pyridin-3-ylmethylene)-2-[(1S)-1,2,3,4-tetrahydronaphthalen-1-ylamino]-3,5-dihydro-4H-imidazol-4-one dihydrochloride;

(5Z)-2-[(4-bromobenzyl)amino]-5-(1H-pyrrolo[2,3-b]pyridin-3-ylmethylene)-3,5-dihydro-4H-imidazol-4-one dihydrochloride;

(5Z)-2-[(2,3-dihydro-1H-inden-2-ylmethyl)amino]-5-(1H-pyrrolo[2,3-b]pyridin-3-ylmethylene)-3,5-dihydro-4H-imidazol-4-one dihydrochloride;

(5Z)-2-[(1-benzothien-2-ylmethyl)amino]-5-(1H-pyrrolo[2,3-b]pyridin-3-ylmethylene)-3,5-dihydro-4H-imidazol-4-one dihydrochloride;

(5Z)-2-{[(1S,2R,5S)-2-isopropyl-5-methylcyclohexyl]amino)-5-(1H-pyrrolo[2,3-b]pyridin-3-ylmethylene)-3,5-dihydro-4H-imidazol-4-one trifluoroacetate;

(5Z)-2-(bicyclo[2.2.1]hept-2-ylamino)-5-(1H-pyrrolo[2,3-b]pyridin-3-ylmethylene)-3,5-dihydro-4H-imidazol-4-one trifluoroacetate;

(5Z)-2-{([3-fluoro-5-(trifluoromethyl)benzyl]amino}-5-(1H-pyrrolo[2,3-b]pyridin-3-ylmethylene)-3,5-dihydro-4H-imidazol-4-one trifluoroacetate;

(5Z)-2-[(1-ethylpropyl)amino]-5-(1H-pyrrolo[2,3-b]pyridin-3-ylmethylene)-3,5-dihydro-4H-imidazol-4-one dihydrochloride;

(5Z)-5-(1H-pyrrolo[2,3-b]pyridin-3-ylmethylene)-2-[(2,2,6,6-tetramethy-piperidin-4-yl)amino]-3,5-dihydro-4H-imidazol-4-one dihydrochloride;

(5Z)-2-(adamantanamino)-5-(1H-pyrrolo[2,3-b]pyridin-3-ylmethylene)-3,5-dihydro-4H-imidazol-4-one dihydrochloride;

(5Z)-2-(isopropylamino)-5-(1H-pyrrolo[2,3-b]pyridin-3-ylmethylene)-3,5-dihydro-4H-imidazol-4-one dihydrochloride;

(5Z)-2-{[3-(dimethylamino)-2,2-dimethylpropyl]amino}-5-(1H-pyrrolo[2,3-b]pyridin-3-ylmethylene)-3,5-dihydro-4H-imidazol-4-one dihydrochloride;

(5Z)-2-[(3R)-1-azabicyclo[2.2.2]oct-3-ylamino]-5-(1H-pyrrolo[2,3-b]pyridin-3-ylmethylene)-3,5-dihydro-4H-imidazol-4-one hydrochloride trifluoroacetate;

(5Z)-2-{[(1R,5S)-8-methyl-8-azabicyclo[3.2.1]oct-3-yl]amino}-5-(1H-pyrrolo[2,3-b]pyridin-3-ylmethylene)-3,5-dihydro-4H-imidazol-4-one hydrochloride trifluoroacetate;

(5Z)-2-[(3S)-1-azabicyclo[2.2.2]oct-3-ylamino]-5-(1H-pyrrolo[2,3-b]pyridin-3-ylmethylene)-3,5-dihydro-4H-imidazol-4-one hydrochloride trifluoroacetate;

(5Z)-2-{[(1S)-1-phenyl-2-pyrrolidin-1-ylethyl]amino}-5-(1H-pyrrolo[2,3-b]pyridin-3-ylmethylene)-3,5-dihydro-4H-imidazol-4-one hydrochloride trifluoroacetate;

(5Z)-2-[(4-hydroxycyclohexyl)amino]-5-(1H-pyrrolo[2,3-b]pyridin-3-ylmethylene)-3,5-dihydro-4H-imidazol-4-one;

(5Z)-2-{[(2S)-2-hydroxycyclohexyl]amino}-5-(1H-pyrrolo[2,3-b]pyridin-3-ylmethylene)-3,5-dihydro-4H-imidazol-4-one;

(5Z)-2-{[(1S,2S,3R,4R)-3-(hydroxymethyl)bicyclo[2.2.1]hept-2-yl]amino}-5-(1H-pyrrolo[2,3-b]pyridin-3-ylmethylene)-3,5-dihydro-4H-imidazol-4-one dihydrochloride;

(5Z)-2-(adamantylmethylamino)-5-(1H-pyrrolo[2,3-b]pyridin-3-ylmethylene)-3,5-dihydro-4H-imidazol-4-one dihydrochloride;

(5Z)-2-[(1S,2R,4R)-bicyclo[2.2.1]hept-2-ylamino]-5-(1H-pyrrolo[2,3-b]pyridin-3-ylmethylene)-3,5-dihydro-4H-imidazol-4-one dihydrochloride;

(5Z)-2-{[(1R)-1-phenylethyl]amino}-5-(1H-pyrrolo[2,3-b]pyridin-3-ylmethylene)-3,5-dihydro-4H-imidazol-4-one dihydrochloride;

(5Z)-5-(1H-pyrrolo[2,3-b]pyridin-3-ylmethylene)-2-{[(1R,4R)-1,7,7-trimethylbicyclo[2.2.1]hept-2-yl]amino)-3,5-dihydro-4H-imidazol-4-one dihydrochloride;

(5Z)-2-{[(1R,2S,3R,4S)-3-(hydroxymethyl)bicyclo[2.2.1]hept-2-yl]amino}-)-5-(1H-pyrrolo[2,3-b]pyridin-3-ylmethylene)-3,5-dihydro-4H-imidazol-4-one dihydrochloride;

(5Z)-5-(1H-pyrrolo[2,3-b]pyridin-3-ylmethylene)-2-([(1R,2R,3R,5S)-2,6,6-trimethylbicyclo[3.1.1]hept-3-yl]amino}-3,5-dihydro-4H-imidazol-4-one dihydrochloride;

(5Z)-2-{[(1S)-2-(4-methylpiperazin-1-yl)-1-phenylethyl]amino}-5-(1H-pyrrolo[2,3-b]pyridin-3-ylmethylene)-3,5-dihydro-4H-imidazol-4-one dihydrochloride;

(5Z)-2-{[(1S)-1-phenyl-2-piperidin-1-ylethyl]amino}-5-(1H-pyrrolo[2,3-b]pyridin-3-ylmethylene)-3,5-dihydro-4H-imidazol-4-one dihydrochloride;

(5Z)-2-{[(1S)-2-morpholin-4-yl-1-phenylethyl]amino}-5-(1H-pyrrolo[2,3-b]pyridin-3-ylmethylene)-3,5-dihydro-4H-imidazol-4-one dihydrochloride;

(5Z)-2-{[1-(3-fluorophenyl)ethyl]amino}-5-(1H-pyrrolo[2,3-b]pyridin-3-ylmethylene)-3,5-dihydro-4H-imidazol-4-one dihydrochloride;

(5Z)-2-[(1,2,2,6,6-pentamethylpiperidin-4-yl)amino]-5-(1H-pyrrolo[2,3-b]pyridin-3-ylmethylene)-3,5-dihydro-4H-imidazol-4-one dihydrochloride;

(5Z)-2-[(2-hydroxy-1-phenylethyl)amino]-5-(1H-pyrrolo[2,3-b]pyridin-3-ylmethylene)-3,5-dihydro-4H-imidazol-4-one dihydrochloride;

(5Z)-2-[(3-hydroxy-1-phenylpropyl)amino]-5-(1H-pyrrolo[2,3-b]pyridin-3-ylmethylene)-3,5-dihydro-4H-imidazol-4-one dihydrochloride;

(5Z)-2-{[(1R)-1-phenyl-2-pyrrolidin-1-ylethyl]amino}-5-(1H-pyrrolo[2,3-b]pyridin-3-ylmethylene)-3,5-dihydro-4H-imidazol-4-one;

(5Z)-2-{[(1R)-1-phenylethyl]amino}-5-(1H-pyrrolo[2,3-b]pyridin-3-ylmethylene)-3,5-dihydro-4H-imidazol-4-one dihydrochloride;

(5Z)-2-{[(1S)-1-phenylethyl]amino}-5-(1H-pyrrolo[2,3-b]pyridin-3-ylmethylene)-3,5-dihydro-4H-imidazol-4-one dihydrochloride;

(5Z)-2-(benzylthio)-5-(1H-pyrrolo[2,3-b]pyridin-3-ylmethylene)-3,5-dihydro-4H-imidazol-4-one;

2-(benzylamino)-5-(1H-pyrrolo[2,3-b]pyridin-3-ylmethylene)-1,3-thiazol-4(5H)-one hydrochloride;

(5Z)-2-{[(1S)-1-phenylethyl]amino}-5-(1H-pyrrolo[2,3-b]pyridin-3-ylmethylene)-1,3-thiazol-4(5H)-one hydrochloride;

(5Z)-2-[4-(2-hydroxyethyl)piperazin-1-yl]-5-(1H-pyrrolo[2,3-b]pyridin-3-ylmethylene)-1,3-thiazol-4(5H)-one dihydrochloride;

(5Z)-2-(isopropylamino)-5-(1H-pyrrolo[2,3-b]pyridin-3-ylmethylene)-1,3-thiazol-4(5H)-one dihydrochloride;

(5Z)-2-[(3R)-1-azabicyclo[2.2.2]oct-3-ylamino]-5-(1H-pyrrolo[2,3-b]pyridin-3-ylmethylene)-1,3-thiazol-4(5H)-one dihydrochloride;

(5Z)-2-[(2-furylmethyl)amino]-5-(1H-pyrrolo[2,3-b]pyridin-3-ylmethylene)-1,3-thiazol-4(5H)-one dihydrochloride;

(5Z)-1-methyl-N-[1H-pyrrolo[2,3-b]pyridin-5-yl]piperidine-4-carboxamide;

(5Z)-N-(3-{[2-(benzylamino)-5-oxo-1,5-dihydro-4H-imidazol-4-ylidene]methyl}-1H-pyrrolo[2,3-b]pyridin-5-yl)acetamide hydrochloride;

(5E)-N-(3-{[2-(benzylamino)-5-oxo-1,5-dihydro-4H-imidazol-4-ylidene]methyl}-1H-pyrrolo[2,3-b]pyridin-5-yl)acetamide hydrochloride;

(5Z)-2-(benzylamino)-5-[(5-nitro-1H-pyrrolo[2,3-b]pyridin-3-yl)methylene]-3,5-dihydro-4H-imidazol-4-one;

(5E)-2-(benzylamino)-5-[(5-nitro-1H-pyrrolo[2,3-b]pyridin-3-yl)methylene]-3,5-dihydro-4H-imidazol-4-one;

(5Z)-5-[(5-amino-1H-pyrrolo[2,3-b]pyridin-3-yl)methylene]-2-(benzylamino)-3,5-dihydro-4H-imidazol-4-one;

(5E)-5-[(5-amino-1H-pyrrolo[2,3-b]pyridin-3-yl)methylene]-2-(benzylamino)-3,5-dihydro-4H-imidazol-4-one;

(5Z)-2-(benzylamino)-5-[1-(1H-pyrrolo[2,3-b]pyridin-3-yl)ethylidene]-3,5-dihydro-4H-imidazol-4-one hydrochloride;

N-[3-(4-methylpiperazin-1-yl)benzoyl]glycine;

(5Z)-2-(4-chlorophenyl)-5-(1H-pyrrolo[2,3-b]pyridin-3-ylmethylene)-3,5-dihydro-4H-imidazol-4-one;

(5Z)-2-[3-(hydroxymethyl)phenyl]-5-(1H-pyrrolo[2,3-b]pyridin-3-ylmethylene)-3,5-dihydro-4H-imidazol-4-one;

(5Z)-2-pyridin-4-yl-5-(1H-pyrrolo[2,3-b]pyridin-3-ylmethylene)-3,5-dihydro-4H-imidazol-4-one;

(5Z)-2-pyridin-2-yl-5-(1H-pyrrolo[2,3-b]pyridin-3-ylmethylene)-3,5-dihydro-4H-imidazol-4-one;

(5Z)-2-{3-[(1-methylpiperidin-4-yl)oxy]phenyl}-5-(1H-pyrrolo[2,3-b]pyridin-3-ylmethylene)-3,5-dihydro-4H-imidazol-4-one;

(5Z)-2-(4-morpholin-4-ylphenyl)-5-(1H-pyrrolo[2,3-b]pyridin-3-ylmethylene)-3,5-dihydro-4H-imidazol-4-one;

(5Z)-2-(3-morpholin-4-ylphenyl)-5-(1H-pyrrolo[2,3-b]pyridin-3-ylmethylene)-3,5-dihydro-4H-imidazol-4-one;

(5Z)-2-(propylamino)-5-(1H-pyrrolo[2,3-b]pyridin-3-ylmethylene)-3,5-dihydro-4H-imidazol-4-one;

(5Z)-2-[(2-pyrrolidin-1-ylethyl)amino]-5-(1H-pyrrolo[2,3-b]pyridin-3-ylmethylene)-3,5-dihydro-4H-imidazol-4-one;

(5Z)-2-{[2-(dimethylamino)ethyl]amino}-5-(1H-pyrrolo[2,3-b]pyridin-3-ylmethylene)-3,5-dihydro-4H-imidazol-4-one;

(5Z)-2-[4-(hydroxymethyl)piperidin-1-yl]-5-(1H-pyrrolo[2,3-b]pyridin-3-ylmethylene)-3,5-dihydro-4H-imidazol-4-one;

(5Z)-1-[5-oxo-4-(1H-pyrrolo[2,3-b]pyridin-3-ylmethylene)-4,5-dihydro-1H-imidazol-2-yl]piperidine-4-carboxamide;

(5Z)-N,N-diethyl-1-[5-oxo-4-(1H-pyrrolo[2,3-b]pyridin-3-ylmethylene)-4,5-dihydro-1H-imidazol-2-yl]piperidine-3-carboxamide;

(5Z)-2-(4-hydroxypiperidin-1-yl)-5-(1H-pyrrolo[2,3-b]pyridin-3-ylmethylene)-3,5-dihydro-4H-imidazol-4-one;

(5Z)-2-(3-hydroxypiperidin-1-yl)-5-(1H-pyrrolo[2,3-b]pyridin-3-ylmethylene)-3,5-dihydro-4H-imidazol-4-one;

(5Z)-2-azetidin-1-yl-5-(1H-pyrrolo[2,3-b]pyridin-3-ylmethylene)-3,5-dihydro-4H-imidazol-4-one (5Z)-2-(2,5-dihydro-1H-pyrrol-1-yl)-5-(1H-pyrrolo[2,3-b]pyridin-3-ylmethylene)-3,5-dihydro-4H-imidazol-4-one;

(5Z)-2-(3-hydroxypyrrolidin-1-yl)-5-(1H-pyrrolo[2,3-b]pyridin-3-ylmethylene)-3,5-dihydro-4H-imidazol-4-one;

(5Z)-2-pyrazolidin-1-yl-5-(1H-pyrrolo[2,3-b]pyridin-3-ylmethylene)-3,5-dihydro-4H-imidazol-4-one;

(5Z)-1-[5-oxo-4-(1H-pyrrolo[2,3-b]pyridin-3-ylmethylene)-4,5-dihydro-1H-imidazol-2-yl]prolinamide;

(5Z)-2-(4-allylpiperazin-1-yl)-5-(1H-pyrrolo[2,3-b]pyridin-3-ylmethylene)-3,5-dihydro-4H-imidazol-4-one;

(5Z)-2-(4-ethylpiperazin-1-yl)-5-(1H-pyrrolo[2,3-b]pyridin-3-ylmethylene)-3,5-dihydro-4H-imidazol-4-one;

(5Z)-2-[4-(2-oxo-2-pyrrolidin-1-ylethyl)piperazin-1-yl]-5-(1H-pyrrolo[2,3-b]pyridin-3-ylmethylene)-3,5-dihydro-4H-imidazol-4-one;

(5Z)-N-isopropyl-2-{4-[5-oxo-4-(1H-pyrrolo[2,3-b]pyridin-3-ylmethylene)-4,5-dihydro-1H-imidazol-2-yl]piperazin-1-yl}acetamide;

(5Z)-2-[4-(4-hydroxyphenyl)piperazin-1-yl]-5-(1H-pyrrolo[2,3-b]pyridin-3-ylmethylene)-3,5-dihydro-4H-imidazol-4-one;

(5Z)-5-(1H-pyrrolo[2,3-b]pyridin-3-ylmethylene)-2-[4-(tetrahydrofuran-2-ylcarbonyl)piperazin-1-yl]-3,5-dihydro-4H-imidazol-4-one;

(5Z)-5-(1H-pyrrolo[2,3-b]pyridin-3-ylmethylene)-2-{[(1S,2R,4S)-1,3,3-trimethylbicyclo[2.2.1]hept-2-yl]amino}-3,5-dihydro-4H-imidazol-4-one;

(5Z)-5-(1H-pyrrolo[2,3-b]pyridin-3-ylmethylene)-2-{[(1S,2R,4R)-1,7,7-trimethylbicyclo[2.2.1]hept-2-yl]amino}-3,5-dihydro-4H-imidazol-4-one;

(5Z)-2-[(1-phenylcyclopropyl)amino]-5-(1H-pyrrolo[2,3-b]pyridin-3-ylmethylene)-3,5-dihydro-4H-imidazol-4-one;

(5Z)-2-[(2-morpholin4-ylethyl)amino]-5-(1H-pyrrolo[2,3-b]pyridin-3-ylmethylene)-3,5-dihydro-4H-imidazol-4-one;

(5Z)-2-[(2-pyrrolidin-1-ylethyl)amino]-5-(1H-pyrrolo[2,3-b]pyridin-3-ylmethylene)-3,5-dihydro-4H-imidazol-4-one;

(5Z)-1-methyl-N-{3-[(5-oxo-2-phenyl-1,5-dihydro-4H-imidazol-4-ylidene)methyl]-1H-pyrrolo[2,3-b]pyridin-5-yl}piperidine-4-carboxamide;

(5Z)-N₃-,N₃-dimethyl-N₁-{3-[(5-oxo-2-phenyl-1,5-dihydro-4H-imidazol-4-ylidene)methyl]-1H-pyrrolo[2,3-b]pyridin-5-yl}-beta-alaninamide;

(5Z)-3-(4-methylpiperazin-1-yl)-N-{3-[(5-oxo-2-phenyl-1,5-dihydro-4H-imidazol-4-ylidene)methyl]-1H-pyrrolo[2,3-b]pyridin-5-yl}benzamide;

(5Z)-4-(4-methylpiperazin-1-yl)-N-{3-[(5-oxo-2-phenyl-1,5-dihydro-4H-imidazol-4-ylidene)methyl]-1H-pyrrolo[2,3-b]pyridin-5-yl}benzamide;

(5Z)-N-(3-{[2-(benzylamino)-5-oxo-1,5-dihydro-4H-imidazol-4-ylidene]methyl}-1H-pyrrolo[2,3-b]pyridin-5-yl)-1-methylpiperidine-4-carboxamide;

(5Z)-1-methyl-N-[3-({5-oxo-2-[(1-phenylethyl)amino]-1,5-dihydro-4H-imidazol-4-ylidene}methyl)-1H-pyrrolo[2,3-b]pyridin-5-yl]piperidine-4-carboxamide;

(5Z)-N-(3-{[2-(cyclohexylamino)-5-oxo-1,5-dihydro-4H-imidazol-4-ylidene]methyl}-1H-pyrrolo[2,3-b]pyridin-5-yl)-1-methylpiperidine-4-carboxamide;

(5Z)-N-(3-{[2-(bicyclo[2.2.1]hept-2-ylamino)-5-oxo-1,5-dihydro-4H-imidazol-4-ylidene]methyl}-1H-pyrrolo[2,3-b]pyridin-5-yl)-1-methylpiperidine-4-carboxamide;

(5Z)-N-(3-{[2-(1-adamantylamino)-5-oxo-1,5-dihydro-4H-imidazol-4-ylidene]methyl}-1H-pyrrolo[2,3-b]pyridin-5-yl)-1-methylpiperidine-4-carboxamide;

(5Z)-1-methyl-N-[3-({5-oxo-2-[(1,7,7-trimethylbicyclo[2.2.1]hept-2-yl)amino]-1,5-dihydro-4H-imidazol-4-ylidene}methyl)-1H-pyrrolo[2,3-b]pyridin-5-yl]piperidine-4-carboxamide;

(5Z)-N-(3-{[2-(1-azabicyclo[2.2.2]oct-3-ylamino)-5-oxo-1,5-dihydro-4H-imidazo-4-ylidene]methyl}-1H-pyrrolo[2,3-b]pyridin-5-yl)-1-methylpiperidine-4-carboxamide;

(5Z)-1-methyl-N-[3-({5-oxo-2-[(1-phenyl-2-pyrrolidin-1-ylethyl)amino]-1,5-dihydro-4H-imidazol-4-ylidene}methyl)-1H-pyrrolo[2,3-b]pyridin-5-yl]piperidine-4-carboxamide;

(5Z)-N₁-(3-{([2-benzylamino)-5-oxo-1,5-dihydro-4H-imidazol-4-ylidene]methyl}-1H-pyrrolo[2,3-b]pyridin-5-yl)-N₃,N₃-dimethyl-beta-alaninamide;

(5Z)-N₃, N₃-dimethyl-N₁-{3-({5-oxo-2-[(1-phenylethyl)amino]-1,5-dihydro-4H-imidazol-4-ylidene 3 methyl)-1H-pyrrolo[2,3-b]pyridin-5-yl]-beta-alaninamide;

(5Z)-N₁-{[2-(cyclohexylamino)-5-oxo-1,5-dihydro-4H-imidazol-4-ylidene]methyl-3-1H-pyrrolo[2,3-b]pyridin-5-yl)-N₃, N₃-dimethyl-beta-alaninamide;

(5Z)-N-(3-{[2-(bicyclo[2.2.1]hept-2-ylamino)-5-oxo-1,5-dihydro-4H-imidazol-4-ylidene]methyl}-1H-pyrrolo[2,3-b]pyridin-5-yl)-N₃, N₃-dimethyl-beta-alaninamide;

(5Z)-N-(3-{[2-(1-azabicyclo[2.2.2]oct-3-ylamino)-5-oxo-1,5-dihydro-4H-imidazol-4-ylidene]methyl}-1H-pyrrolo[2,3-b]pyridin-5-yl)butanamide;

(5Z)-N-(3-([2-(benzylamino)-5-oxo-1,5-dihydro-4H-imidazol-4-ylidene]methyl}-1H-pyrrolo[2,3-b]pyridin-5-yl)-3-(4-methylpiperazin-1-yl)benzamide;

(5Z)-3-(4-methylpiperazin-1-yl)-N-[3-({5-oxo-2-[(1-phenylethyl)amino]-1,5-dihydro-4H-imidazol-4-ylidene}methyl)-1H-pyrrolo[2,3-b]pyridin-5-yl]benzamide;

(5Z)-N-(3-{[2-(cyclohexylamino)-5-oxo-1,5-dihydro-4H-imidazol-4-ylidene]methyl}-1H-pyrrolo[2,3-b]pyridin-5-yl)-3-(4-methylpiperazin-1-yl)benzamide;

(5Z)-N-(3-{[2-(bicyclo[2.2.1]hept-2-ylamino)-5-oxo-1,5-dihydro-4H-imidazol-4-ylidene]methyl}-1H-pyrrolo[2,3-b]pyridin-5-yl)-3-(4-methylpiperazin-1-yl)benzamide;

(5Z)-N-(3-{[2-(1-azabicyclo[2.2.2]oct-3-ylamino)-5-oxo-1,5-dihydro-4H-imidazol-4-ylidene]methyl}-1H-pyrrolo[2,3-b]pyridin-5-yl)-2-methylpropanamide;

(5Z)-N-(3-{[2-(benzylamino)-5-oxo-1,5-dihydro-4H-imidazol-4-ylidene]methyl}-1H-pyrrolo[2,3-b]pyridin-5-yl)-4-(4-methylpiperazin-1-yl)benzamide;

(5Z)-4-(4-methylpiperazin-1-yl)-N-[3-({5-oxo-2-[(1-phenylethyl)amino]-1,5-dihydro-4H-imidazol-4-ylidene}methyl)-1H-pyrrolo[2,3-b]pyridin-5-yl]benzamide;

(5Z)-N-(3-{[2-(cyclohexylamino)-5-oxo-1,5-dihydro-4H-imidazol-4-ylidene]methyl}-1H-pyrrolo[2,3-b]pyridin-5-yl)-4-(4-methylpiperazin-1-yl)benzamide;

(5Z)-N-(3-{[2-(bicyclo[2.2.1]hept-2-ylamino)-5-oxo-1,5-dihydro-4H-imidazol-4-ylidene]methyl}-1H-pyrrolo[2,3-b]pyridin-5-yl)-4-(4-methylpiperazin-1-yl)benzamide;

(5Z)-N-(3-{[2-(1-azabicyclo[2.2.2]oct-3-ylamino)-5-oxo-1,5-dihydro-4H-imidazol-4-ylidene]methyl}-1H-pyrrolo[2,3-b]pyridin-5-yl)-3-methylbutanamide.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids such as nitric, hydrochloric, hydrobromic, sulfuric, perchloric, phosphoric, acetic, trifluoroacetic, propionic, glycolic, lactic, oxalic, malonic, malic, maleic, tartaric, citric, benzoic, cinnamic, mandelic, methanesulphonic, isothionic and salicylic acid.

Certain functional groups contained within the compounds of the present invention can be substituted for bioisosteric groups, that is, groups which have similar spatial or electronic requirements to the parent group, but exhibit differing or improved physicochemical or other properties. Suitable examples are well known to those of skill in the art, and include, but are not limited to moieties described in Patini et al., Chem. Rev, 1996, 96, 3147-3176 and references cited therein.

The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. The compounds of Formula IA or IB may also exist as tautomers. This invention relates to the use of all such tautomers and mixtures thereof.

The subject invention also includes isotopically-labelled compounds, and the pharmaceutically acceptable salts, solvates and prodrugs thereof, which are identical to those recited in Formula IA or IB, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{35}S$, $^{33}P$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula IA or IB of this invention and prodrugs thereof can generally be prepared by carrying out the procedures disclosed in the Schemes and/or in the Examples and Preparations below, by substituting a readily available isotopically labelled reagent for a non-isotopically labelled reagent.

In another embodiment, the present invention is directed to a pharmaceutical composition comprising a therapeutically effective amount of any of the aforementioned embodiments or species in association with at least one pharmaceutically acceptable excipient, carrier or diluent.

A further embodiment of the present invention is directed to a method of treating a disease in a mammal caused by or associated with abnormal cell growth comprising administering to said mammal a therapeutically effective amount of any of the embodiments of the present invention or compounds described herein.

Another embodiment of the present invention is directed to a method of treating a mammal suffering from cancer comprising administering to said mammal an anti-cancer effective amount of an embodiment or species of the present invention described herein.

An additional embodiment is directed to a method of treating a mammal suffering from cell proliferative disorders comprising administering to said mammal an embodiment or species of the present invention described herein in a therapeutically effective amount for treating said cell proliferative disorder.

A further embodiment is directed to a method of treating mammals suffering from the diseases selected from cancer, Alzheimer's disease, neurodegenerative disease, and viral infections, which comprises administering to said mammal an effective amount of an embodiment or species of the present invention described herein to treat said disease.

This invention also encompasses pharmaceutical compositions containing prodrugs of compounds of the Formula IA or IB and methods of treating abnormal cell growth through administering these prodrugs. For example, compounds of Formula IA or IB having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of Formula IA or IB. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

In a preferred embodiment of the method described above, the present invention is directed to the treatment of a mammal, especially human afflicted with a disease or condition caused by and/or associated with an altered protein kinase activity selected from the group consisting of cancer, cell proliferative disorders, Alzheimer's disease, viral infections, auto-immune diseases and neurodegenerative disorders which comprises administering threto an effective amount of a compound of Formula IA or IB.

Specific types of cancer that may be treated according to the invention include lung cancer, including small lung cancer, bone cancer, pancreatic cancer, skin cancer, including squamous cell carcinoma, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the liver, cancer of the gall bladder, hemoatopoietic tumors of lymphoid lineage, such as acute lymphocitic leukemia, acute lymphoblastic leukemia, B-cell lymphoma, T-cell lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia, tumors of mesenchymal origin, including fibrosarcoma and rhabdomyosarcoma; tumors of the central and peripheral nervous system, including astrocytoma, neurobalstoma, glioma and schwannomas; cancer of the bladder, cancer of the kidney or urethra, renal cell carcinoma, carcinoma of the renal pelvis, neoplasms of the central nervous system (CNS), as well as tumors of the peripheral nervous system, such as astocytoma, neruroblastoma, glioma and schwannomas; primary CNS lymphoma, spinal axis tumors, brain stem glioma, pituitary adenoma, other tumors including melanoma, seminoma, tetratocarcinoma, osteosarcoma; xenoderma pigametosyum; Keratoctanthoma; thyroid follicular cancer, Kaposi's sarcoma, or a combination of one or more of the foregoing cancers. In another embodiment, said abnormal cell growth is a benign proliferative disease, including, but not limited to, psoriasis, benign prostatic hypertrophy and restinosis. The compounds of the present invention are especially effective in treating carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderoma pigmentosum, keratoxanthoma, thyroid follicular cancer and Kaposi's sarcoma.

In another preferred embodiment of the method described above, the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis glomerulonephritis and post-surgical stenosis and restenosis. In addition, the object of the present invention, provides tumor angiogenesis and metastasis inhibition. A preferred embodiment is directed to the use of the compounds of the present invention for treating cancer.

This invention also relates to a method for the treatment of abnormal cell growth in a mammal, including a human, comprising administering to said mammal an amount of a compound of the Formula IA or IB, as defined above, or a pharmaceutically acceptable salt, solvate or prodrug thereof, that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said method, said abnormal cell growth is a benign proliferative disease, including, but not limited to, psoriasis, benign prostatic hypertrophy or restenosis.

This invention also relates to a pharmaceutical composition for the treatment of abnormal cell growth in a mammal, including a human, comprising an amount of a compound of the Formula IA or IB, as defined above, or a pharmaceutically acceptable salt, solvate or prodrug thereof, that is effective in treating abnormal cell growth, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

This invention also relates to a method for the treatment of a disorder associated with angiogenesis in a mammal, including a human, comprising administering to said mammal an amount of a compound of the Formula IA or IB, as defined above, or a pharmaceutically acceptable salt, solvate or prodrug thereof, that is effective in treating said disorder. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi*, *Yersinia* spp., *Bordetella pertussis*, and group A *Streptococcus*.

The azaindolylidene derivatives of formula (IA or IB), are obtainable through a synthetic process comprising well known reactions carried out according to conventional techniques, as well as through an extremely versatile parallel synthesis process, being both comprised within the scope of the invention.

A more complete appreciation of the invention and many of the attendant advantages thereof will be readily obtained as the same becomes better understood by reference to the following detailed description.

DETAILED DESCRIPTION OF THE INVENTION

As set forth above, are further objects of the present invention the processes for preparing the compounds of formula (IA or IB) and the pharmaceutically acceptable salts thereof. The compounds can be prepared using art recognized techniques.

The following schemes for preparing the compounds of the present invention is exemplary.

The compounds of the present invention can be prepared as depicted in Schemes I-V hereinbelow.

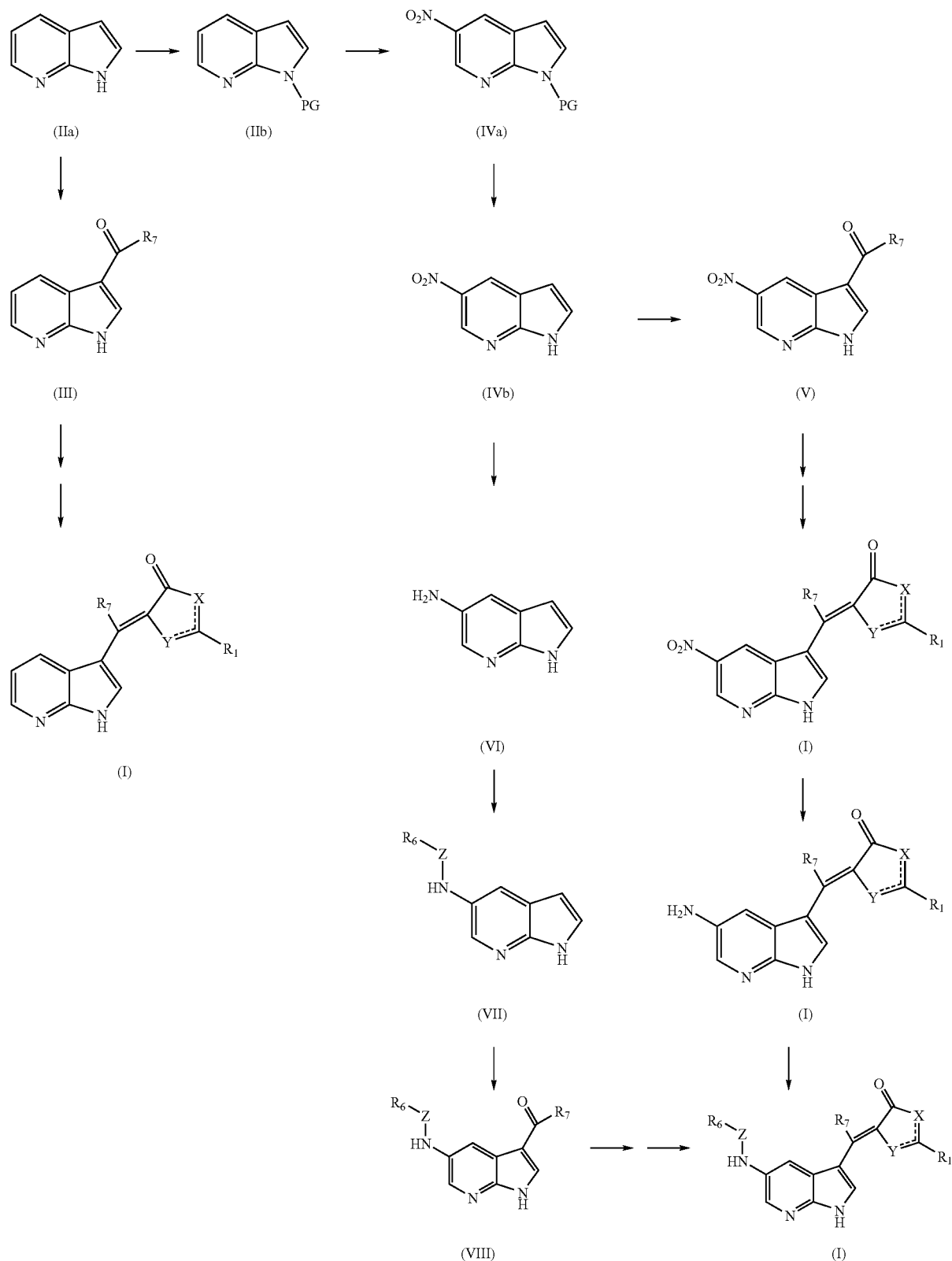
PG = suitable protecting group

In Scheme I, an overview of the synthetic pathways leading to compounds of formula (IB) is shown, where PG is a suitable protecting group, for instance, N-benzenesulphonamide or N-t-butoxycarbonyl (N-Boc).

Acylation of azaindoles (IIa), (IVb) and (VII) was performed, as described in the literature (see, for instance, *J. Med. Chem.* 1972, 15, 149; *J. Het Chem.* 1982, 19, 665), with a formylating agent such as, for instance, hexamethylenetetramine in a solvent such as acetic acid at 33% or phosphorus oxychloride in dimethylformamide, at a temperature ranging from room temperature to reflux or with an acylating agent such as dichloromethylmethylether or acetyl chloride in the presence of a Lewis acid (e.g. aluminum trichloride, titanium tetrachloride and the like), at a temperature ranging from −78° C. to reflux.

Nitration of the conveniently protected azaindole of formula (IIb) was carried out by means of a nitrating agent, such as, for instance, trifluoroacetyinitrate with a procedure already reported in a previous patent where it was applied to different azaindole derivatives, described and claimed in our still unpublished patent application UK 0330043.1, filed in Dec. 24, 2003.

Reduction of the nitro group can be obtained by means of well known methods, for instance either by chemical or catalytic procedures, while amino group acylation is carried out by reaction with different acylating agents, for example, with carboxylic acids or their derivatives, such as acyl chlorides and bromides, with sulphonic acid derivatives, namely sulphonylchlorides and bromides, or with isocyanates and, for instance, chloroformates, to yield respectively carboxamido derivatives, sulphonamido derivatives, ureido derivatives and carbamates. The 5-aminoazaindole derivatives are alternatively reacted under reductive conditions with an aldehyde so as to obtain the corresponding 5-amines.

Scheme II

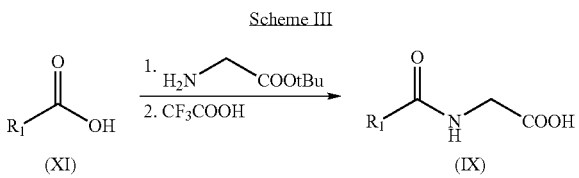

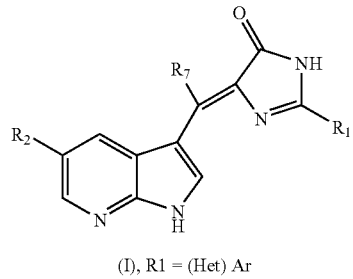

(I), R1 = (Het) Ar

In Scheme II the preparation of a compound of formula (IB), wherein $R_1$ is an optionally substituted aryl or heteroaryl is outlined. The procedure, according to the process of the invention, is carried out according to conventional techniques (see, for instance, *J. Am. Chem. Soc.* 1946, 647) by reacting the above compounds of formula (III), (V) or (VIII) with an hyppuric acid derivative of formula (IX), for instance in acetic anhydride in the presence of a suitable base such as sodium acetate, at a temperature ranging from about RT to 140° C. for a suitable time, i.e. from about 1 hour to several hours. Always in Scheme II the transformation of a compound of formula (X) to a compound of formula (IB) is performed according to conventional techniques by reaction with ammonia in the presence of a suitable base such as sodium carbonate, at a temperature ranging from about 60° C. to 140° C. for a suitable time, i.e. from about 1 hour to several hours.

Scheme III $$R_1\underset{(XI)}{\overset{O}{\underset{\|}{C}}}\!\!OH \xrightarrow[2.\ CF_3COOH]{1.\ H_2N\!\!\smile\!\!COOtBu} R_1\underset{(IX)}{\overset{O}{\underset{\|}{C}}}\!\!N\!\!\smile\!\!COOH$$

In Scheme III the preparation of the required hyppuric acid derivatives of formula (IX) from the corresponding carboxylic acids of formula (XI) is reported.

The reaction between glycine t-butylester and a carboxylic acid of formula (XI) can be carried out in the presence of a coupling agent such as, for instance, carbodiimide, 1,3-dicyclohexylcarbodiimide, 1,3-diisopropylcarbodiimide, O-(benzotriazol-1-yl)-N,N,N',N'-tetramethyluronium tetrafluoborate, 1-(3-dimethylaminopropyl)-3-ethylcarbodiimide, N-cyclohexylcarbodiimide-N'-propyloxymethyl polystyrene or N-cyclohexylcarbodiimide-N'-methyl polystyrene, in a suitable solvent such as, for instance, dichloromethane, chloroform, tetrahydrofuran, diethyl ether, 1,4-dioxane, acetonitrile, toluene, or N,N-dimethylformamide at a temperature ranging from about −20° C. to reflux for a suitable time, i.e. from about 30 min. to about 96 hours, optionally in the presence of a suitable catalyst such as 4-dimethylaminopyridine or in the presence of a further coupling reagent such as N-hydroxybenzotriazole.

The reaction between glycine t-butylester and a carboxylic acid of formula (XI) can be also carried out, for example, by a mixed anhydride method, using an alkyl chloroformate, such as ethyl, iso-butyl, or iso-propyl chloroformate, in the presence of a tertiary base, such as triethylamine, N,N- diisopropylethylamine or pyridine, in a suitable solvent such as, for instance, toluene, dichloromethane, chloroform, tetrahydrofuran, acetonitrile, diethyl ether, 1,4-dioxane, or N,N-dimethylformamide, at a temperature ranging from about −30° C. to room temperature. Hydrolysis of the intermediate hyppuric derivative t-butyl ester is carried out, for example, in acidic medium, by means of trifluoroacetic acid or hydrochloric acid at a temperature ranging from about −30° C. to 80° C.

Lewis acid, such as, for example, borontrifluoride-diethylether complex at a temperature ranging from about −78° C. to room temperature for a suitable time, i.e. from about 1 hour to one day. The obtained azaindolylidene derivative of formula (XIII) can be elaborated in different ways in order to obtain the desired compounds of formula (IB): treated directly with a suitable amine of formula (XIV) in a convenient solvent such as, for instance, ethanol, tetrahydrofuran, 1,4-dioxane, acetonitrile, or N,N-dimethylformamide at

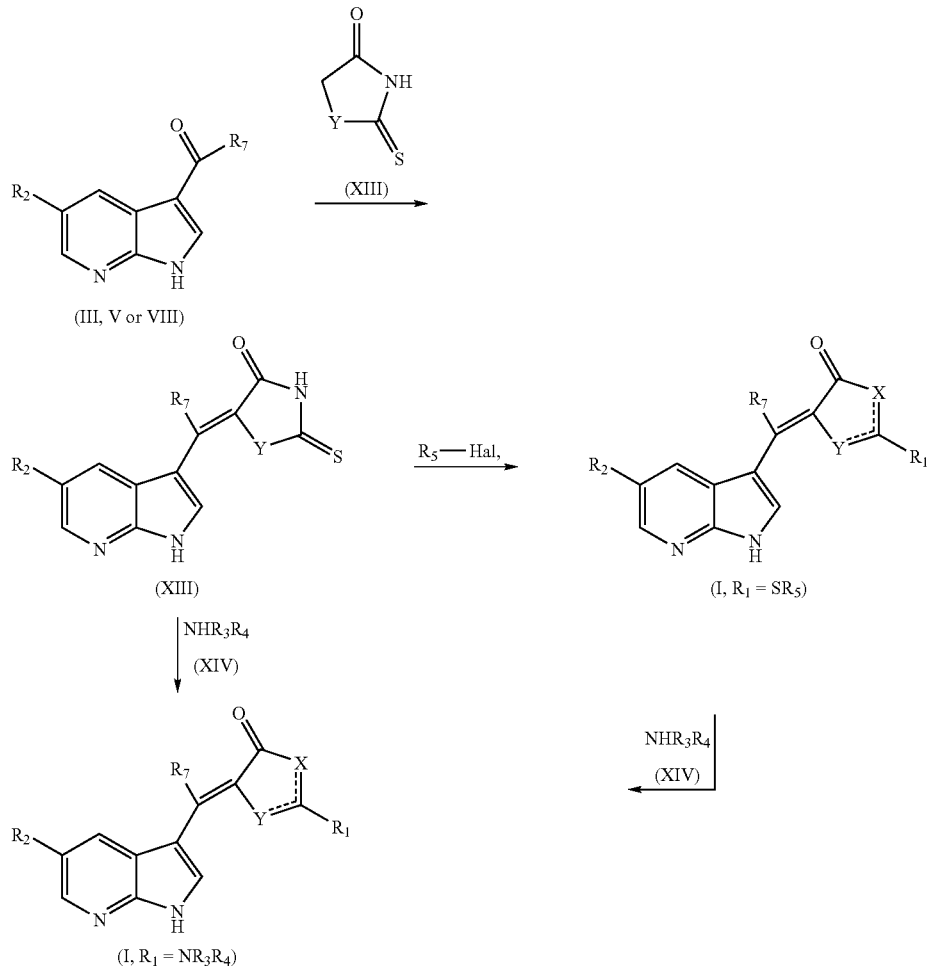

In Scheme IV the preparation of compounds of formula (IB), where $R_1$ is $SR_5$ or $NR_3R_4$, is reported. Condensation of an azaindole derivative of Formula III, V, or VIII with a molecule of formula (XII), such as 2-thiohydantoin (Y=NH), rhodanine (Y=S) or 1-methyl-2-thioxoimidazolidin-4-one (Y=NMe), is carried out according to conventional techniques (see, for instance, *Phosphorus, Sulfur and Silicon* 1998, 140, 159). When $R_7$ is a hydrogen atom the reaction can be, for instance, carried out in glacial acetic acid in the presence of a suitable base such as sodium acetate, at a temperature ranging from about RT to 140° C. for a suitable time, i.e. from about 1 hour to several hours.

When $R_7$ is alkyl, for instance, methyl, the reaction is performed in a suitable solvent (such as THF or DMF) in the presence of a base like, for example, triethylamine and a a temperature ranging from about 50° C. to reflux for a suitable time, i.e. from about 30 min. to about 18 hours, or, alternatively, alkylated to the enolthioether of formula (IB) with an alkylating agent such as an alkylhalide ($R_5$-Hal), for example, methyl iodide, ethyl iodide, benzyl bromide and the like in basic medium, for instance sodium or potassium hydroxide aqueous solution, at temperatures ranging from 0° C. to room temperature and for a suitable time, i.e. from about 1 hour to several hours. In this way compounds of formula (IB) where $R_1$ is a S—$R_5$ group are directly obtained. When needed, the intermediate enolthioether of formula (IB) is reacted with a suitable amine of formula (XIV) in a convenient solvent such as, for instance, ethanol, tetrahydrofuran, 1,4-dioxane, acetonitrile, or N,N-dimethylformamide at a temperature ranging from about 50° C. to reflux for a suitable time, i.e. from about 30 min. to about 18 hours.

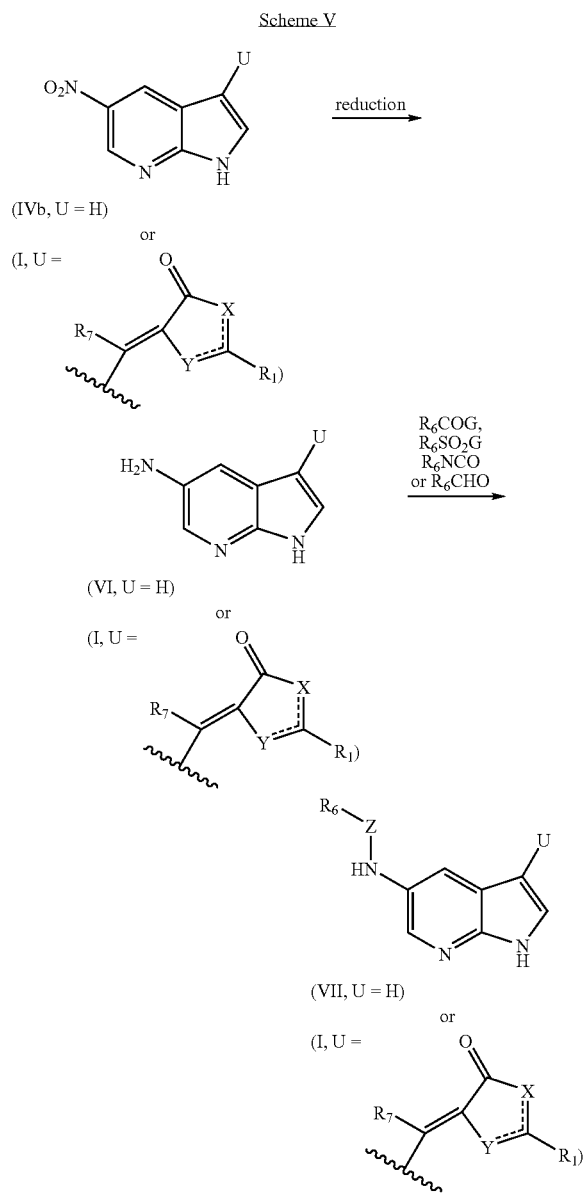

Scheme V

In Scheme V, step one, the starting nitro derivatives of formula (IB) or (IVb) are subdued to reduction of the nitro group, by means of well known methods, such as, for instance, chemical reduction with iron, zinc or tin (II) chloride treatment. The reaction may occur in a suitable solvent such as, for instance, N,N-dimethylformamide, 1,4-dioxane, ethanol/water, methanol/water, 1-methyl-2-pyrrolidinone or acetonitrile, at a temperature ranging from about −10° C. to reflux and for a suitable time, for instance from about 30 minutes to about 96 hours.

The said reduction may be also performed as a catalytic hydrogenation or by hydrogen transfer, according to conventional techniques, in the presence of a suitable catalyst such as, for instance, palladium on charcoal.

In step two acylation of the amino group of derivatives of formula (IB) or (VI) occurs by reacting with carboxylic acids or their derivatives, such as acyl chlorides and bromides, with sulphonic acid derivatives, namely sulphonyl chlorides and bromides, with isocyanates or with chloroformates to yield respectively carboxamido derivatives, sulphonamido derivatives, ureido derivatives and carbamates.

The reaction between the 5-aminoazaindole derivatives and a carboxylic acid can be carried out in the presence of a coupling agent such as, for instance, benzotriazol-1-yloxytris(pyrrolidino)phosphonium hexafluorophosphate, 1,3-dicyclohexylcarbodiimide, bromo-tris-pyrrolidino-phosphonium hexafluorophosphate, 1,3-diisopropylcarbodiimide, o-benzotriazol-1-yl-N,N,N',N'-tetramethyluronium tetrafluoroborate, 1-(3-dimethylaminopropyl)-3-ethylcarbodiimide, N-[(1H-1,2,3-benzotriazol-1-yloxy)(dimethylamino)methylene]-N-methylmethanaminium tetrafluoroborate, N-cyclohexylcarbodiimide-N'-propyloxymethyl polystyrene or N-cyclohexylcarbodiimide-N'-methyl polystyrene, in a suitable solvent such as, for instance, dichloromethane, chloroform, tetrahydrofuran, diethyl ether, 1,4-dioxane, acetonitrile, toluene or N,N-dimethylformamide, at a temperature ranging from about −10° C. to reflux and for a suitable time ranging from about 30 minutes to about 96 hours.

The said reaction is optionally carried out in the presence of a suitable catalyst, for instance 4-dimethylaminopyridine, or in the presence of a further coupling agent, such as N-hydroxybenzotriazole. The reaction can also be carried out through a mixed anhydride method, that is by using an alkyl chloroformate such as ethyl, isobutyl, or isopropyl chloroformate, in the presence of a tertiary base such as triethylamine, N,N-diisopropylethylamine or pyridine, in a suitable solvent such as toluene, dichloromethane, chloroform, tetrahydrofuran, acetonitrile, diethyl ether, 1,4-dioxane or N,N-dimethylformamide, and at a temperature ranging from about −30° C. to room temperature.

The reaction between 5-aminoazaindole derivatives and an acylchloride or acylbromide can be carried out in the presence of a tertiary base such as triethylamine, N,N-diisopropylethylamine or pyridine, in a suitable solvent such as toluene, dichloromethane, chloroform, diethyl ether, tetrahydrofuran, acetonitrile or N,N-dimethylformamide, and at a temperature ranging from about −10° C. to reflux. The reaction between 5-aminoazaindole derivatives and a sulphonyl derivative, such as the chloride or the bromide, can be carried out in the presence of a tertiary base such as triethylamine, N,N-diisopropylethylamine or pyridine, in a suitable solvent such as toluene, dichloromethane, chloroform, diethyl ether, tetrahydrofuran, acetonitrile or N,N-dimethylformamide, at a temperature ranging from about −10° C. to reflux.

Finally, the reaction between 5-aminoazaindole derivatives and an isocyanate or a chloroformate can be carried out in the presence of a tertiary base such as triethylamine, N,N-diisopropylethylamine or pyridine, in a suitable solvent such as toluene, dichloromethane, chloroform, diethyl ether, tetrahydrofuran, acetonitrile, or N,N-dimethylformamide, and at a temperature ranging from about −10° C. to reflux.

In addition ureido derivatives and carbamates may be prepared by reacting 5-aminoazaindole derivatives with a suitable acylating agent, for instance triphosgene or trichloromethyl chloroformate, and then with a convenient amine or alcohol, according to conventional techniques. The said reaction is carried out in a suitable solvent such as, for instance, dichloromethane, chloroform, toluene, tetrahydrofuran or dioxane, optionally in the presence of a tertiary base, for instance triethylamine, and of a catalyst such as 4-dimethylaminopyridine, at a temperature ranging from about −10° C. to room temperature and for a time varying from about 30 minutes to about 96 hours.

With respect to the compounds of the present invention having asymmetric carbon atoms, diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention. It is preferred that the compounds of Formula IA or IB are substantially pure, eg, contain less than about 25% impurities, and more preferably less than about 15% impurity and even more preferably, less than about 10% impurity and most preferably less than about 5% impurity and especially most preferably, less than about 1% impurity.

In the most preferred embodiments, the compound is of Formula IB, which is substantially pure, as defined herein and is substantially free of the isomer of Formula IA.

Although not depicted herein, compounds of Formula IA are also formed by the above-identified processes. For example, the reaction of III, V, or VIII with a compound of Formula IX also forms a compound corresponding to the compound of Formula X, but in the E configuration, which is then reacted with base, such as $NH_4OH$ or $Na_2CO_3$ to form the corresponding derivative of a compound of Formula IA. Similarly, in Scheme IV, the reaction of III, V, or VIII with XII forms a compound corresponding to compound XIII, but in the E configuration, which then undergoes the transformations depicted therein to form the corresponding IA derivative. Finally, the compounds corresponding to IV in the E configuration or IA can undergo the reactions depicted in the Scheme V.

However, the IA and IB compounds can be separated into their separate isomers at the end of the reaction by techniques known in the art, e.g., column chromatography. Moreover, it is to be noted that the various Z or E derivatives can be separated into their respective diasteromers at earlier steps in the process, such as after the reaction of IX with III, V or VIII in Scheme II or after the reaction of III, V or VIII with VII in Scheme IV. Moreover, the reaction depicted in Scheme V may be conducted with either the Z or E isomers or with a mixture of the Z and E isomers.

The compounds of Formula IA or IB that are basic in nature are capable of forming a wide variety of different salts with various inorganic and organic acids. Although such salts must be pharmaceutically acceptable for administration to animals, it is often desirable in practice to initially isolate the compound of Formula IA or IB from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of Formula IA or IB that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of Formula IA or IB. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product. Since a single compound of the present invention may include more than one acidic or basic moieties, the compounds of the present invention may include mono, di or tri-salts in a single compound.

The compounds of the present invention are also useful in the treatment of additional disorders in which aberrant expression ligand/receptor interactions or activation or signaling events related to various protein tyrosine kinases, are involved. Such disorders may include those of neuronal, glial, astrocytal, hypothalamic, and other glandular, macrophagal, epithelial, stromal, and blastocoelic nature in which aberrant function, expression, activation or signaling of the erbB tyrosine kinases are involved. In addition, the compounds of the present invention may have therapeutic utility in inflammatory, angiogenic and immunologic disorders involving both identified and as yet unidentified tyrosine kinases that are inhibited by the compounds of the present invention.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

For example, the solid oral forms may contain, together with the active compound, diluents, e.g. lactose, dextrose, saccharose, sucrose, cellulose, corn starch or potato starch; lubricants, e.g. silica, talc, stearic, magnesium or calcium stearate, and/or polyethylene glycols; binding agents, e.g. starches, arabic gum, gelatin, methylcellulose, carboxymethylcellulose or polyvinyl pyrrolidone; disaggregating agents, e.g. a starch, alginic, alginates or sodium starch glycolate; effervescing mixtures; dyestuffs; sweeteners; wetting agents such as lecithin, polysorbates, laurylsulfates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerin and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain as carrier, for example, sterile water or preferably they may be in the form of sterile, aqueous, isotonic saline solutions or they may contain as a carrier propylene glycol.

The suppositories may contain together with the active compound a pharmaceutically acceptable carrier, e.g. cocoa butter, polyethylene glycol, a polyoxyethylene sorbitan fatty ester surfactant or lecithin.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

Pharmacology

The compounds of Formula IA or IB are active as protein kinase inhibitors and are therefore useful, for instance, to restrict the unregulated proliferation of tumor cells.

In therapy, they may be used in the treatment of various tumors such as, for instance, carcinomas, e.g. mammary carcinoma, lung carcinoma, bladder carcinoma, colon carcinoma, ovary and endometrial tumors, sarcomas, e.g. soft tissue and bone sarcomas, and the hematological malignancies such as, e.g., leukemias.

In addition, the compounds of Formula IA or IB are also useful in the treatment of other cell proliferative disorders such as psoriasis, vascular smooth cell proliferation associated with atherosclerosis and post-surgical stenosis and restenosis and in the treatment of Alzheimer's disease.

The inhibiting activity of putative protein kinase inhibitors and the potency of selected compounds was determined through a method of assay based on the use of the Multi-Screen-PH plates (Millipore), in which a phosphocellulose filter paper was placed at each well bottom allowing binding of positive charged substrate after a washing/filtration step.

When a radioactivity labeled phosphate moiety was transferred by the ser/threo kinase to the filter-bound protein substrate, light emitted was measured in a scintillation counter.

Inhibition Assay of Cdc7 Activity

The inhibiting activity of putative Cdc7 inhibitors and the potency of selected compounds is determined through a method of assay based on the use of Dowex resin capture technology.

The assay consists of the transfer of radioactivity labeled phosphate moiety by the kinase to an acceptor substrate. The resulting 33P-labeled product is separated from unreacted tracer, transferred into a scintillation cocktail and light emitted is measured in a scintillation counter.

The inhibition assay of Cdc7/Dbf4 activity is performed according to the following protocol. The MCM2 substrate is trans-phosphorylated by the Cdc7/Dbf4 complex in the presence of ATP traced with $\gamma^{33}$-ATP. The reaction is stopped by addition of Dowex resin in the presence of formic acid. Dowex resin particles capture unreacted $\gamma^{33}$-ATP and drag it to the bottom of the well while $^{33}P$ phosphorylated MCM2 substrate remains in solution. The supernatant is collected, transferred into Optiplate plates and the extent of substrate phosphorylation is evaluated by β counting.

The inhibition assay of Cdc7/Dbf4 activity was performed in 96 wells plate according to the following protocol.

To each well of the plate were added:

10 µl test compound (10 increasing concentrations in the nM to uM range to generate a dose-response curve). The solvent for test compounds contained 3% DMSO. (final concentration 1%)

10 µl substrate MCM2 (6 nM final concentration), a mixture of cold ATP (2 µM final concentration) and radioactive ATP (1/5000 molar ratio with cold ATP).

10 µl enzyme (Cdc7/Dbf4, 2 nM final concentration) that started the reaction. The buffer of the reaction consisted in 50 mM HEPES pH 7.9 containing 15 mM $MgCl_2$, 2 mM DTT, 3 uM $NaVO_3$, 2 mM glycerophosphate and 0.2 mg/ml BSA.

After incubation for 60 minutes at room temperature, the reaction was stopped by adding to each well 150 µl of Dowex resin in the presence of 150 mM formic acid. After another 60 min incubation, 50 µL of suspension were withdrawn and transferred into 96-well OPTIPLATEs containing 150 µl of MicroScint 40 (Packard); after 5-10 minutes shaking the plates were read for 1 min in a Packard TOP-Count radioactivity reader.

IC50 determination: inhibitors were tested at different concentrations ranging from 0.0005 to 10 µM. Experimental data were analyzed by the computer program Assay Explorer using the four parameter logistic equation:

$$y=\text{bottom}+(\text{top}-\text{bottom})/(1+10^{\wedge}((\log IC50-x)*\text{slope}))$$

where x is the logarithm of the inhibitor concentration, y is the response; y starts at bottom and goes to top with a sigmoid shape.

In addition the selected compounds have been characterized for specificity on Cdk2A, on a panel of ser/threo kinases strictly related to cell cycle (cdk2/cyclin E, cdk1/cyclin B1, cdk4/Cyclin D1, cdk5/p25), on IGF1-R, Aurora-2, AKT1.

Inhibition Assay of Cdk2/Cyclin A Activity

Kinase reaction: 1.5 µM histone H1 substrate, 25 µM ATP (0.2 µCi P33µ-ATP), 30 ng of baculovirus co-expressed Cdk2/Cyclin A, 10 µM inhibitor in a final volume of 100 µl buffer (TRIS HCl 10 mM pH 7.5, $MgCl_2$ 10 mM, 7.5 mM DTT) were added to each well of a 96 U bottom well plate. After 10 min at 37° C. incubation, reaction was stopped by 20 µl EDTA 120 mM.

Capture: 100 µl were transferred from each well to MultiScreen plate, to allow substrate binding to phosphocellulose filter. Plates were then washed 3 times with 150 µl/well PBS Ca++/Mg++ free and filtered by MultiScreen filtration system.

Detection: filters were allowed to dry at 37° C., then 100 µl/well scintillant were added and 33P labeled histone H1 was detected by radioactivity counting in the Top-Count instrument.

Results: data were analyzed and expressed as % inhibition referred to total activity of enzyme (=100%).

All compounds showing inhibition ≧50% were further analyzed in order to study and define potency (IC50) as well as the kinetic-profile of inhibitor through Ki calculation.

IC50 determination: the protocol used was the same described above, where inhibitors were tested at different concentrations ranging from 0.0045 to 10 µM. Experimental data were analyzed by the computer program GraphPad Prizm using the four parameter logistic equation:

$$y=\text{bottom}+(\text{top}-\text{bottom})/(1+10^{\wedge}((\log IC50-x)*\text{slope}))$$

where x is the logarithm of the inhibitor concentration, y is the response; y starts at bottom and goes to top with a sigmoid shape.

Ki calculation: either the concentration of ATP and histone H1 substrate were varied: 4, 8, 12, 24, 48 µM for ATP (containing proportionally diluted $P^{33}$µ-ATP) and 0.4, 0.8, 1.2, 2.4, 4.8 µM for histone were used in absence and presence of two different, properly chosen inhibitor concentrations.

Experimental data were analyzed by the computer program "SigmaPlot" for Ki determination, using a random bireactant system equation:

$$v = \frac{V\max \frac{(A)(B)}{aKAKB}}{1 + \frac{(A)}{KA} + \frac{(B)}{KB} + \frac{(A)(B)}{aKAKB}}$$

where A=ATP and B=histone H1.

Inhibition Assay of Cdk2/Cyclin E Activity

Kinase reaction: 1.5 µM histone H1 (Sigma #H-5505) substrate, 25 µM ATP (0.2 µCi $P^{33}γ$-ATP), 15 ng of baculovirus co-expressed cdk2/GST-Cyclin E, suitable concentrations of inhibitor in a final volume of 100 µl buffer (TRIS HCl 10 mM pH 7.5, $MgCl_2$ 10 mM, 7.5 mM DTT+0.2 mg/ml BSA) were added to each well of a 96 U bottom well plate. After 10 min at 37° C. incubation, reaction was stopped by 20 µl EDTA 120 mM.

Capture: 100 µl were transferred from each well to MultiScreen plate, to allow substrate binding to phosphocellulose filter. Plates were then washed 3 times with 150 µl/well PBS $Ca^{++}$/$Mg^{++}$ free and filtered by MultiScreen filtration system.

Detection: filters were allowed to dry at 37° C., then 100 µl/well scintillant were added and $^{33}P$ labeled histone H1 was detected by radioactivity counting in the Top-Count instrument.

Inhibition Assay of Cdk1/Cyclin B1 Activity

Kinase reaction: 1.5 µM histone H1 (Sigma #H-5505) substrate, 25 µM ATP (0.2 µCi $P^{33}γ$-ATP), 30 ng of baculovirus co-expressed cdk1/Cyclin B1, suitable concentrations of inhibitor in a final volume of 100 µl buffer (TRIS HCl 10 mM pH 7.5, $MgCl_2$ 10 mM, 7.5 mM DTT+0.2 mg/ml BSA) were added to each well of a 96 U bottom well plate. After 10 min at 37° C. incubation, reaction was stopped by 20 µl EDTA 120 mM.

Capture: 100 µl were transferred from each well to MultiScreen plate, to allow substrate binding to phosphocellulose filter. Plates were then washed 3 times with 150 µl/well PBS $Ca^{++}$/$Mg^{++}$ free and filtered by MultiScreen filtration system.

Detection: filters were allowed to dry at 37° C., then 100 µl/well scintillant were added and $^{33}P$ labeled histone H1 was detected by radioactivity counting in the Top-Count instrument.

Inhibition Assay Cdk4/Cyclin D1 Activity

Kinase reaction: 0.4 µM mouse GST-Rb (769-921) (#sc-4112 from Santa Cruz) substrate, 10 µM ATP (0.5 µCi $P^{33}γ$-ATP), 100 ng of baculovirus expressed GST-cdk4/GST-Cyclin D1, suitable concentrations of inhibitor in a final volume of 50 ul buffer (TRIS HCl 10 mM pH 7.5, MgCl$_2$ 10 mM, 7.5 mM DTT+0.2 mg/ml BSA) were added to each well of a 96 U bottom well plate. After 40 min at 37° C. incubation, reaction was stopped by 20 µl EDTA 120 mM.

Capture: 60 µl were transferred from each well to MultiScreen plate, to allow substrate binding to phosphocellulose filter. Plates were then washed 3 times with 150 ul/well PBS Ca$^{++}$/Mg$^{++}$ free and filtered by MultiScreen filtration system.

Detection: filters were allowed to dry at 37° C., then 100 µl/well scintillant were added and $^{33}$P labeled Rb fragment was detected by radioactivity counting in the Top-Count instrument.

Inhibition Assay of Cdk5/p25 Activity

The inhibition assay of cdk5/p25 activity was performed according to the following protocol.

Kinase reaction: 1.0 µM biotinylated histone peptide substrate, 0.25 µCi P33g-ATP, 4 nM cdk5/p25 complex, 0-100 µM inhibitor in a final volume of 100 µl buffer (Hepes 20 mM pH 7.5, MgCl$_2$ 15 mM, 1 mM DTT) were added to each well of a 96 U bottom well plate. After 20 min at 37° C. incubation, the reaction was stopped by the addition of 500 µg SPA beads in phosphate-buffered saline containing 0.1% Triton X-100, 50 µM ATP and 5 mM EDTA. The beads were allowed to settle, and the radioactivity incorporated in the 33P-labelled peptide was detected in a Top Count scintillation counter.

Results: Data were analyzed and expressed as % Inhibition using the formula:

100×(1−(Unknown−Bkgd)/(Enz. Control−Bkgd))

IC50 values were calculated using a variation of the four parameter logistics equation:

$Y=100/[1+10^{((\log EC50-X)*\text{Slope})}]$

Where X=log(µM) and Y=% Inhibition.

Inhibition Assay of IGF1-R Activity

The inhibition assay of IGF1-R activity was performed according to the following protocol.

Kinase reaction: 10 µM biotinylated MBP (Sigma cat. #M-1891) substrate, 0-20 µM inhibitor, 6 µM cold ATP, 2 nM $^{33}$P-ATP, and 22.5 ng IGF1-R (pre-incubated for 30 min at room temperature with cold 60 µM cold ATP) in a final volume of 30 µl buffer (50 mM HEPES pH 7.9, 3 mM MnCl$_2$, 1 mM DTT, 3 µM NaVO$_3$) were added to each well of a 96 U bottom well plate. After incubation for 35 min at room temperature, the reaction was stopped by addition of 100 µl PBS buffer containing 32 mM EDTA, 500 µM cold ATP, 0.1% Triton X100 and 10 mg/ml streptavidin coated SPA beads. After 15 min incubation, 110 µL of suspension were withdrawn and transferred into 96-well OPTI PLATEs containing 100 µl of 5M CsCl. After 4 hours, the plates were read for 2 min in a Packard TOP-Count radioactivity reader.

Results: Experimental data were analyzed with the program GraphPad Prizm.

Inhibition Assay of Aurora-2 Activity

The inhibiting activity and the potency of selected compounds was determined through a method of assay based on the use of the streptavidin scintillation proximity assay beads (amershampharmacia biotech) run in a 96 well plates. At the end of the reaction, the biotinylated peptide substrate was captured with the beads and subsequently allowed to stratify using CsCl$_2$.

When a radioactivity labeled phosphate moiety was transferred by the kinase to the beads-bound peptide, light emitted was measured in a scintillation counter.

The inhibition assay of Aurora-2 activity was performed in 96 wells plate according to the following protocol.

Kinase reaction: 8 µM biotinylated peptide (4 repeats of LRRWSLG), 10 µM ATP (0.5 uCi P$^{33}$g-ATP), 10 nM Aurora2, 10 µM inhibitor in a final volume of 60 µl buffer (HEPES 50 mM pH 7.0, MgCl$_2$ 10 mM, 1 mM DTT, 0.125 mg/ml BSA, 3 µM orthovanadate) were added to each well of a 96 U bottom well plate. After 30 minutes at room temperature incubation, reaction was stopped and biotinylated peptide captured by adding 100 µl of bead suspension.

Stratification: 100 µl of CsCl2 7.5 M were added to each well and let stand one hour before radioactivity was counted in the Top-Count instrument.

Results: data were analyzed and expressed as % inhibition referred to total activity of enzyme (=100%).

All compounds showing inhibition ≧60% were further analyzed in order to study the potency of the inhibitor through IC50 calculation.

The protocol used was the same described above, except that serial dilution of the inhibitor was used. Experimental data were fitted by nonlinear regression using the following equation:

$$v = v_0 + \frac{(v_0 - v_b)}{1 + 10^{n(\log IC_{50} - \log[I])}}$$

With $v_b$ as the baseline velocity, v as the observed reaction velocity, $v_o$ as the velocity in the absence of inhibitors, and [I] as the inhibitor concentration.

Inhibition Assay of AKT-1 Activity

Test compounds are prepared as a 10 mM solution in 100% DMSO and distributed into 96 well plates:

i—for % inhibition studies, individual dilution plates at 1 mM, 100 µM and 10 µM are prepared in 100% DMSO, then diluted at a 3× concentration (30, 3 and 0.3 µM) in ddH$_2$O, 3% DMSO. A Multimek 96 (Beckman) is used for compound pipetting into test plates.

ii—for IC50 determination, compounds are diluted to 1 mM in 100% DMSO and plated into the first column of a microtiter plate (A1 to G1), 100 µl. Well H1 is left empty for the internal standard.

A Biomek 2000 (Beckman) is used for serial 1:3 dilutions in water, 3% DMSO, from column A1 to A10 and for all the 7 compounds in the plate. In a standard experiment, the highest concentration of all compounds is 30 µM that is diluted in the final test mixture at 10 µM.

Columns 11 and 12 are left available for total activity reference and background evaluation.

Assay scheme: U bottom test plates are prepared either with 10 µl of the compound dilution (3×) per well, or 3% DMSO/water, and then placed onto a PlateTrak robotized station (Packard) together with one reservoir for the Enzyme mix (3×) and one for the ATP mix (3×).

As the test starts, the robot (PlateTrak system, Perkin Elmer) takes 10 µl of ATP mix, makes an air gap inside the tips (10 µl) and aspirates 10 µl of Enzyme mix. The following dispensation into the plates allows the kinase reaction to start upon 3 cycles of mixing done by the robot itself.

At this point, the correct concentration is restored for all reagents.

The robot incubates the plates for 60 minutes at room temperature, and then stops the reaction by pipetting 150 µl of Dowex resin into the reaction mix. It is essential to keep the resin well stirred before addition to the plates.

The resin is left another 60 minutes to settle down; the robot then takes 50 µl of supernatant from each well and dispenses them into an Optiplate (Packard) with 150 µl of Microscint 40 (Packard).

Counting: Optiplates, covered by a plastic film to avoid radioactive spilling, are then mixed 10 minutes before counting in a Packard Top Count.

EXAMPLES

The following examples are herewith intended to better illustrate the present invention without posing any limitation to it.

General Methods

Flash chromatography was performed on silica gel (Merck grade 9385, 60 Å). HPLC/MS was performed on a Waters X Terra RP 18 (4.6×50 mm, 3.5 µm) column using a Waters 2790 HPLC system equipped with a 996 Waters PDA detector and a Micromass mod. ZQ single quadrupole mass spectrometer, equipped with an electrospray (ESI) ion source. Mobile phase A was ammonium acetate 5 mM buffer (pH 5.5 with acetic acid/acetonitrile 95:5), and Mobile phase B was $H_2O$/acetonitrile (5:95). Gradient from 10 to 90% B in 8 minutes, hold 90% B 2 min. UV detection at 220 nm and 254 nm. Flow rate 1 ml/min. Injection volume 10 µl. Full scan, mass range from 100 to 800 amu. Capillary voltage was 2.5 KV; Source temp.was 120° C.; Cone was 10 V. Retention Times (HPLC r.t.) are given in minutes at 220 nm or 254 nm. Mass are given as m/z ratio.

When necessary compounds have been purified by Preparative HPLC on a Waters Symmetry C18 (19×50 mm, 5 um) column using a Waters preparative HPLC 600 equipped with a 996 Waters PDA detector and a Micromass mod. ZMD single quadrupole mass spectrometer, electrospray ionisation, positive mode. Mobile phase A was water 0.01% TFA, and Mobile phase B was acetonitrile. Gradient from 10 to 90% B in 8 min, hold 90% B 2 min. Flow rate 20 ml/m.

$^1$H-NMR spectroscopy was performed on a Mercury VX 400 operating at 400.45 MHz equipped with a 5 mm double resonance probe (1H {15N-31P} ID_PFG Varian).

Example 1

(5E+5Z)-2-phenyl-5-(1H-pyrrolo[2,3-b]pyridin-3-ylmethylene)-3,5-dihydro-4H-imidazol-4-one A mixture of azaindole-3-carboxaldehyde (0.5 g, 3.4 mmol), (see *J. Med. Chem.* 1972, 15,149), hyppuric acid (0.61 g, 3.4 mmol) and sodium acetate trihydrate (0.47 g, 3.4 mmol) in acetic anhydride (3.3 mL) was heated at 100° C. under stirring for 2 h. After cooling to RT the precipitate was filtered and washed with 95% ethanol. The solid was then dissolved in dichloromethane, the organic solution washed with water, dried over sodium sulphate and concentrated under reduced pressure to yield 4-[(1-acetyl-1H-pyrrolo[2,3-b]pyridin-3-yl)methylene]-2-phenyl-1,3-oxazol-5(4H)-one as a yellow-orange solid (0.74 g, 65% yield).

This intermediate (0.67 g, 2.0 mmol) was suspended in 30% aqueous ammonia (50 mL), solid sodium carbonate (0.31 g, 2.9 mmol) and methanol (50 mL) were added and the mixture was refluxed for 8 h. Half of the solvent was distilled off and the precipitate was filtered and washed with water. 2-Phenyl-5-(1H-pyrrolo[2,3-b]pyridin-3-ylmethylene)-3,5-dihydro-4H-imidazol-4-one was obtained as yellow solid (0.46 g, 79%).

$^1$H-NMR (DMSOd$_6$), δ ppm: 7.23-7.33 (m, 1H) 7.38 (s, 0.5H, Z isomer) 7.53-7.65 (m, 3H) 7.84 (s, 0.5H, E isomer) 8.04-8.22 (m, 2H) 8.32-8.40 (m, 1H) 8.48 (d, J=7.44 Hz, 0.5H, E isomer) 8.53-8.56 (m, 0.5H, Z isomer) 9.01 (d, J=6.95 Hz, 0.5H, Z isomer) 9.45 (m, 0.5H, E isomer), 11.9 (s, 0.5H, Z isomer), 12.04 (s, 0.5H, E isomer), 12.13 (s, 1H).

The compound was suspended in methanol, excess 4M HCl in dioxane was added and the mixture stirred at RT for 30'. The precipitate was filtered and washed with little methanol and then with diethylether to yield the hydrochloride.

Examples 2-9

By employing the above described procedure and the suitable substituted hyppuric acids, the following compounds of Examples 2-9 were also prepared:

Example 2

(5Z)-2-(3-methylphenyl)-5-(1H-pyrrolo[2,3-b]pyridin-3-ylmethylene)-3,5-dihydro-4-H-imidazol-4-one $^1$H-NMR (DMSOd$_6$), δ ppm: 2.45 (s, 3H) 7.28-7.36 (m, 1H) 7.38 (s, 1H) 7.45 (d, J=8.05 Hz, 1H) 7.47-7.52 (m, 1H) 7.97 (d, J=7.80 Hz, 1H) 8.02 (s, 1H) 8.37 (d, J=4.63 Hz, 1H) 8.57 (s, 1H) 9.02 (d, J=7.68 Hz, 1H) 11.89 (s, 1H) 12.59 (s, 1H).

Example 3

(5Z)-2-(4-methylphenyl)-5-(1H-pyrrolo[2,3-b]pyridin-3-ylmethylene)-3,5-dihydro-4H-imidazol-4-one H-NMR (DMSOd$_6$), δ ppm: 2.43 (s, 3H) 7.29-7.34 (m, 1H) 7.35 (s, 1H) 7.43 (d, J=7.93 Hz, 2H) 8.07 (d, J=8.17 Hz, 2H) 8.36 (d, J=4.76 Hz, 1H) 8.55 (s, 1H) 9.02 (d, J=7.44 Hz, 1H) 11.87 (s, 1H) 12.58 (s, 1H).

Example 4

(5Z)-2-(4-bromophenyl)-5-(1H-pyrrolo[2,3-b]pyridin-3-ylmethylene)-3,5-dihydro-4H-imidazol-4-one H-NMR (DMSOd$_6$), δ ppm: 7.33 (dd, J=7.80, 4.63 Hz, 1H) 7.42 (s, 1H) 7.83 (d, J=8.66 Hz, 2H) 8.11 (d, J=8.66 Hz, 2H) 8.37 (d, J=4.63 Hz, 1H) 8.58 (s, 1H) 9.00 (d, J=7.80 Hz, 1H) 11.97 (s, 1H) 12.63 (s, 1H).

Example 5

(5Z)-2-(4-fluorophenyl)-5-(1H-pyrrolo[2,3-b]pyridin-3-ylmethylene)-3,5-dihydro-4H-imidazol-4-one hydrochloride H-NMR (DMSOd$_6$), δ ppm: 7.32 (dd, J=7.93, 4.76 Hz, 1H) 7.39 (s, 1H) 7.43-7.50 (m, 2H) 8.25 (dd, J=8.90, 5.37 Hz, 1H) 8.36 (dd, J=4.63, 1.46 Hz, 1H) 8.56 (s, 1H) 9.00 (d, J=7.68 Hz, 1H) 12.60 (s, 1H).

Example 6

(5E+5Z)-2-(4-acetylaminophenyl)-5-(1H-pyrrolo[2,3-b]pyridin-3-ylmethylene)-3,5-dihydro-4H-imidazol-4-one)

H-NMR (DMSOd$_6$), δ ppm: (E+Z isomers) 2.12 (s, 3H) 7.29-7.34 (m, 2H) 7.78-7.85 (m, 2H) 8.04-8.14 (m, 2H) 8.31-9.46 (m, 3H) 10.33 (s, 1H) 11.82 (s, 1H) 12.47-12.74 (m, 1H).

Example 7

(5Z)-2-[4-(hydroxymethyl)phenyl]-5-(1H-pyrrolo[2,3-b]pyridin-3-ylmethylene)-3,5-dihydro-4H-imidazol-4-one H-NMR (DMSOd$_6$), δ ppm: 4.62 (s, 2H) 7.33 (dd, J=7.93, 4.63 Hz, 1H) 7.37 (s, 1H) 7.55 (d, J=8.54 Hz, 2H) 8.13 (d, J=8.41 Hz, 2H) 8.36 (dd, J=4.76, 1.58 Hz, 1H) 8.55 (s, 1H) 9.02 (d, J=7.07 Hz, 1H) 11.79-11.96 (m, 1H) 12.57 (s, 1H).

Example 8

(5Z)-2-pyridin-3-yl-5-(1H-pyrrolo[2,3-b]pyridin-3-ylmethylene)-3,5-dihydro-4H-imidazol-4-one H-NMR (DMSOd$_6$), δ ppm: 7.32 (dd, J=8.05, 4.76 Hz, 1H) 7.47 (s, 1H) 7.70-7.78 (m, 1H) 8.37 (dd, J=4.76, 1.59 Hz, 1H) 8.59-8.64 (m, 2H) 8.83 (dd, J=5.00, 1.59 Hz, 1H) 9.02 (d, J=7.07 Hz, 1H) 9.37 (d, J=2.19 Hz, 1H).

Example 9

(5Z)-2-(2-furyl)-5-(1H-pyrrolo[2,3-b]pyridin-3-ylmethylene)-3,5-dihydro-4H-imidazol-4-one H-NMR (DMSOd$_6$), δ ppm: 6.1-8.6 (m, 8H) 11.8 (s, 1H) 12.9 (s, 1H).

Example 10

(5Z)-2-[3-(4-methylpiperazin-1-yl)phenyl]-5-(1H-pyrrolo[2,3-b]pyridin-3-ylmethylene)-3,5-dihydro-4H-imidazol-4-one To a suspension of 3-(4-methylpiperazin-1-yl)benzoic acid (0.58 g, 2 mmol) in dichloromethane (50 mL) and DMF (2 drops), oxalyl chloride (0.9 mL, 10 mmol) was added dropwise at RT. After addition the reaction mixture was heated at 60° C. for 2 h. After concentration and stripping with toluene the crude acyl chloride was dissolved in dry THF (7 mL)/triethylamine (3 mmol) and t-butylglycinate (0.286 mL, 2.1 mmol) was added at RT and the reaction mixture was stirred at RT overnight. After concentration obtained 0.66 g (2 mmol, quant.) of tert-butyl N-[3-(4-methylpiperazin-1-yl)benzoyl]glycinate. The above obtained t-butyl ester (0.1 g, 0.3 mmol) was stirred at RT in dichloromethane (4 mL) and trifluoroacetic acid (3 mL) overnight. The solvents were removed under reduced pressure and the crude material stripped three times with toluene. Obtained the corresponding acid (0.080 g. 96% yield).

The acid was then reacted as described in Example 1 to afford the title compound.

H-NMR (DMSOd$_6$), δ ppm: 2.87 (s, 3H) 3.13-4.03 (m, 8H) 7.24-7.95 (m, 6H) 8.36 (dd, J=4.63, 1.59 Hz, 1H) 8.52 (d, J=2.44 Hz, 1H) 9.11 (d, J=7.32 Hz, 1H) 10.48 (s, 1H) 11.83-11.96 (m, 1H) 12.58 (s,1H)

The compound was suspended in methanol, excess 4M HCl in dioxane was added and the mixture was stirred at RT for 30 minutes. The yellow precipitate was filtered and washed with little methanol and then with diethylether to yield the dihydrochloride.

Examples 11-12

By employing the above described procedure in Example 10 and the suitable substituted hippuric acids the following compounds of Examples 11-12 were also prepared:

Example 11

(5E+5Z)-2-[4-(4methylpiperazin-1-yl)phenyl]-5-(1H-pyrrolo[2,3-b]pyridin-3-ylmethylene)-3,5-dihydro-4H-imidazol-4-one dihydrochloride H-NMR (DMSOd$_6$), mixture of E,Z isomers, δ ppm: 2.85 (s, 3H) 3.05-4.33 (m, 8H) 7.10-9.43 (m, 9H).

Example 12

(5Z)-2-{4-[(1-methylpiperidin-yl)oxy]phenyl}-5-(1H-pyrrolo[2,3-b]pyridin-3-ylmethylene)-3,5-dihydro-4H-imidazol-one dihydrochloride H-NMR (DMSOd$_6$), δ ppm: 1.82-3.63 (m, 11H) 4.62-5.01 (m, 1H) 7.17-7.38 (m, 4H) 8.15 (dd, J=8.90, 6.10 Hz, 2H) 8.35 (dd, J=4.76, 1.59 Hz, 1H) 8.53 (s, 1H) 9.00 (t, J=7.07 Hz, 1H) 10.17-10.46 (m, 1H) 12.54 (s, 1H).

Example 13

(5Z)-2-morpholin-4-yl-5-(1H-pyrrolo[2,3-b]pyridin-3-ylmethylene)-3,5-dihydro-4H-imidazol-4-one dihydrochloride A mixture of azaindole-3-carboxaldehyde (6 g, 41 mmol), thiohydantoin (4.75 g, 41 mmol) and sodium acetate (11.3 g, 138 mmol) in glacial acetic acid (60 mL) was refluxed under stirring for 5 h. After cooling in ice bath the precipitate was filtered and washed with 95% ethanol.

After drying 5-(1H-pyrrolo[2,3-b]pyridin-3-ylmethylene)-2-thioxoimidazolidin-4-one was obtained as a yellow solid (8.9 g, 36.47 mmol, 88%).

$^1$H-NMR (DMSOd$_6$), δ ppm: 6.8 (s, 1H) 7.2(m, 1H) 8.25 (m, 2H) 8.58 (d, 1H) 11.8 (s, 1H) 12.15 (s, 1H) 12.4 (s, 1H).

To a solution of 5-(1H-pyrrolo[2,3-b]pyridin-3-ylmethylene)-2-thioxoimidazolidin-4-one (8 g, 32.8 mmol) in 12.6% aq. NaOH (12 mL) and methanol (80 mL), methyl iodide (2.25 mL, 36 mmol) was added and the reaction mixture stirred at RT for 4 h. Most of the solvent was distilled out and the precipitate was filtered and washed first with water, then with diethylether. The washings were concentrated and extracted with dichloromethane, dried over sodium sulphate and joined to the first solid crop. The whole crop was suspended in methanol, stirred 30', filtered and dried to yield 2-(methylthio)-5-(1H-pyrrolo[2,3-b]pyridin-3-ylmethylene)-3,5-dihydro-4H-imidazol-4-one as a yellow solid (8.15 g, 31.6 mmol, 96%).

$^1$H-NMR (DMSOd$_6$), δ ppm: 2.71 (s, 3H) 7.22 (dd, J=7.7, 4.6 Hz, 1H) 8.30 (dd, J=4.6, 1.58 Hz, 1H) 8.38-8.41 (m, 1H) 8.83 (d, J=7.68 Hz, 1H) 9.22 (s, 1H) 11.60 (s, 1H) 12.36 (s, 1H).

To a suspension of 2-(methylthio)-5-(1H-pyrrolo[2,3-b]pyridin-3-ylmethylene)-3,5-dihydro-4H-imidazol-4-one (0.2 g, 0.77 mmol) in absolute ethanol (5 mL) morpholine (0.85 mL, 9.7 mmol) was added and the mixture was refluxed overnight. After cooling to RT the precipitate was filtered, suspended in methanol (2 mL), 4M HCl in dioxane (0.5 mL) was added and the mixture was stirred at RT for 30'. The yellow precipitate was filtered and washed with methanol and then with diethylether. Obtained (5Z)-2-morpholin4-yl-5-(1H-pyrrolo[2,3-b]pyridin-3-ylmethylene)-3,5-dihydro-4H-imidazol-4-one.2HCl as a yellow solid (0.16 g, 0.54 mmol, 70%).

$^1$H-NMR (DMSOd$_6$), δ ppm: 3.78 (d, 8H) 7.10 (s, 1H) 7.25 (dd, J=8.04, 4.76 Hz, 1H) 8.34 (d, J=4.76, 1H) 8.39 (s, 1H) 8.45(d, J=8.04 Hz, 1H) 12.53 (s, 1H).

Examples 14-43

By employing the above-described procedure in Example 13, the following compounds of Examples were 14-43 were also prepared:

Example 14

(5Z)-2-(4-methylpiperazin-1-yl)-5-(1H-pyrrolo[2,3-b]pyridin-3-ylmethylene)-3,5-dihydro-4H-imidazol-one dihydrochloride $^1$H-NMR (DMSOd$_6$), δ ppm: 2.83 (s, 3H) 3.42 (s, 6H) 4.34 (m, 2H) 6.93 (s, 1H) 7.22 (dd, J=7.68, 4.88 Hz, 1H) 8.32 (d, J=4.78, 1H) 8.38 (s, 1H) 8.56 (d, J=7.68 Hz, 1H) 10.84 (s, 1H) 12.36 (s, 1H).

Example 15

(5Z)-2-(4-phenylpiperazin-1-yl)-5-(1H-pyrrolo[2,3-b]pyridin-3-ylmethylene)-3,5-dihydro-4H-imidazol-4-one trihydrochloride $^1$H-NMR (DMSOd$_6$), δ ppm: 3.44 (s, 8H) 6.88 (t, J=7.39 Hz, 1H) 7.07 (d, J=7.9 Hz, 2H) 7.16 (s, 1H) 7.29 (dd, J=7.9,7.39 Hz, 3H) 8.36 (m, 1H) 8.46 (s, 2H) 12.63 (s, 1H).

Example 16

(5Z)-2-piperidin-1-yl-5-(1H-pyrrolo[2,3-b]pyridin-3-ylmethylene)-3,5-dihydro-4H-imidazol-4-one dihydrochloride $^1$H-NMR (DMSOd$_6$), δ ppm: 1.70 (s, 6H) 3.48 (s, 4H) 7.16 (s, 1H) 7.24 (m, 1H) 8.40 (m, 3H) 12.60 (s, 1H).

Example 17

(5Z)-2-[3-(hydroxymethyl)piperidin-1-yl]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 1.40-1.65 (m, 2H) 1.83 (s, 3H) 3.40 (s, 6H) 7.14(s, 1H) 7.26 (m, 1H) 8.36-8.39 (m, 3H), 12.57 (s, 1H).

Example 18

(5Z)-2-pyrrolidin-1-yl-5-(1H-pyrrolo[2,3-b]pyridin-3-ylmethylene)-3,5-dihydro-4H-imidazol-4-one dihydrochloride $^1$H-NMR (DMSOd$_6$), δ ppm: 2.04 (s, 4H) 3.65 (m, 4H) 7.20(s, 1H) 7.24 (m, 1H) 8.36 (m, 3H), 12.64 (s, 1H).

Example 19

(5Z)-2-(4-benzylpiperazin-1-yl)-5-(1H-pyrrolo[2,3-b]pyridin-3-ylmethylene)-3,5-dihydro-4H-imidazol-4-one trihydrochloride $^1$H-NMR (DMSOd$_6$), δ ppm: 3.51 (m, 8H) 4.38 (s, 2H) 6.95 (s, 1H) 7.23 (dd, J=7.86, 4.82 Hz, 1H) 7.58 (m, 5H) 8.33 (dd, J=4.69, 1.28 Hz, 1H) 8.38 (s, 1H) 8.57 (d, J=7.68 Hz, 1H) 11.31 (s, 1H) 12.41 (s, 1H).

Example 20

(5Z)-2-(4-isopropylpiperazin-1-yl)-5-(1H-pyrrolo[2,3-b]pyridin-3-ylmethylene)-3,5-dihydro-4H-imidazol-4-one dihydrochloride $^1$H-NMR (DMSOd$_6$), δ ppm: 1.32 (d, J=6.58 Hz, 3H) 3.45 (s, 10H) 6.97 (s, 1H) 7.23 (dd, J=7.93, 4.88 Hz, 1H) 8.33(d, J=4.75 Hz, 1H) 12.4 (s, 1H).

Example 21

(5Z)-5-(1H-pyrrolo[2,3-b]pyridin-3-ylmethylene)-2-[4-(tetrahydrofuran-2-ylmethyl)piperazin-1-yl]-3,5-dihydro-4H-imidazol-4-one dihydrochloride $^1$H-NMR (DMSOd$_6$), δ ppm: 2.09 (m, 4H) 3.5-4.34 (m, 12H) 6.95 (s, 1H) 7.22 (dd, J=7.93, 4.75 Hz, 1H) 8.32 (d, J=4.63 Hz, 1H) 8.39 (s, 1H) 8.57 (d, J=7.69 Hz, 1H) 10.73 (bs, 2H) 12.4 (s, 1H).

Example 22

(5Z)-2-[4-(2-hydroxyethyl)piperazin-1-yl]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 3.47 (m, 12H) 6.96 (s, 1H) 7.23 (dd, J=7.93, 4.88 Hz, 1H) 8.32 (d, J=4.75 Hz, 1H) 8.41 (s, 1H) 8.57 (d, J=7.68 Hz, 1H) 10.6 (bs, 1H) 12.42 (s, 1H).

Example 23

(5Z)-2-(4-phenylpiperidin-1-yl)-5-(1H-pyrrolo[2,3-b]pyridin-3-ylmethylene)-3,5-dihydro-4H-imidazol one ditrifluoroacetate $^1$H-NMR (DMSOd$_6$), δ ppm: 1.7 (m, 2H) 1.91(d, J=11.46 Hz, 1H) 4.33 (d, J=11.2 Hz, 4H) 6.85 (s, 1H) 7.3 (m, 6H) 8.29 (d, 2H) 8.46 (d, J=8.05 Hz, 1H).

Example 24

(5Z)-2-(1,4'-bipiperidin-1'-yl)-5-(1H-pyrrolo[2,3-b]pyridin-3-ylmethylene)-3,5-dihydro-4H-imidazol-4-one trihydrochloride $^1$H-NMR (DMSOd$_6$), δ ppm: 1.5-2.4 (m, 12H) 2.8 (m, 4H) 4.5 (bs, 2H) 7.08 (s, 1H) 7.23 (dd, J=8.05, 4.88 Hz, 1H) 8.34 (d, J=4.87 Hz, 1H) 8.46 (d, J=8.04 Hz, 2H) 10.48 (bs, 1H) 12.55 (s, 1H).

Example 25

(5Z)-2-azepan-1-yl-5-(1H-pyrrolo[2,3-b]pyridin-3-ylmethylene)-3,5-dihydro-4H-imidazol-4-one dihydrochloride $^1$H-NMR (DMSOd$_6$), δ ppm: 1.5-2.0 (m, 8H) 3.7 (2 s, 4H) 7.17 (s, 1H) 7.24 (dd, J=7.93, 4.76 Hz, 1H) 8.38 (2 d, J=7.81, 4.76 Hz, 3H) 12.61 (s, 2H).

Example 26

(5Z)-1-[5-oxo-4-(1H-pyrrolo[2,3-b]pyridin-3-ylmethylene)-4,5-dihydro-1H-imidazol-2-yl]piperidine-3-carboxamide ditrifluoroacetate $^1$H-NMR (DMSOd$_6$), δ ppm: 1.5-2.0 (m, 5H) 4.2 (m, 2H) 6.9 (s, 1H) 6.99 (s, 1H) 7.18 (dd, J=7.92, 4.75 Hz, 1H) 7.44 (s, 1H) 8.29 (m, 2H) 8.44 (d, J=7.32 Hz, 1H).

Example 27

(5Z)-2-(piperazin-1-yl)-5-(1H-pyrrolo[2,3-b]pyridin-3-ylmethylene)-3,5-dihydro-4H-imidazol-4-one tritrifluoroacetate $^1$H-NMR (DMSOd$_6$), δ ppm: 3.82 (t, 4H) 6.81 (s, 1H) 7.15 (dd, J=7.80, 4.63 Hz, 1H) 8.28 (m, 2H) 8.53 (d, J=7.80 Hz, 1H) 8.93 (s, 1H).

Example 28

(5Z)-2-[4-(2-furoyl)piperazin-1-yl]-5-(1H-pyrrolo[2,3-b]pyridin-3-ylmethylene)-3,5-dihydro-4H-imidazol-4-one dihydrochloride H-NMR (DMSOd$_6$), δ ppm: 3.87 (d, 8H) 6.69 (dd, J=3.41, 1.70 Hz, 1H) 7.11 (m, 3H) 7.24 (dd, J=7.9, 4.7 Hz, 1H) 7.91 (d, J=1.83 Hz, 1H) 8.35 (d, J=4.7 Hz, 1H) 8.43 (s, 1H) 8.48 (d, J=7.69 Hz, 1H).

Example 29

(5Z)-2-(1,3-dihydro-2H-isoindol-2-yl)-5-(1H-pyrrolo[2,3-b]pyridin-3-ylmethylene)-3,5-dihydro-4H-imidazol-4-one dihydrochloride H-NMR (DMSOd$_6$), δ ppm: 5.05-5.3(m, 4H) 7.3-7.5 (m, 6H) 8.5 (m, 3H) 12.6 (s, 1H).

Example 30

(5Z)-2-(2-methylmorpholin-4-yl)-5-(1H-pyrrolo[2,3-b]pyridin-3-ylmethylene)-3,5-dihydro-4H-imidazol-4 one dihydrochloride H-NMR (DMSOd6), δ ppm: 1.18(d, 3H) 3.5 (m, 7H) 7.13 (s, 1H) 7.24 (dd, J=7.9, 4.7 Hz, 1H) 8.3 (d, J=4.7 Hz, 1H) 8.44 (d, J=8.0 Hz, 1H) 12.57 (s, 1H).

Example 31

(5Z)-2-(4-propylpiperazin-1-yl)-5-(1H-pyrrolo[2,3-b]pyridin-3-ylmethylene)-3,5-dihydro-4H-imidazol-4-one dihydrochloride H-NMR (DMSOd$_6$), δ ppm: 0.95(t, 3H) 1.71 (m, 2H) 3.4 (m, 10H) 6.83 (s, 1H) 7.15 (dd, J=7.8, 4.63 Hz, 1H) 8.28 (dd, J=1.09, 4.39 Hz, 2H) 8.53 (d, J=7.8 Hz, 1H) 9.81 (bs, 1H) 12.15 (s, 1H).

Example 32

(5Z)-2-(4-methylpiperidin-1-yl)-5-(1H-pyrrolo[2,3-b]pyridin-3-ylmethylene)-3,5-dihydro-4H-imidazol-4-one dihydrochloride H-NMR (DMSOd$_6$), δ ppm: 0.96 (d, 3H) 1.4-1.8 (m, 5H) 3.4 (s, 4H) 7.16 (s, 1H) 7.24 (dd, J=7.9, 4.7 Hz, 1H) 8.35 (m, 3H) 12.15 (s, 1H).

Example 33

(5Z)-2-(2,6-dimethylmorpholin-4-yl)-5-(1H-pyrrolo[2,3-b]pyridin-3-ylmethylene)-3,5-dihydro-4H-imidazol-4-one dihydrochloride H-NMR (DMSOd$_6$), δ ppm: 1.17(d, 1H) 7.10 (s, 1H) 7.23 (dd, J=7.93, 4.76 Hz, 1H) 8.34 (dd, J=4.75, 1.46 Hz, 1H) 8.5 (m, 2H) 12.15 (s, 1H).

Example 34

(5Z)-2-(3,5-dimethylpiperidin-1-yl)-5-(1H-pyrrolo[2,3-b]pyridin-3-ylmethylene)-3,5-dihydro-4H-imidazol-4-one ditrifluoroacetate H-NMR (DMSOd$_6$), δ ppm: 0.94 (2s, 6H) 1.81 (m, 4H) 2.72 (m, 2H) 4.14 (bs, 2H) 7.02 (s, 1H) 7.22 (dd, J=7.92, 4.75 Hz, 1H) 8.32 (m, 2H) 8.4 (d, J=7.8 Hz, 1H) 12.40 (s, 1H).

Example 35

(5Z)-2-[4-(cyclohexylmethyl)piperazin-1-yl]-5-(1H-pyrrolo[2,3-b]pyridin-3-ylmethylene)-3,5-dihydro-4H-imidazol-4-one trihydrochloride H-NMR (DMSOd$_6$), δ ppm: 0.98-1.9 (m, 11H) 6.96 (s, 1H) 7.24 (dd, J=8.05, 4.88 Hz, 1H) 8.33 (dd, J=4.86, 1.22 Hz, 1H) 8.40 (s, 1H) 8.57 (d, J=8.05 Hz, 1H) 10.42 (bs, 1H) 12.43 (s, 1H).

Example 36

(5Z)-2-(4-benzylpiperidin-1-yl)-5-(1H-pyrrolo[2,3-b]pyridin-3-ylmethylene)-3,5-dihydro-4H-imidazol-4-one dihydrochloride H-NMR (DMSOd$_6$), δ ppm: 1.39-1.94 (m, 5H) 2.58 (d, 2H) 7.15 (s, 1H) 7.2-7.4 (m, 5H) 8.40 (m, 3H) 12.6 (s, 1H).

Example 37

(5Z)-2-(4-pyrrolidin-1-ylpiperidin-1-yl)-5-(1H-pyrrolo[2,3-b]pyridin-3-ylmethylene)-3,5-dihydro-4H-imidazol-4-one trihydrochloride H-NMR (DMSOd$_6$), δ ppm: 1.6-2.23 (m, 13H) 3.10 (m, 2H) 4.34 (m, 2H) 7.04 (s, 1H) 7.23 (dd, J=7.8, 4.75 Hz, 1H) 8.33 (d, J=4.7 Hz, 1H) 8.45 (s, 1H) 8.5 (d, J=7.8 Hz, 1H) 10.8 (bs, 1H) 12.5 (s, 1H).

Example 38

(5Z)-2-(1,4-diazepan-1-yl)-5-(1H-pyrrolo[2,3-b]pyridin-3-ylmethylene)-3,5-dihydro-4H-imidazol-4-one trihydrochloride H-NMR (DMSOd$_6$), δ ppm: 2.18 (s, 2H) 3.4 (s, 8H) 7.06 (s, 1H) 7.23 (dd, J=7.92, 4.75 Hz, 1H) 8.34 (dd, J=4.7, 1.34 Hz, 1H) 8.42 (s, 1H) 8.5 (d, J=7.9 Hz, 1H) 9.34 (s, 2H) 12.5 (s, 1H).

Example 39

(5Z)-2-[4-(3,4-dichlorophenyl)piperazin-1-yl]-5-(1H-pyrrolo[2,3-b]pyridin-3-ylmethylene)-3,5-dihydro-4H-imidazol-4-one trihydrochloride H-NMR (DMSOd$_6$), δ ppm: 3.89 (s, 8H) 7.06 (dd, J=9.15, 2.9 Hz, 1H) 7.13 (s, 1H) 7.27 (dd, J=4.7, 2.9 Hz, 2H) 7.46 (d, J=9.1 Hz, 1H) 8.35 (dd, J=4.76, 1.47 Hz, 1H) 8.45 (m, 2H) 12.6 (s, 2H).

Example 40

(5Z)-(2-[4-(2-fluorophenyl)piperazin-1-yl]-5-(1H-pyrrolo[2,3-b]pyridin-3-ylmethylene)-3,5-dihydro-4H-imidazol-4-one trihydrochloride H-NMR (DMSOd$_6$), δ ppm: 7.0-7.4 (m, 6H) 8.35-8.48 (m, 3H) 12.60 (s, 1H).

Example 41

(5Z)-2-[4-(2-methoxyethyl)piperazin-1-yl]-5-(1H-pyrrolo[2,3-b]pyridin-3-ylmethylene)-3,5-dihydro-4H-imidazol-4-one trihydrochloride H-NMR (DMSOd$_6$), δ ppm: 3.2-4.4 (m, 15H) 6.92 (s, 1H) 7.20 (dd, J=7.92, 4.75 Hz, 1H) 8.31 (s, 1H) 8.37 (d, J=4.75 Hz, 1H) 8.56 (d, J=7.42 Hz, 1H) 10.70 (bs, 2H) 12.35 (s, 2H).

Example 42

(5Z)-2-[4(4-fluorophenyl)piperazin-1-yl]-5-(1H-pyrrolo[2,3-b]pyridin-3-ylmethylene)-3,5-dihydro-4H-imidazol one trihydrochloride H-NMR (DMSOd$_6$), δ ppm: 3.35-3.8 (m, 8H) 7.10 (m, 5H) 7.25 (dd, J=7.92, 4.75 Hz, 1H) 8.36 (dd, J=4.75, 1.46 Hz, 1H) 8.47 (m, 2H) 12.64 (s, 1H).

Example 43

(5Z)-2-[(2R)-2-benzylmorpholin-yl]-5-(1H-pyrrolo[2,3-b]pyridin-3-ylmethylene)-3,5-dihydro-4H-imidazol-4-one hydrochloride trifluoroacetate $^1$H-NMR (DMSOd$_6$), δ ppm: 2.82-4.05 (m, 9H) 6.88 (s, 1H) 7.19 (dd, J=7.6, J=4.76 Hz, 1H) 7.30 (m, 5H) 8.20 (s, 1H) 8.30 (dd, J=4.64 Hz, 1H) 8.47 (d, J=7.56 Hz, 1H) 12.27 (bs, 1H) 12.51 (s, 1H).

Example 44

(5Z)-2-(cyclohexylamino)-5-(1H-pyrrolo[2,3-b]pyridin-3-ylmethylene)-3,5-dihydro-4H-imidazol-4-one dihydrochloride To a suspension of 2-(methylthio)-5-(1H-pyrrolo[2,3-b]pyridin-3-ylmethylene)-3,5-dihydro-4H-imidazol-4-one (0.2 g, 0.77 mmol) in absolute ethanol (5 mL) cyclohexylamine (1.1 mL, 9.7 mmol) was added and the mixture was refluxed overnight. After cooling to RT the precipitate was filtered, suspended in methanol (2 mL), 4M HCl in dioxane (0.5 mL) was added and the mixture was stirred at RT for 30'. The yellow precipitate was filtered and washed with methanol and then with diethylether. Obtained (5Z)-2-(cyclohexylamino)-5-(1H-pyrrolo[2,3-b]pyridin-3-ylmethylene)-3,5-dihydro-4H-imidazol-4-one.2HCl as a yellow solid (0.25 g, 0.66 mmol, 86%).

$^1$H-NMR (DMSOd$_6$), δ ppm: 1.56 (m, 10H) 3.62 (m, 1H) 7.18 (s, 1H) 7.25 (dd, J=7.93, 4.76 Hz, 1H) 8.34 (s, 1H) 8.36 (dd, J=4.69, 1.52 Hz, 1H) 8.40 (d, J=7.93 Hz, 1H) 9.46 (s, 1H) 11.79 (s, 1H) 12.62 (s, 1H).

Examples 45-129

By employing the above described procedure in Example 44, the following compounds of Examples 45-129 were also prepared:

Example 45

(5Z)-2-[(1-benzylpiperidin-4-yl)amino]-5-(1H-pyrrolo[2,3-b]pyridin-3-ylmethylene)-3,5-dihydro-4H-imidazol-4-one trihydrochloride $^1$H-NMR (DMSOd$_6$), δ ppm: 3.41-3.47 (s, 9H) 4.36 (s, 2H) 7.23 (s, 1H) 7.26 (dd, J=7.95, 4.75 Hz, 1H) 7.51-7.64 (m, 5H) 8.35 (d, J=4.75 Hz, 2H) 8.36 (d, J=7.95 Hz, 1H) 10.71 (bs, 2H) 12.60 (bs, 1H).

Example 46

(5Z)-2-(benzylamino)-5-(1H-pyrrolo[2,3-b]pyridin-3-ylmethylene)-3,5-dihydro-4H-imidazol-4-one hydrochloride $^1$H-NMR (DMSOd$_6$), δ ppm: 4.79 (s, 2H) 7.24-7.45 (m, 7H) 8.35-8.38 (m, 3H) 9.62 (bs, 1H) 12.62 (bs, 2H).

Example 47

(5Z)-2-[(2-hydroxyethyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 3.43 (s, 4H) 7.19(s, 1H) 7.24(dd, J=7.8, 4.7 Hz, 1H) 8.37 (dd, J=7.78, 4.7 Hz, 3H) 9.07 (bs, 1H) 12.65 (s, 2H).

Example 48

(5Z)-2-[(3,3-dimethylbutyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 0.97 (s, 9H) 1.57 (s, 2H) 7.17 (s, 1H) 7.24 (dd, J=7.75, 4.68 Hz, 1H) 8.37 (dd, J=7.78, 4.6 Hz, 2H) 8.38 (s, 1H) 9.17 (s, 1H) 12.64 (s, 2H).

Example 49

(5Z)-2-[(2-furylmethyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 4.74 (s, 2H) 6.5 (m, 2H) 7.19 (s, 1H) 7.24 (dd, J=7.9, 4.76 Hz, 1H) 7.72 (s, 1H) 8.37 (m, 2H) 8.41 (d, J=7.84 Hz, 1H) 9.61 (bs, 1H) 12.62 (s, 2H).

Example 50

(5Z)-2-(cyclopropylamino)-5-(1H-pyrrolo[2,3-b]pyridin-3-ylmethylene)-3,5-dihydro-4H-imidazol-4-one dihydrochloride $^1$H-NMR (DMSOd$_6$), δ ppm: 0.92 (m, 4H) 7.21 (s, 1H) 7.24 (dd, J=7.8, 4.58 Hz, 1H) 8.36 (m, 3H) 9.61 (bs, 1H) 12.63(s, 3H).

Example 51

(5Z)-5-(1H-pyrrolo[2,3-b]pyridin-3-ylmethylene)-2-[(thien-2-ylmethyl)amino]-3,5-dihydro-4H-imidazol-4-one dihydrochloride $^1$H-NMR (DMSOd6), δ ppm: 4.91 (s, 2H) 7.08 (dd, J=5.12, 3.54 Hz, 1H) 7.18 (s, 1H) 7.23 (m, 2H) 7.55 (d, J=5.12 Hz, 1H) 8.37 (m, 3H) 9.63 (bs, 1H) 12.61(bs, 3H).

Example 52

(5Z)-2-(propylamino)-5-(1H-pyrrolo[2,3-b]pyridin-3-ylmethylene)-3,5-dihydro-4H-imidazol-4-one dihydrochloride $^1$H-NMR (DMSOd$_6$), δ ppm: 0.96 (t, J=7.44 3H) 1.64 (d, J=7.44 Hz, 2H) 3.40 (s, 2H) 7.18 (s, 1H) 7.27 (dd, J=7.92, 4.75 Hz, 1H) 8.36 (dd, J=7.81, 4.75 Hz, 1H) 9.4 (bs, 1H) 11.8 (bs, 1H) 12.63 (s, 1H).

Example 53

(5Z)-2-[(2-piperidin-1-ylethyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 1.56 (s, 2H) 1.75 (s, 4H) 3.78 (m, 8H) 6.82 (s, 1H) 7.17 (dd, J=7.92, 4.63 Hz, 1H) 8.21 (s, 1H) 8.30 (d, J=4.6 Hz, 1H) 8.49 (s, 1H) 12.19 (bs, 1H).

Example 54

(5Z)-2-[(3-furylmethyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 4.55 (s, 2H) 6.61 (s, 1H) 7.19 (s, 1H) 7.23 (dd, J=7.93, 4.76 Hz, 1H) 7.71 (s, 1H) 7.79 (s, 1H) 9.5 (bs, 1H) 12.7 (s, 1H).

Example 55

(5Z)-2-[(2-morpholin-1-ylethyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 3.41 (s, 12H) 7.12 (bs, 2H) 7.23 (dd, J=7.81, 4.64 Hz, 1H) 8.35 (d, J=4.63 Hz, 1H) 8.45 (s, 2H) 8.97 (s, 1H) 12.56 (s, 1H).

Example 56

(5Z)-5-(1H-pyrrolo[2,3-b]pyridin-3-ylmethylene)-2-[(tetrahydrofuran-2-ylmethyl)amino]-3,5-dihydro-4H-imidazol-4-one hydrochloride $^1$H-NMR (DMSOd$_6$), δ ppm: 0.5-1.9 (m, 4H) 3.71 (m, 2H) 4.07 (s, 1H) 7.06 (s, 1H) 7.23 (dd, J=7.8, 4.6 Hz, 1H) 8.20 (s, 1H) 8.35 (2d, J=7.61, 4.51 Hz, 2H) 9.3 (bs, 1H) 12.5 (s, 1H).

Example 57

(5Z)-2-(pentylamino)-5-(1H-pyrrolo[2,3-b]pyridin-3-ylmethylene)-3,5-dihydro-4H-imidazol-4-one dihydrochloride H-NMR (DMSOd$_6$), δ ppm: 0.9 (t, 3H) 1.34-1.6 (2 s, 6H) 7.2 (s, 1H) 7.25 (dd, J=7.93, 4.76 Hz, 1H) 8.4 (2 d, J=8.2, 4.76 Hz, 3H) 12.6 (s, 1H).

Example 58

(5Z)-2-(heptylamino)-5-(1H-pyrrolo[2,3-b]pyridin-3-ylmethylene)-3,5-dihydro-4H-imidazol-4-one ditrifluoroacetate H-NMR (DMSOd$_6$), δ ppm: 0.88 (t, 3H) 1.30-1.6 (2d, 10H) 7.0 (b s, 1H) 7.22 (dd, J=7.68, 4.88 Hz, 1H) 8.2 (s, 1H) 8.33 (d, J=4.88 Hz, 1H) 8.4 (s, 1H) 8.94 (s, 1H) 12.47 (s, 2H).

Example 59

(5Z)-2-[(cyclohexylmethyl)amino]-5-(1H-pyrrolo[2,3-b]pyridin-3-ylmethylene)-3,5-dihydro-4H-imidazol-4-one dihydrochloride H-NMR (DMSOd$_6$), δ ppm: 0.8-1.7(m, 11H) 7.17 (s, 1H) 7.25 (dd, J=7.93, 4.7 Hz, 1H) 8.36 (m, 3H) 9.3 (s, 1H).

Example 60

(5Z)-2-[(2-methylbutyl)amino]-5-(1H-pyrrolo[2,3-b]pyridin-3-ylmethylene)-3,5-dihydro-4H-imidazol-4-one dihydrochloride H-NMR (DMSOd$_6$), δ ppm: 0.9 (m, 6H) 1.2-1.7 (m, 3H) 7.18 (s, 1H) 7.27 (dd, J=7.93, 4.76 Hz, 1H) 8.36 (dd, J=1.46, 4.63 Hz, 2H) 8.4 (d, J=7.8 Hz, 1H) 9.3 (s, 1H).

Example 61

(5Z)-2-[(cyclopropylmethyl)amino]-5-(1H-pyrrolo[2,3-b]pyridin-3-ylmethylene)-3,5-dihydro-4H-imidazol-4-one dihydrochloride H-NMR (DMSOd$_6$), δ ppm: 0.36-0.5 (m, 4H) 1.15 (s, 1H) 3.40 (s, 2H) 7.18 (s, 1H) 7.24 (dd, J=7.8, 4.6 Hz, 1H) 8.37 (m, 3H) 12.64(s, 1H).

Example 62

(5Z)-2-[(3-isopropoxypropyl)amino]-5-(1H-pyrrolo[2,3-b]pyridin-3-ylmethylene)-3,5-dihydro-4H-imidazol-4-one dihydrochloride H-NMR (DMSOd$_6$), δ ppm: 1.09 (2 s, 6H) 1.83 (s, 2H) 3.41 (m, 5H) 7.18 (s, 1H) 7.24 (dd, J=7.9, 4.76 Hz, 1H) 8.37 (m, 3H) 9.3 (s, 1H) 12.0 (bs, 1H) 12.6 (s, 2H).

Example 63

(5Z)-2-(ethylamino)-5-(1H-pyrrolo[2,3-b]pyridin-3-ylmethylene)-3,5-dihydro-4H-imidazol-4-one dihydrochloride H-NMR (DMSOd$_6$), δ ppm: 1.24 (t, 3H) 7.18 (s, 1H) 7.27 (dd, J=7.9,4.7 Hz, 1H) 8.37 (m, 3H) 9.2 (bs, 1H) 11.94 (bs, 1H) 12.64 (s, 1H).

Example 64

(5Z)-2-[(2-phenylethyl)amino]-5-(1H-pyrrolo[2,3-b]pyridin-3-ylmethylene)-3,5-dihydro-4H-imidazol-4-one dihydrochloride H-NMR (DMSOd$_6$), δ ppm: 2.9 (t, 2H) 3.8 (t, 2H) 6.9-7.4 (m, 7H) 8.2-8.5 (m, 3H) 12.5 (bs, 1H).

Example 65

(5Z)-2-[(4-fluorobenzyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 4.71 (m, 2H) 7.27-7.51 (m, 7H) 8.37 (m, 2H) 9.63 (bs, 1H) 12.63 (bs, 1H).

Example 66

(5Z)-2-[(3-fluorobenzyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 4.75 (m, 2H) 7.27-7.51 (m, 6H) 8.37 (m, 3H) 9.64 (bs, 1H) 12.63 (bs, 1H).

Example 67

(5Z)-2-[(2-fluorobenzyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 4.80 (s, 2H) 7.37-7.65 (m, 7H) 8.37 (m, 4H) 9.60 (bs, 1H) 12.08 (bs, 1H) 12.64 (bs, 1H).

Example 68

(5Z)-2-[(3-chlorobenzyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 4.74 (m, 2H) 7.27-7.65 (m, 5H) 8.37 (m, 3H) 9.64 (bs, 1H) 12.63 (bs, 1H).

Example 69

(5Z)-2-[(4-chlorobenzyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 4.72 (m, 2H) 7.27-7.6 (m, 6H) 8.37 (m, 3H) 9.62 (bs, 1H) 12.63 (bs, 1H).

Example 70

(5Z)-2-[(3,4-dichlorobenzyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 4.73 (m, 2H) 7.21-7.75 (m, 4H) 8.37 (m, 3H) 9.60 (bs, 1H) 12.62 (bs, 1H).

Example 71

(5Z)-2-[(3-bromobenzyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 4.73 (m, 2H) 7.19-7.70 (m, 6H) 8.37 (m, 3H) 9.62 (bs, 1H) 12.63 (bs, 1H).

Example 72

(5Z)-2-[(3-methylbenzyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 2.35 (s, 3H) 4.68(m, 2H) 7.27-7.32 (m, 6H) 8.37 (m, 3H) 9.62 (bs, 1H) 12.64 (s, 1H).

Example 73

(5Z)-2-[(4-methylbenzyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 2.33 (s, 3H) 4.67 (m, 2H) 7.19-7.33 (m, 6H) 8.37 (m, 3H) 9.59 (bs, 1H) 12.63 (s, 1H).

Example 74

(5Z)-5-(1H-pyrrolo[2,3-b]pyridin-3-ylmethylene)-2-{[4-(trifluoromethyl)benzyl]amino}-3,5-dihydro-4H-imidazol-4-one dihydrochloride $^1$H-NMR (DMSOd$_6$), δ ppm: 4.84 (m, 2H) 7.23 (m, 3H) 7.69 (d, J=8.1 Hz, 2H) 7.79 (d, J=8.17 Hz, 2H) 8.37 (m, 4H) 9.68 (bs, 1H) 12.63 (bs, 1H).

Example 75

(5Z)-2-[(4-methoxybenzyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 3.78 (s, 3H) 4.63 (m, 2H) 7.00 (d, J=8.1 Hz, 2H) 7.19-7.24 (m, 3H) 7.38 (d, J=8.17 Hz, 2H) 8.37 (m, 4H) 9.58 (bs, 1H) 12.64 (bs, 1H).

Example 76

(5Z)-2-[(3,4-dimethoxybenzyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 3.77,3.79 (2 s, 6H) 4.62 (m, 2H) 6.99 (s, 2H) 7.09 (s, 2H) 7.20 (s, 2H) 7.24 (m, 1H) 8.37 (m, 4H) 9.60 (bs, 1H) 12.02 (bs, 1H) 12.64 (s, 2H).

Example 77

(5Z)-5-(1H-pyrrolo[2,3-b]pyridin-3-ylmethylene)-2-{[(1R,2R,3R)-2,6,6-trimethylbicyclo[3.1.1]hept-3-yl]amino}-3,5-dihydro-4H-imidazol-4-one dihydrochloride $^1$H-NMR (DMSOd$_6$), δ ppm: 1.06,1.25 (2 s, 6H) 1.11 (m, 3H) 1.7-2.53 (m, 8H) 4.04 (s, 1H) 7.18 (s, 1H) 7.25 (m, 1H) 8.33-8.40 (m, 3H) 9.75 (bs, 1H) 11.72 (s, 1H) 12.63 (s, 1H).

Example 78

(5Z)-2-[(3,4-difluorobenzyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 4.72 (s, 2H) 7.18-7.31 (m, 3H) 7.58 (m, 2H) 8.37 (m, 3H) 9.60 (bs, 1H) 12.61 (bs, 1H).

Example 79

(5Z)-2-(cycloheptylamino)-5-(1H-pyrrolo[2,3-b]pyridin-3-ylmethylene)-3,5-dihydro-4H-imidazol-4-one dihydrochloride $^1$H-NMR (DMSOd$_6$), δ ppm: 1.4-2.0 (m, 12H) 3.86 (s, 2H) 7.17 (s, 1H) 7.26 (m, 1H) 8.35 (m, 3H) 9.54 (bs, 1H) 11.6 (bs, 1H) 12.63 (bs, 1H).

Example 80

(5Z)-2-[(2-methylcyclohexyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 0.95 (m, 3H) 1.1-2.04 (m, 9H) 3.87 (s, 2H) 7.19 (s, 1H) 7.25 (m, 1H) 8.36 (m, 3H) 9.54 (s, 1H) 12.6 (bs, 1H) 12.63 (bs, 1H).

Example 81

(5Z)-2-[(3-methylcyclohexyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 0.95-2.04 (m, 13H) 3.58 (s, 2H) 7.17 (s, 1H) 7.26 (m, 1H) 8.36 (m, 3H) 9.3 (s, 1H) 11.65 (bs, 1H) 12.63 (bs, 1H).

Example 82

(5Z)-2-[(2,2'-bithien-5-ylmethyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 4.90 (s, 2H) 7.11-7.51 (m, 5H) 8.36 (m, 3H) 9.66 (bs, 1H) 12.61 (bs, 1H).

Example 83

(5Z)-2-{[(3-methylthien-2-yl)methyl]amino}-5-(1H-pyrrolo[2,3-b]pyridin-3-ylmethylene)-3,5-dihydro-4H-imidazol-4-one dihydrochloride $^1$H-NMR (DMSOd$_6$), δ ppm: 3.27 (s, 3H) 4.83 (s, 2H) 6.96 (d, J=5.13 Hz, 1H) 7.18-7.25 (m, 3H) 7.44 (d, J=5.13 Hz, 1H) 8.37 (m, 4H) 9.63 (bs, 1H) 12.00 (bs, 1H) 12.62 (s, 1H).

Example 84

(5Z)-5-(1H-pyrrolo[2,3-b]pyridin-3-ylmethylene)-2-(1,2,3,4-tetrahydronaphthalen-1-ylamino)-3,5-dihydro-4H-imidazol-4-one dihydrochloride $^1$H-NMR (DMSOd$_6$), δ ppm: 1.6-2.75 (m, 6H) 5.03 (s,1H) 7.22-7.4 (m, 6H) 8.36 (m, 3H) 9.75 (bs, 1H) 11.83 (bs, 1H) 12.61 (s, 1H).

Example 85

(5Z)-2-{[(5-pyridin-2-ylthien-2-yl)methyl]amino}-5-(1H-pyrrolo[2,3-b]pyridin-3-ylmethylene)-3,5-dihydro-4H-imidazol-4-one dihydrochloride $^1$H-NMR (DMSOd$_6$), δ ppm: 4.94 (s, 2H) 7.26 (m, 4H) 7.74-7.92 (m, 3H) 8.36-8.52 (m, 4H) 9.73 (bs, 1H) 12.66 (bs, 1H).

Example 86

(5Z)-2-[(4-tert-butylcyclohexyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 0.88-2.15 (m, 18H) 3.5 (bs, 1H) 7.17 (s, 1H) 7.23 (m, 1H) 8.32-8.4 (m, 3H) 9.34 (bs, 1H) 11.73 (bs, 1H) 12.61 (bs, 1H).

Example 87

(5Z)-5-(1H-pyrrolo[2,3-b]pyridin-3-ylmethylene)-2-{[(1R,2S,4R)-1,7,7-trimethylbicyclo[2.2.1]hept-2-yl]amino}-3,5-dihydro-4H-imidazol-4-one dihydrochloride $^1$H-NMR (DMSOd$_6$), δ ppm: 0.91 (m, 9H) 1.13-2.34 (m, 6H) 3.98 (s, 1H) 7.18 (s, 1H) 7.25 (m, 1H) 8.36-8.41 (m, 3H) 9.67 (d, 1H) 11.94 (bs, 1H) 12.68 (s, 1H).

Example 88

(5Z)-2-(cyclopentylamino)-5-(1H-pyrrolo[2,3-b]pyridin-3-ylmethylene)-3,5-dihydro-4H-imidazol-4-one dihydrochloride $^1$H-NMR (DMSOd$_6$), δ ppm: 1.63-2.4 (m, 8H) 4.1 (s, 1H) 7.18-7.24 (m, 3H) 8.36 (m, 4H) 9.57 (bs, 1H) 11.76 (bs, 1H) 12.63 (s, 1H).

Example 89

(5Z)-2-[(4-methylcyclohexyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 0.92-1.96 (m, 12H) 3.39 (s,1H) 7.17-7.26 (m, 3H) 8.36 (m, 4H) 9.35 (bs, 1H) 11.77 (bs, 1H) 12.62 (s, 1H).

Example 90

(5Z)-2-[(2,3-dimethylcyclohexyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 0.92-2.05 (m, 14H) 3.76 (s, 1H) 7.18-7.24 (m, 3H) 8.36 (m, 4H) 9.45 (bs, 1H) 11.85 (bs, 1H) 12.64 (s, 1H).

Example 91

(5Z)-2-[(1-phenylethyl)amino]-5-(1H-pyrrolo[2,3-b]pyridin-3-ylmethylene)-3,5-dihydro-4H-imidazol-4-one dihydrochloride $^1$H-NMR (DMSOd6), δ ppm: 1.63 (d, 3H) 5.08 (bs, 1H) 7.17-7.51 (m, 7H) 8.37 (m, 3H) 9.99 (bs, 1H) 11.90 (bs, 1H) 12.63 (bs, 1H).

Example 92

(5Z)-2-{[1-(4-fluorophenyl)ethyl]amino}-5-(1H-pyrrolo[2,3-b]pyridin-3-ylmethylene)-3,5-dihydro-4H-imidazol-4-one dihydrochloride $^1$H-NMR (DMSOd$_6$), δ ppm: 1.61 (d, 3H) 5.08 (bs, 1H) 7.14-7.27 (m, 4H) 7.51 (m, 2H) 8.35 (m, 4H) 9.93 (bs, 1H) 11.88 (bs, 1H) 12.57 (bs, 1H).

Example 93

(5Z)-2-[(2,3-dihydro-1H-inden-1-ylmethyl)amino]-5-(1H-pyrrolo[2,3-b]pyridin-3-ylmethylene)-3,5-dihydro-4H-imidazol-4-one trifluoroacetate $^1$H-NMR (DMSOd$_6$), δ ppm: 2.09-2.6 (m, 2H) 2.92-3.05 (m, 2H) 5.49 (bs, 1H) 7.01 (s, 1H) 7.20-7.44 (m, 4H) 8.31-8.44 (m, 3H) 12.34 (bs, 1H).

Example 94

(5Z)-2-{[4-(4-methylpiperazin-1-yl)benzyl]amino}-5-(1H-pyrrolo[2,3-b]pyridin-3-ylmethylene)-3,5-dihydro-4H-imidazol-4-one dihydrochloride $^1$H-NMR (DMSOd$_6$), δ ppm: 2.82 (s, 3H) 3.11 (m, 4H) 3.42 (m, 2H) 3.87 (d, 2H) 4.62 (s, 2H) 7.06 (d, J=8.66 Hz, 2H) 7.20-7.24 (m, 2H) 7.35 (d, J=8.45 Hz, 2H) 8.37-8.44 (m, 3H) 10.59 (bs, 1H) 12.65 (s, 1H).

Example 95

(5Z)-2-[(1-phenylpropyl)amino]-5-(1H-pyrrolo[2,3-b]pyridin-3-ylmethylene)-3,5-dihydro-4H-imidazol-4-one trifluoroacetate $^1$H-NMR (DMSOd$_6$), δ ppm: 0.93 (m, 3H) 1.94 (m, 2H) 4.85 (bs, 2H) 6.85 (bs, 1H) 7.19-7.45 (m, 6H) 8.13 (s, 1H) 8.30 (s, 1H) 8.45 (bs, 1H) 12.47 (bs, 1H).

Example 96

(5Z)-5-(1H-pyrrolo[2,3-b]pyridin-3-ylmethylene)-2-[(1S)-1,2,3,4-tetrahydronaphthalen-1-ylamino]-3,5-dihydro-4H-imidazol-4-one dihydrochloride $^1$H-NMR (DMSOd$_6$), δ ppm: 1.75-2.15 (m, 4H) 2.80 (m, 2H) 5.03-5.4 (2s, 2H) 7.26-7.41 (m, 6H) 8.35-8.40 (m, 3H) 9.73 (bs, 1H) 11.76 (bs, 1H) 12.60 (bs, 1H).

Example 97

(5Z)-2-[(4-bromobenzyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 4.70 (s, 2H) 7.24 (m, 2H) 7.43 (d, J=8.1 Hz, 2H) 7.62 (d, J=8.1 Hz, 2H) 8.37 (m, 3H) 9.63 (s, 1H) 12.12 (bs, 1H) 12.62 (bs, 1H).

Example 98

(5Z)-2-[(2,3-dihydro-1H-inden-2-ylmethyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 3.09-3.41 (m, 4H) 4.59 (bs, 1H) 7.20-7.30 (m, 5H) 8.29-8.40 (m, 3H) 9.7 (bs, 1H) 11.7 (bs, 1H) 12.7 (s, 1H).

Example 99

(5Z)-2-[(1-benzothien-2-ylmethyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 4.98 (s, 2H) 7.09-7.19 (m, 2H) 7.37 (dd, J=8.11, J=7.57 Hz, 2H) 7.51 (s, 1H) 7.86-7.95 (2d, J=8.17, J=7.57 Hz, 2H) 8.33 (s, 2H) 8.46 (s, 1H) 11.54 (bs, 1H) 12.53 (bs, 1H).

Example 100

(5Z)-2-{[(1S,2R,5S)-2-isopropyl-5-methylcyclohexyl]amino}-5-(1H-pyrrolo[2,3-b]pyridin-3-ylmethylene)-3,5-dihydro-4H-imidazol-4-one trifluoroacetate $^1$H-NMR (DMSOd$_6$), δ ppm: 0.9-2.1 (m, 17H) 7.20 (bs, 2H) 8.14 (s, 1H) 8.32 (m, 2H) 11.34 (bs, 1H) 12.46 (bs, 1H).

Example 101

(5Z)-2-(bicyclo[2.2.1]hept-2-ylamino)-5-(1H-pyrrolo[2,3-b]pyridin-3-ylmethylene)-3,5-dihydro-4H-imidazol4-one trifluoroacetate $^1$H-NMR (DMSOd$_6$), δ ppm: 1.16-2.25 (m, 10H) 4.10 (bs, 2H) 7.0 (s, 1H) 7.21 (m, 1H) 8.19 (s, 1H) 8.32-8.43 (m, 2H) 9.5 (bs, 1H) 12.48 (bs, 1H).

Example 102

(5Z)-2-{[3-fluoro-5-(trifluoromethyl)benzyl]amino}-5-(1H-pyrrolo[2,3-b]pyridin-3-ylmethylene)-3,5-dihydro-4H-imidazol-4-one trifluoroacetate $^1$H-NMR (DMSOd$_6$), δ ppm: 4.72 (s, 2H) 6.82 (bs, 1H) 7.13 (s, 1H) 7.62-7.69 (m, 2H) 8.18 (s, 1H) 8.28 (d, 1H) 8.52 (bs, 1H) 10.74 (bs, 1H) 12.17 (bs, 1H).

Example 103

(5Z)-2-[(1-ethylpropyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 0.94 (m, 6H) 1.60 (m, 4H) 3.38 (m, 1H) 7.19(s, 1H) 7.25 (s, 1H) 8.36 (m, 3H) 9.34 (bs, 1H) 11.81 (bs, 1H) 12.63 (s, 1H).

Example 104

(5Z)-5-(1H-pyrrolo[2,3-b]pyridin-3-ylmethylene)-2-[(2,2,6,6-tetramethylpiperidin-4-yl)amino]-3,5-dihydro-4H-imidazol-4-one dihydrochloride $^1$H-NMR (DMSOd$_6$), δ ppm: 1.48 (d, 12H) 1.71-2.09 (2t, 4H) 4.25 (bs, 1H) 7.24 (m, 2H) 8.36 (m, 3H) 9.28 (bs, 2H) 9.74 (bs, 1H) 11.98(bs, 1H) 12.63 (bs, 1H).

Example 105

(5Z)-2-(adamantanamino)-5-(1H-pyrrolo[2,3-b]pyridin-3-ylmethylene)-3,5-dihydro-4H-imidazol-4-one dihydrochloride $^1$H-NMR (DMSOd$_6$), δ ppm: 1.65-2.1 (m, 14H) 3.93 (s, 1H) 7.18-7.25 (m, 3H) 8.41 (m, 3H) 9.81 (s, 1H) 12.11 (bs, 1H) 12.67 (bs, 1H).

Example 106

(5Z)-2-(isopropylamino)-5-(1H-pyrrolo[2,3-b]pyridin-3-ylmethylene)-3,5-dihydro-4H-imidazol-4-one dihydrochloride $^1$H-NMR (DMSOd$_6$), δ ppm: 1.30 (d, 6H) 3.96 (s, 1H) 7.18 (s, 1H) 7.27 (m, 1H) 8.36 (m, 3H) 9.34 (bs, 1H) 11.80 (bs, 1H) 12.63 (s, 1H).

Example 107

(5Z)-2-{([3-(dimethylamino)-2,2-dimethylpropyl]amino}-5-(1H-pyrrolo[2,3-b]pyridin-3-ylmethylene)-3,5-dihydro-4H-imidazol-4-one dihydrochloride $^1$H-NMR (DMSOd$_6$), δ ppm: 1.16 (s, 6H) 2.87 (s, 6H) 7.23 (m, 2H) 8.37 (m, 3H) 9.62 (bs, 1H) 12.65 (bs, 1H).

Example 108

(5Z)-2-[(3R)-1-azabicyclo[2.2.2]oct-3-ylamino]-5-(1H-pyrrolo[2,3-b]pyridin-3-ylmethylene)-3,5-dihydro-4H-imidazol-4-one hydrochloride trifluoroacetate $^1$H-NMR (DMSOd$_6$), δ ppm: 1.65-2.4 (m, 5H) 4.31 (bs, 1H) 6.80 (s, 1H) 7.17 (m, 1H) 8.19 (s, 1H) 8.29 (m, 1H) 8.61 (bs, 1H) 9.45 (s, 1H) 10.68 (bs, 1H).

Example 109

(5Z)-2-{[(1R,5S)-8-methyl-8-azabicyclo[3.2.1]oct-3-yl]amino}-5-(1H-pyrrolo[2,3-b]pyridin-3-ylmethylene)-3,5-dihydro-4H-imidazol-4-one hydrochloride trifluoroacetate $^1$H-NMR (DMSOd$_6$), δ ppm: 1.85-2.4 (m, 8H) 2.70 (s, 3H) 3.38-4.0 (m, 3H) 6.84 (bs, 1H) 7.18 (m, 1H) 8.19 (s, 1H) 8.30 (s, 1H) 8.62 (bs, 2H) 9.54 (bs, 1H) 12.21 (bs, 1H).

Example 110

(5Z)-2-[(3S)-1-azabicyclo[2.2.2]oct-3-ylamino]-5-(1H-pyrrolo[2,3-b]pyridin-3-ylmethylene)-3,5-dihydro-4H-imidazol-4-one hydrochloride trifluoroacetate $^1$H-NMR (DMSOd$_6$), δ ppm: 1.65-2.4 (m, 5H) 3.39 (m, 6H) 4.31 (s, 1H) 6.80 (s, 1H) 7.17 (dd, J=7.6, J=4.6 Hz, 1H) 8.20 (s, 1H) 8.29 (d, J=4.6 Hz, 1H) 8.60 (bs, 1H) 9.49 (s, 1H) 12.15 (s, 1H).

Example 111

(5Z)-2-{[(1S)-1-phenyl-2-pyrrolidin-1-ylethyl]amino}-5-(1H-pyrrolo[2,3-b]pyridin-3-ylmethylene)-3,5-dihydro-4H-imidazol-4-one hydrochloride trifluoroacetate $^1$H-NMR (DMSOd$_6$), δ ppm: 1.98 (s, 4H) 3.40 (m, 6H) 5.49 (bs, 1H) 6.75 (s, 1H) 7.15 (dd, J=4.7, J=3.29 Hz, 1H) 7.37 (t, J=7.32 Hz, 1H) 7.46 (t, J=7.32 Hz, 2H) 7.20 Hz, 2H) 8.18 (s, 1H) 8.28 (d, J=4.7 Hz, 1H) 8.58 (bs, 1H).

Example 112

(5Z)-2-[(4-hydroxycyclohexyl)amino]-5-(1H-pyrrolo[2,3-b]pyridin-3-ylmethylene)-3,5-dihydro-4H-imidazol-4-one $^1$H-NMR (DMSOd$_6$), δ ppm: 1.77-2.2 (m, 8H) 3.34 (s, 2H) 4.58 (s, 1H) 6.61 (s, 1H) 7.11 (dd, J=4.7, J=3.3 Hz, 1H) 7.15-7.69 (m, 1H) 8.18 (s, 1H) 8.25 (d, J=3.3 Hz, 1H) 8.68 (d, J=4.7 Hz, 1H) 10.36 (bs, 1H) 11.92 (s, 1H).

Example 113

(5Z)-2-{[(2S)-2-hydroxycyclohexyl]amino}-5-(1H-pyrrolo[2,3-b]pyridin-3-ylmethylene)-3,5-dihydro-4H-imidazol-4-one $^1$H-NMR (DMSOd$_6$), δ ppm: 1.29-2.35 (m, 8H) 3.35 (s, 2H) 4.89 (s, 1H) 6.61 (s, 1H) 7.11 (m, 1H) 8.18 (s, 1H) 8.24 (d, J=3.3 Hz, 1H) 8.63(d, J=4.7 Hz, 1H) 10.32 (bs, 1H) 11.92 (s, 1H).

Example 114

(5Z)-2-{[(1S,2S,3R,4R)-3-(hydroxymethyl)bicyclo[2.2.1]hept-2-yl]amino}-5-(1H-pyrrolo[2,3-b]pyridin-3-ylmethylene)-3,5-dihydro-4H-imidazol-4-one dihydrochloride $^1$H-NMR (DMSOd$_6$), δ ppm: 1.2-2.35 (m, 9H) 3.39 (m, 2H) 3.85 (m, 1H) 7.17 (s, 1H) 7.23 (m, 1H) 8.32-8.40 (m, 3H) 9.39 (s, 1H) 11.78 (bs, 1H) 12.66 (s, 1H).

Example 115

(5Z)-2-(adamantylmethylamino)-5-(1H-pyrrolo[2,3-b]pyridin-3-ylmethylene)-3,5-dihydro-4H-imidazol-4-one dihydrochloride $^1$H-NMR (DMSOd$_6$), δ ppm: 1.57-2.1 (m, 12H) 3.39 (m, 4H) 7.19-7.26 (m, 2H) 8.36-8.40 (m, 3H) 9.40 (bs, 1H) 11.97 (bs, 1H) 12.67 (s, 1H).

Example 116

(5Z)-2-[(1S,2R,4R)-bicyclo[2.2.1]hept-2-ylamino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 1.2-1.95 (m, 8H) 2.34 (s, 2H) 3.58 (s, 1H) 7.18 (s, 1H) 7.23 (dd, J=7.93; J=4.76 Hz, 1H) 8.31 (s, 1H) 8.36(d, J=4.7 Hz, 1H) 8.40 (d, J=8.01 Hz, 1H) 9.59 (bs, 1H) 11.73 (bs, 1H) 12.64 (s, 1H).

Example 117

(5Z)-2-{[(1R)-1-phenylethyl]amino}-5-(1H-pyrrolo[2,3-b]pyridin-3-ylmethylene)-3,5-dihydro-4H-imidazol-4-one dihydrochloride $^1$H-NMR (DMSOd$_6$), δ ppm: 1.61 (d, 3H) 5.07 (bs, 1H) 7.23-7.51 (m, 7H) 8.32-8.38(m, 3H) 9.98(bs, 1H) 11.82 (bs, 1H) 12.62 (bs, 1H).

Example 118

(5Z)-5-(1H-pyrrolo[2,3-b]pyridin-3-ylmethylene)-2-{[(1R,4R)-1,7,7-trimethylbicyclo[2.2.1]hept-2-yl]amino}-3,5-dihydro-4H-imidazol-4-one dihydrochloride $^1$H-NMR (DMSOd$_6$), δ ppm: 0.86-1.74 (m, 15H) 3.99 (s, 1H) 4.42(s, 1H) 7.15-7.28 (m, 2H) 8.35-8.38 (m, 3H) 9.64 (bs, 1H) 11.88(bs, 1H) 12.65 (bs, 1H).

Example 119

(5Z)-2-{[(1R,2S,3R,4S)-3-(hydroxymethyl)bicyclo[2.2.1]hept-2-yl]amino}-5(1H-pyrrolo[2,3-b]pyridin-3-ylmethylene)-3,5-dihydro-4H-imidazol-4-one dihydrochloride $^1$H-NMR (DMSOd$_6$), δ ppm: 1.4-2.5 (m, 9H) 3.41 (m, 2H) 4.14 (s, 1H) 7.18 (s, 1H) 7.23 (m, 1H) 8.42 (m, 3H) 9.52 (s, 1H) 11.97 (bs, 1H) 12.68 (bs, 1H).

Example 120

(5Z)-5-(1H-pyrrolo[2,3-b]pyridin-3-ylmethylene)-2-{[(1R,2R,3R,5S)-2,6,6-trimethylbicyclo[3.1.1]hept-3-yl]amino}-3,5-dihydro-4H-imidazol-4-one dihydrochloride $^1$H-NMR (DMSOd$_6$), δ ppm: 1.06-1.25 (m, 11H) 1.79-2.55 (m, 5H) 4.04 (s, 1H) 7.18-7.25 (m, 2H) 8.32-8.39 (m, 3H) 9.74 (bs, 1H) 11.74 (bs, 1H) 12.63 (bs, 1H).

Example 121

(5Z)-2-{[(1S)-2-(4-methylpiperazin-1-yl)-1-phenylethyl]amino}-5-(1H-pyrrolo[2,3-b]pyridin-3-ylmethylene)-3,5-dihydro-4H-imidazol-4-one dihydrochloride $^1$H-NMR (DMSOd$_6$), δ ppm: 2.6 (s, 3H) 3.5-3.7 (m, 10H) 7.18-7.55 (m, 6H) 8.32-8.5 (m, 3H) 9.0 (bs, 1H) 12.53 (bs, 1H).

Example 122

(5Z)-2-{[(1S)-1-phenyl-2-piperidin-1-ylethyl]amino}-5-(1H-pyrrolo[2,3-b]pyridin-3-ylmethylene)-3,5-dihydro-4H-imidazol-4-one dihydrochloride $^1$H-NMR (DMSOd$_6$), δ ppm: 1.83 (s, 6H) 3.5-3.7 (m, 6H) 5.7 (bs, 1H) 6.89 (bs, 1H) 7.22 (dd, J=8.05; J=4.76 Hz, 1H) 7.51 (t, J=7.81 Hz, 3H) 7.59 (d, J=7.81 Hz, 2H) 8.42 (d, J=4.87 Hz, 2H) 8.5 (bs, 1H) 9.95 (bs, 1H) 12.43 (bs, 1H).

Example 123

(5Z)-2-{[(1S)-2-morpholin-4-yl-1-phenylethyl] amino}-5-(1H-pyrrolo[2,3-b]pyridin-3-ylmethylene)-3,5-dihydro-4H-imidazol-4-one dihydrochloride $^1$H-NMR (DMSOd$_6$), δ (ppm): 3.5-4.0 (m, 10H) 5.7 (bs, 1H ) 6.89 (bs, 1H) 7.3 (dd, J=7.80; J=4.63 Hz, 1H) 7.41 (d, J=7.19 Hz, 1H) 7.49 (t, J=7.81 Hz, 2H) 7.7 (d, J=7.31 Hz, 2H) 8.25-8.4(m, 3H)

Example 124

(5Z)-2-{[1-(3-fluorophenyl)ethyl]amino}-5-(1H-pyrrolo[2,3-b]pyridin-3-ylmethylene)-3,5-dihydro-4H-imidazol-4-one dihydrochloride $^1$H-NMR (DMSOd$_6$), δ ppm: 1.61 (d, 3H) 5.10 (bs, 1H) 7.2-7.51 (m, 6H) 8.32-8.38 (m, 3H) 10.0 (bs, 1H) 12.60 (bs, 1H).

Example 125

(5Z)-2-[(1,2,2,6,6-pentamethylpiperidin-4-yl) amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 1.45 (d, 12H) 2.1-2.3 (m, 4H) 4.2 (bs, 1H) 7.2 (m, 2H) 8.32-8.38 (m, 3H) 8.8 (s, 1H) 9.7 (bs, 1H).

Example 126

(5Z)-2-[(2-hydroxy-1-phenylethyl)amino]-5-(1H-pyrrolo[2,3-b]pyridin-3-ylmethylene)-3,5-dihydro-4H-imidazol-4-one dihydrochloride $^1$H-NMR (DMSOd$_6$), δ ppm: 3.85 (m, 2H) 4.8 (s, 1H) 7.1-7.5 (m, 5H) 8.3-8.38 (m, 3H) 9.8 (s, 1H) 11.8(bs, 1H) 12.6(bs, 1H).

Example 127

(5Z)-2-[(3-hydroxy-1-phenylpropyl)amino-5-(1H-pyrrolo[2,3-b]pyridin-3-ylmethylene)-3,5-dihydro-4H-imidazol-4-one dihydrochloride $^1$H-NMR (DMSOd$_6$), δ ppm: 2.09 (m, 2H) 5.11 (bs, 1H) 7.1-7.5 (m, 5H) 8.2-8.45 (m, 3H) 9.95 (bs, 1H) 11.8 (bs, 1H) 12.6 (bs, 1H).

Example 128

(5Z)-2-{[(1R)-1-phenyl-2-pyrrolidin-1-ylethyl] amino}-5-(1H-pyrrolo[2,3-b]pyridin-3-ylmethylene)-3,5-dihydro-4H-imidazol-4-one $^1$H-NMR (DMSOd$_6$), δ ppm: 1.98 (s, 4H) 3.40 (m, 6H) 5.49 (bs, 1H) 6.75 (m, 1H) 7.15(dd, J=4.7, J=3.29 Hz, 1H) 7.37 (t, J=7.32 Hz, 1H) 7.46 (t, J=7.32 Hz, 2H) 7.54 (d, J=7.20 Hz, 2H) 8.18 (s, 1H) 8.28 (d, J=4.7 Hz, 1H) 8.58 (bs, 1H).

Example 129

(5Z)-2-{[(1S)-1-phenylethyl]amino}-5-(1H-pyrrolo[2,3-b]pyridin-3-ylmethylene)-3,5-dihydro-4H-imidazol-4-one dihydrochloride $^1$H-NMR (DMSOd$_6$), δ ppm: 1.63 (d, 3H) 5.08 (bs, 1H) 7.20-7.52 (m, 6H) 8.38 (m, 3H) 10.00 (bs, 1H) 11.88 (bs, 1H) 12.65 (bs, 1H)

Example 129

(5Z)-2-{[(1S)-1-phenylethyl]amino}-5-(1H-pyrrolo[2,3-b]pyridin-3-ylmethylene)-3,5-dihydro-4H-imidazol-4-one dihydrochloride A mixture of 110 mg (0.33 mmole) of 2-(benzylthio)-5-(1H-pyrrolo[2,3-b]pyridin-3-ylmethylene)-3,5-dihydro-4H-imidazol-4-one and 0.7 mL (5.5 mmole) of (−)-1-phenyl-ethylamine in 1 mL of anhydrous ethanol were stirred at 110° C. overnight in a sealed tube. After evaporation of the solution in order to eliminate the excess amine, the residue was washed with diethyl ether and dried in a vacuum oven. The product was then salified by dissolution in 3 mL of methanol and addition of 0.3 mL of 4M HCl in dioxane. After 1 hour evaporation of the solution gave 100 mg (80% yield) of the desired product.

$^1$H-NMR (DMSOd$_6$), δ ppm: 1.63 (d, 3H) 5.08 (bs, 1H) 7.20-7.52 (m, 6H) 8.38 (m, 3H) 10.00 (bs, 1H) 11.88 (bs, 1H) 12.65 (bs, 1H).

Example 130

(5Z)-2-(benzylthio)-5-(1H-pyrrolo[2,3-b]pyridin-3-ylmethylene)-3,5-dihydro-4H-imidazol-4-one A mixture of azaindole-3-carboxaldehyde (6 g, 41 mmol), thiohydantoin (4.75 g, 41 mmol) and sodium acetate (11.3 g, 138 mmol) in glacial acetic acid (60 mL) was refluxed under stirring for 5 h. After cooling in ice bath the precipitate was filtered and washed with 95% ethanol. After drying, 5-(1H-pyrrolo[2,3-b]pyridin-3-ylmethylene)-2-thioxoimidazolidin-4-one was obtained as a yellow solid (8.9 g, 36.5 mmol, 89%).

$^1$H-NMR (DMSOd$_6$), δ ppm: 6.8 (s, 1H) 7.2 (m, 1H) 8.25 (m, 2H) 8.58 (d, 1H) 11.8 (s, 1H) 12.15 (s, 1H) 12.4 (s, 1H).

To a solution of 5-(1H-pyrrolo[2,3-b]pyridin-3-ylmethylene)-2-thioxoimidazolidin-4-one (500 mg, 2.05 mmol) in 12.6% aq. NaOH (1 mL) and methanol (5 mL), benzyl bromide (430 mg, 2.5 mmol) was added and the reaction mixture stirred at RT for 18 h. Most of the solvent was distilled out and the precipitate was filtered and washed first with water, then with diethylether and dried. The crude material was purified by flash chromatography on silica gel (eluant: dichloromethane/methanol 15:1). Obtained the desired (5Z)-2-(benzylthio)-5-(1H-pyrrolo[2,3-b]pyridin-3-ylmethylene)-3,5-dihydro-4H-imidazol-4-one, as a yellow solid (700 mg, 2 mmol).

$^1$H-NMR (DMSOd$_6$), δ ppm: 4.63 (s, 2H) 7.12 (s, 1H) 7.21 (dd, J=7.93, 4.76 Hz, 1H) 7.26-7.33 (m, 1H) 7.37 (dd, J=8.54, 7.07 Hz, 2H) 7.48-7.56 (m, 2H) 8.32 (dd, J=4.76, 1.59 Hz, 1H) 8.45 (d, J=2.56 Hz, 1H) 8.79 (d, J=7.68 Hz, 1H) 12.44 (s, 1H).

Example 131

(5Z)-2-(benzylamino)-5-(1H-pyrrolo[2,3-b]pyridin-3-ylmethylene)-1,3-thiazol-4(5H)-one hydrochloride A mixture of azaindole-3-carboxaldehyde (6 g, 41 mmol), rhodanine (4.96 g, 41 mmol) and sodium acetate (11.3 g, 138 mmol) in glacial acetic acid (60 mL) was refluxed under stirring for 5 h. After cooling in ice bath the precipitate was filtered and washed with 95% ethanol. After drying, (5Z)-5-(1H-pyrrolo[2,3-b]pyridin-3-ylmethylene)-2-thioxo-1,3-thiazolidin-4-one was obtained as a yellow solid (9.5 g, 36.5 mmol, 88%).

$^1$H-NMR (DMSOd$_6$), δ ppm: 7.28 (m, 1H) 7.96 (m, 2H) 8.38 (m, 2H) 9.20 (d, 1H) 12.82 (2s, 1H) 13.42 (2 s, 1H).

To a solution of 5-(1H-pyrrolo[2,3-b]pyridin-3-ylmethylene)-2-thioxo-1,3-thiazolidin-4-one (8 g, 30.6 mmol) in 12.6% aq. NaOH (12 mL) and methanol (80 mL), methyl iodide (2.25 mL, 36 mmol) was added and the reaction mixture stirred at RT for 4 h. Most of the solvent was distilled off and the precipitate was filtered and washed first with water, then with diethylether. The washings were concentrated and extracted with dichloromethane, dried over sodium sulphate and joined to the first solid crop. The whole crop was suspended in methanol, stirred 30', filtered and dried to yield 2-(methylthio)-5-(1H-pyrrolo[2,3-b]pyridin-3-ylmethylene)-1,3-thiazol-4(5H)-one as a yellow solid (8.15 g, 29.5 mmol, 96%).

$^1$H-NMR (DMSOd$_6$), δ ppm: 2.84 (2s, 1H) 7.89 (m, 1H) 7.99 (d, 1H) 8.13 (s, 1H) 8.27 (s, 1H) 8.38 (m, 2H) 8.45-4.50 (2d, 1H) 9.44 (s, 1H) 12.81 (2 s, 1H).

To a suspension of 2-(methylthio)-5-(1H-pyrrolo[2,3-b]pyridin-3-ylmethylene)-1,3-thiazol-4(5H)-one (0.2 g, 0.77 mmol) in absolute ethanol (5 mL) benzylamine (1.05 mL, 9.7 mmol) was added and the mixture was refluxed overnight. After cooling to RT the precipitate was filtered, suspended in methanol (2 mL), 4M HCl in dioxane (0.5 mL) was added and the mixture stirred at RT for 30'. The yellow precipitate was filtered, washed with little methanol and then with diethylether. Obtained (5Z)-2-(benzylamino)-5-(1H-pyrrolo[2,3-b]pyridin-3-ylmethylene)-1,3-thiazol-4(5H)-one.HCl as a yellow solid (0.2 g, 0.59 mmol, 76%).

$^1$H-NMR (DMSOd$_6$), δ ppm: 4.69 (s, 2H) 7.26 (dd, J=7.81; J=4.88 Hz, 1H) 7.28-7.39 (m, 5H) 7.71-7.84 (m, 1H) 7.88 (s, 1H) 8.40 (m, 2H) 9.99 (bs, 1H)

Examples 132-136

By employing the above described procedure in Example 131 the following compounds of examples 132-136 were also prepared:

Example 132

(5Z)-2-{[(1S)-1-phenylethyl]amino}-5-(1H-pyrrolo[2,3-b]pyridin-3-ylmethylene)-1,3-thiazol-4(5H)-one hydrochloride $^1$H-NMR (DMSOd$_6$), δ ppm: 1.57 (d, 3H) 5.31 (s, 1H) 7.26 (dd, J=7.81; J=4.88 Hz, 1H) 7.28-7.41 (m, 5H) 7.70 (s, 1H) 7.85 (s, 1H) 8.37 (m, 2H) 10.00 (bs, 1H) 12.49 (s, 1H).

Example 133

(5Z)-2-[4-(2-hydroxyethyl)piperazin-1-yl]-5-(1H-pyrrolo[2,3-b]pyridin-3-ylmethylene)-1,3-thiazol-4(5H)-one dihydrochloride $^1$H-NMR (DMSOd$_6$), δ ppm: 3.27-4.1 (m, 12H) 4.72 (bs, 1H) 7.24 (m, 1H) 7.84 (s, 1H) 7.96 (s, 1H) 8.37 (m, 2H) 10.4 (bs, 1H) 12.64 (s, 1H).

Example 134

(5Z)-2-(isopropylamino)-5-(1H-pyrrolo[2,3-b]pyridin-3-ylmethylene)-1,3-thiazol-4(5H)-one dihydrochloride $^1$H-NMR (DMSOd$_6$), δ ppm: 1.26 (d, 6H) 4.21 (bs, 1H) 7.27 (m, 1H) 7.69 (s, 1H) 7.86 (s, 1H) 8.38 (m, 2H) 9.55 (bs, 1H) 12.49 (s, 1H).

Example 135

(5Z)-2-[(3R)-1-azabicyclo[2.2.2]oct-3-ylamino]-5-(1H-pyrrolo[2,3-b]pyridin-3-ylmethylene)-1,3-thiazol-4(5H)-one dihydrochloride $^1$H-NMR (DMSOd$_6$), δ ppm: 2.0-3.7 (m, 11H) 4.45 (bs, 1H) 7.26 (m, 1H) 7.73 (s, 1H) 7.90 (s, 1H) 8.38 (m, 2H) 10.06 (bs, 1H) 12.54 (s, 1H).

Example 136

(5Z)-2-[(2-furylmethyl)amino]-5-(1H-pyrrolo[2,3-b]pyridin-3-ylmethylene)-1,3-thiazol-4(5H)-one dihydrochloride $^1$H-NMR (DMSOd$_6$), δ ppm: 4.75 (s, 2H) 6.47 (m, 2H) 7.27 (dd, J=7.93; 4.76 Hz, 1H) 7.68 (m, 2H) 7.88 (s, 1H) 8.38 (m, 2H) 9.97 (bs, 1H) 12.51 (s, 1H).

Example 137

(5Z)-N-(3-{[2-(benzylamino)-5-oxo-1,5-dihydro-4H-imidazol-4-ylidene]methyl}-1H-pyrrolo[2,3-b]pyridin-5-yl)acetamide hydrochloride A mixture of 1H-pyrrolo[2,3-b]pyridine (5 g, 42.3 mmol), grounded anhydrous potassium carbonate (17.54 g, 126.9 mmol) and benzenesulfonylchloride (10.85 mL, 84.6 mmol) in anhydrous acetonitrile (100 mL) was refluxed for 2 h.

After cooling the reaction mixture was filtered and the filtrate was poured into 2N HCl (150 mL) with stirring. The solution was diluted by adding brine (300 mL) and was extracted with ethyl acetate (3×200 mL). The organic layers were washed with brine (2×200 mL), dried over sodium sulfate and concentrated. The residue was treated with ether (100 mL) and n-hexane (400 mL), the volume was reduced under vacuum, the precipitate was filtered and washed with n-hexane. Obtained 1-(phenylsulfonyl)-1H-pyrrolo[2,3-b]pyridine as a solid (10 g, 38.7 mmol, 91% yield).

1H NMR (400 MHz, DMSOd$_6$) δ ppm: 6.85 (d, J=4.02 Hz, 1H) 7.32 (dd, J=7.93, 4.76 Hz, 1H) 7.59-7.68 (m, 2H) 7.70-7.76 (m, 1H) 7.92 (d, J=4.02 Hz, 1H) 8.07 (dd, J=7.86, 1.65 Hz, 1H) 8.10-8.15 (m, 2H) 8.38 (dd, J=4.76, 1.59 Hz, 1H).

To a solution of 1-(phenylsulfonyl)-1H-pyrrolo[2,3-b]pyridine (10 g, 38.7 mmol) in dry dichloromethane (200 mL), cooled to −5° C., under stirring and argon, a solution of tetrabutylammonium nitrate (14.75 g, 48.4 mmol) in dry dichloromethane (200 mL) and trifluoroacetic anhydride (7 mL) was slowly added (in about 30'), while maintaining the internal temperature between −5 and 0° C. After addition the reaction mixture was stirred at this temperature for 30', cold water was added and the organic layer was washed with water (3×200 mL), dried over sodium sulfate and concentrated. The crude product was purified by flash column chromatography (silica, eluant: dichloromethane/n-hexane 3:2, then only dichloromethane). The desired 5-nitro-1-(phenylsulfonyl)-1H-pyrrolo[2,3-b]pyridine was obtained as a solid (9 g, 29.7 mmol, 76% yield).

$^1$H-NMR (DMSOd$_6$), δ ppm: 7.07 (d, J=4.02 Hz, 1H) 7.67 (M, 2H) 7.78 (m, 1H) 8.16-8.21 (m, 3H) 8.97 (d, J=2.56 Hz, 1H) 9.21 (d, J=2.56 Hz, 1H).

To a stirred suspension of 5-nitro-1-(phenylsulfonyl)-1H-pyrrolo[2,3-b]pyridine (10.2 g, 33 mmol) in methanol (250 mL) powdered sodium hydroxide (2 g, 50 mmol) was added. After stirring at room temperature for 30' more powdered sodium hydroxide (2 g, 50 mmol) and dichloromethane (50 mL) were added and stirring was prolonged for additional 30'. After concentration, a solution of 2N HCl (50 mL) and water (200 mL) was added and the obtained mixture was filtered. The yellow cake was washed with water and dried to give 5-nitro-1H-pyrrolo[2,3-b]pyridine (4.6 g, 28.2 mmol, 85% yield).

$^1$H-NMR (DMSOd$_6$), δ ppm: 6.78 (dd, J=3.50, 1.83 Hz, 1H) 7.79 (dd, J=3.35, 2.59 Hz, 1H) 8.90-8.92 (m, 1H) 9.13 (d, J=2.59 Hz, 1H) 12.05-12.92 (m, 1H).

To a solution of 5-nitro-1H-pyrrolo[2,3-b]pyridine (0.4 g, 2.45 mmol) in ethyl acetate (100 mL) 5% Pd—C (0.3 g) was added and the mixture subdued to hydrogenation (30 psi) in a Parr apparatus. After 4 hours the catalyst was filtered off through celite, the cake was washed with ethyl acetate and then with a mixture of dichloromethane/methanol 4:1. 1H-pyrrolo[2,3-b]pyridine-5-amine (5-aminoazaindole) was obtained in 95% yield (0.31 g, 2.33 mmol).

$^1$H-NMR (DMSOd$_6$), δ ppm: 4.62 (s, 2H) 6.17 (dd, J=3.29, 1.95 Hz, 1H) 7.10 (dd, J=2.50, 0.55 Hz, 1H) 7.24 (t, J=2.87 Hz, 1H) 7.72 (d, J=2.56 Hz, 1H) 11.04 (s, 1H).

Into a solution of 5-aminoazaindole (0.6 g, 4.5 mmol) in dry DMF (11 mL) N-[(1H-1,2,3-benzotriazol-1-yloxy)(dimethylamino)methylene]-N-methylmethanaminium tetrafluoroborate (TBTU, 1.45 g, 9 mmol), 1-hydroxybenzotriazole (HOBt, 0.69 g, 9 mmol) and glacial AcOH (260 micro), diisopropylethylamine (DIPEA, 3.12 mL, 18 mmol) was slowly dropped in ca. 30' under stirring. The reaction mixture was stirred at room temperature for 18 h, concentrated and the residue was purified by flash chromatography eluting with dichloromethane/MeOH 10:1. The desired 1H-pyrrolo[2,3-b]pyridin-5-ylacetamide (title compound) was obtained in 95% yield (0.78 g, 4.2 mmol).

$^1$H-NMR (DMSOd$_6$), δ ppm: 2.07 (s, 3H) 6.41 (m, 1H) 7.43 (t, J=2.93 Hz, 1H) 8.22 (d, J=2.07 Hz, 1H) 8.26 (d, J=2.32 Hz, 1H) 9.92 (s, 1H) 11.51 (s, 1H).

Example 138

By employing the above described procedure in Example 137, (5Z)-1-methyl-N-1H-pyrrolo[2,3-b]pyridin-5-ylpiperidine-4-carboxamide was also prepared:

$^1$H-NMR (DMSOd$_6$), δ ppm: 1.9 (m, 2H) 2.07 (d, J=13.90 Hz, 2H) 2.55-2.73 (m, 1H) 2.80 (d, J=3.90 Hz, 3H) 3.00 (dd, J=10.73, 10.24 Hz, 2H) 3.51 (d, J=12.19 Hz, 2H) 6.42 (s, J=3.41, 1.83 Hz, 1H) 7.42-7.48 (m, 1H) 8.26 (2d, J=28.66, 2.19 Hz, 2H) 8.30 (d, J=2.32 Hz, 1H) 10.07 (s, 1H) 11.54 (s, 1H).

Example 139

(5Z)-N-(3-{[2-(benzylamino)-5-oxo-1,5-dihydro-4H-imidazol-4-ylidene]methyl}-1H-pyrrolo[2,3-b]pyridin-5-yl)acetamide hydrochloride N-(3-{2[2-benzylamino-5-oxo-1,5, -dihydro-4H-imidazyl-4-ylidene]methyl}-1H-pyrrol, [2,3-b] pyridine-5-yl acetamide hydrochloride a mixture of 1H-pyrrolo[2,3-b]pyridin-5-ylacetamide (0.79 9, 4.5 mmol) and hexamethylenetetramine (0.95 9, 6.75 mmol) in 30% AcOH (21 mL) was warmed at 100° C. for 4 h. After cooling, the mixture was diluted with water (10 mL), the precipitate was filtered, washed with water and dried. Obtained N-(3-formyl-1H-pyrrolo[2,3-b]pyridin-5-yl)acetamide (0.7 g, 3.45 mmol, 76%).

$^1$H NMR (400 MHz, DMSOd$_6$) δ ppm: 2.10 (s, 3H) 8.43 (d, J=3.17 Hz, 1H) 8.50 (d, J=2.44 Hz, 1H) 8.73 (d, J=2.32 Hz, 1H) 9.9 (s, 1H) 10.12 (s, 1H) 12.60 (s, 1H).

A mixture of N-(3-formyl-1H-pyrrolo[2,3-b]pyridin-5-yl)acetamide (0.2 g, 1 mmol), thiohydantoin (0.116 g, 1 mmol), sodium acetate (0.246 g, 3 mmol), glacial AcOH (5 mL) was warmed at 125° C. for 3 h. After cooling, water (5 mL) was added, the precipitate was filtered, washed with water and dried. The so obtained N-{3-[(5-oxo-2-thioxoimidazolidin-4-ylidene)methyl]-1H-pyrrolo[2,3-b]pyridin-5-yl}acetamide(0.24 g, 0.79 mmol, 80% yield), N-{3-[(5-oxo-2-thioxoimidazolidin-4-ylidene)methyl]-1H-pyrrolo[2,3-b]pyridin-5-yl)acetamide (0.24 g, 0.79 mmol), 12.6% NaOH (0.32 mL), MeOH (4 mL) and methyl iodide (0.2 mL, 3.2 mmol) were stirred at room temperature for 3 h under argon. After partial concentration, water (5 mL) was added, the precipitate was filtered and dried. N-(3-[2-(methylthio)-5-oxo-1,5-dihydro-4H-imidazol-4-ylidene]methyl}-1H-pyrrolo[2,3-b]pyridin-5-yl)acetamide was obtained as a solid (0.22 g, 0.7 mmol, 87%).

N-(3-{[2-(methylthio)-5-oxo-1,5-dihydro-4H-imidazol-4-ylidene]methyl}-1H-pyrrolo[2,3-b]pyridin-5-yl)acetamide (0.2 g, 0.635 mmol), benzylamine (0.5 mL, 4.58 mmol) and EtOH (3 mL) in a closed tube were warmed at 110° C. for 4 h. After cooling, the precipitate was filtered, washed with ethanol and dried to yield the desired compound (0.22 g, 0.59 mmol, 92%). The compound was dissolved in methanol, treated with 4 N hydrochloric acid in dioxane and diluted with ethyl acetate until precipitation of the hydrochloride salt that was filtered, thus affording the title compound, N-(3-{[2-(benzylamino)-5-oxo-1,5-dihydro-4H-imidazol-4-ylidene]methyl}-1H-pyrrolo[2,3-b]pyridin-5-yl)acetamide hydrochloride.

$^1$H-NMR (DMSOd$_6$), δ ppm: 2.11 (s, 3H), 4.72 (s, 2H) 6.98 (bs, 1H) 7.34-7.48 (m, 6H) 8.25-8.70 (m, 3H) 10.1 (s, 1H) 12.5 (bs, 1H).

Example 140

(5Z)-N-(3-{[2-(benzylamino)-5-oxo-1,5-dihydro-4H-imidazol-4-ylidene]methyl}-1H-pyrrolo[2,3-b]pyridin-5-yl)acetamide hydrochloride To a solution of 5-[(5-amino-1H-pyrrolo[2,3-b]pyridin-3-yl)methylene]-2-(benzylamino)-3,5-dihydro-4H-imidazol-4-one (0.149 g, 0.45 mmol), N-[(1H-1,2,3-benzotriazol-1-yloxy)(dimethylamino)methylene]-N- methylmethanaminium tetrafluoroborate (TBTU, 0.145 g, 0.9 mmol), 1-hydroxybenzotriazole (HOBt, 0.07 g, 0.9 mmol) and AcOH (26 micro) in dry DMF (2 mL), diisopropylethylamine (DIPEA, 0.32 mL, 1.8 mmol) was slowly added in ca. 30' with stirring. The reaction mixture was stirred overnight at room temperature. After concentration the residue was purified by flash chromatography on silica gel, eluant: dichloromethane/MeOH 3:1.

The title compound was dissolved in methanol, treated with 4 N hydrochloric acid in dioxane and diluted with ethyl acetate. The precipitate was filtered and washed with ethyl acetate.

$^1$H-NMR (DMSOd$_6$), δ ppm: 2.11 (s, 3H), 4.72 (s, 2H) 6.98 (bs, 1H) 7.34-7.48 (m, 6H) 8.25-8.70 (m, 3H) 10.1 (s, 1H) 12.5 (bs, 1H).

Example 141

(5E+5Z)-2-(benzylamino)-5-[(5nitro-1H-pyrrolo[2,3-b]pyridin-3-yl)methylene]-3,5-dihydro-4H-imidazol one A mixture of 5-nitro azaindole (2 g, 12.2 mmol) and hexamethylenetetramine (2.58 g, 18.4 mmol) in 30% AcOH (18 mL) was warmed at 120° C. for 3 h. The reaction mixture was cooled, water (20 mL) was added, the precipitate was filtered, washed with water and dried. Obtained 5-nitro-1H-pyrrolo[2,3-b]pyridine-3-carbaldehyde, as a solid (2 g, 10.4 mmol, 85%).

$^1$H-NMR (DMSOd$_6$), δ ppm: 8.77 (d, J=2.93 Hz, 1H) 9.12 (d, J=2.56 Hz, 1H) 9.25 (d, J=2.56 Hz, 1H) 10.04 (s, 1H) 13.41 (s, 1H).

A mixture of 5-nitro-1H-pyrrolo[2,3-b]pyridine-3-arbaldehyde (0.57 g, 3 mmol), thiohydantoin (0.35 g, 3 mmol), sodium acetate (0.74 g, 9 mmol), glacial AcOH (15 mL) was warmed at 120° C. for 3 h. After cooling, water (20 mL) was added, the precipitate was filtered, washed with water and dried. 5-[(5-Nitro-1H-pyrrolo[2,3-b]pyridin-3-yl)methylene]-2-thioxoimidazolidin-4-one was obtained (0.6 g, 2.08 mmol, 69%).

A mixture of 5-[(5-nitro-1H-pyrrolo[2,3-b]pyridin-3-yl)methylene]-2-thioxoimidazolidin-4-one (0.6 g, 2.08 mmol), 12.6% NaOH (0.73 mL), MeOH (6 mL) and methyl iodide (0.4 mL, 6.4 mmol) was stirred at room temperature for 4 h under argon. After partial concentration, water (15 mL) was added, the precipitate was filtered and dried. Obtained 2-(methylthio)-5-[(5-nitro-1H-pyrrolo[2,3-b]pyridin-3-yl)methylene]-3,5-dihydro-4H-imidazol-4-one as a solid (0.55 g, 1.8 mmol, 86%).

A mixture of 2-(methylthio)-5-[(5-nitro-1H-pyrrolo[2,3-b]pyridin-3-yl)methylene]-3,5-dihydro-4H-imidazol-4-one (0.175 g, 0.58 mmol) in EtOH (3 mL) and benzylamine (0.88 mL, 8.2 mmol) was warmed at 110° C. in a closed tube for 24 h. Obtained the title compound (0.19 g, 0.52 mmol, 90%), as a mixture of (E) and (Z) isomers that were separated by flash chromatography (silica gel, eluant: dichloromethane/MeOH 3:1).

Examples 142-143

The following compounds of Examples 142-143 were prepared using the techniques described in Example 141:

Example 142

(5Z)-2-(benzylamino)-5-[(5-nitro-1H-pyrrolo[2,3-b]pyridin-3-yl)methylene]-3,5-dihydro-4H-imidazol one $^1$H-NMR (DMSOd$_6$), δ ppm: 4.73 (s, 2H) 6.80 (s, 1H) 7.25-7.45 (s, 5H) 8.28 (s, 1H) 9.08-9.18 (m, 1H) 10.24 (s, 1H) 12.83 (s, 1H).

Example 143

(5E)-2-(benzylamino)-5-[(5-nitro-1H-pyrrolo[2,3-b]pyridin-3-yl)methylene]-3,5-dihydro-4H-imidazol one $^1$H-NMR (DMSOd$_6$), δ ppm: 4.93 (s, 2H), 7.17 (s, 1H) 7.3-7.42 (m, 5H) 8.45 (d, J=2.68 Hz, 1H) 9.17 (d, J=2.44 Hz, 1H) 9.56 (d, J=2.20 Hz, 1H) 13.0 (bs, 1H).

Example 144

(5E+5Z)-[(5-amino-1H-pyrrolo[2,3-b]pyridin-3-yl)methylene]-2-(benzylamino)-3,5-dihydro-4H-imidazol one A solution of 2-(benzylamino)-5-[(5-nitro-1H-pyrrolo[2,3-b]pyridin-3-yl)methylene]-3,5-dihydro-4H-imidazol-4-one (1.1 g, 3 mmol) in ethyl acetate (250 mL) was hydrogenated in the presence of 5% Pd—C (0.5 g) at 40 psi and room temperature for several hours. After filtration, the crude material was purified by flash chromatography, eluting with dichloromethane/MeOH 3:1. Obtained the title product as a solid (0.3 g, 0.91 mmol, 30%).

$^1$H-NMR (DMSOd$_6$), δ ppm: 4.7 (s, 2H) 7.3-8.4 (m, 13H) 9.0 (s, 1H).

Example 145

(5Z)-2-(benzylamino)-5-[1-(1H-pyrrolo[2,3-b]pyridin-3-yl)ethylidene]-3,5-dihydro-4H-imidazol-4-one hydrochloride To a suspension of AlCl$_3$ (5.6 g, 42 mmol) in dry dichloromethane (200 mL), solid 1H-pyrrolo[2,3-b]pyridine (1 g, 8.4 mmol) was added and the reaction mixture was stirred at RT for 1 h. Acetyl chloride (3 mL, 42 mmol) was cautiously dropped in and the reaction mixture was stirred overnight at RT. After cooling in ice bath the mixture was cautiously quenched with methanol (40 mL), concentrated to dryness and purified by flash chromatography on silica gel (eluant: dichloromethane/methanol 10:1). Obtained 1.05 g (6.5 mmol, 78% yield) of desired 3-acetyl, 7-azaindole.

To a solution of 3-acetyl, 7-azaindole (320 mg, 2 mmol), thiohydantoin (465 mg, 3 mmol) and BF$_3$.Et$_2$O (1.52 mL, 12 mmol) in dry THF (14 mL), under argon, triethylamine (0.84 mL, 6 mmol) was added dropwise and the reaction mixture stirred for 5 days at RT.

The mixture was poured in ice and pH made slightly basic by addition of sodium bicarbonate. The solution was extracted with ethyl acetate, dried over sodium sulfate and concentrated to give an oil that crystallized from ethyl acetate (260 mg, 1 mmol, 50% yield).

The obtained imidazolone was dissolved in MeOH (5 mL) containing sodium hydroxide solution (12.6%, 0.4 mL) and methyl iodide (0.4 mL) was added to it under argon. After stirring at RT for 3 h part of the solvent was removed, water was added and the precipitate was filtered and washed with water. The desired methylthioimidazolone (220 mg, 0.8 mmol, 80% yield) was used directly in the next step. The crude product (200 mg, 0.73 mmol) was suspended in ethanol (5 mL) and benzylamine (2 mL) in a sealed tube and heated to 110° C. overnight. The solvent was evaporated off, ethyl ether was added and the precipitate was filtered and washed with ether.

The crude material was dissolved in methanol, a slight excess of 4N HCl in dioxane was added and the solution was stirred 30'. Ethyl ether was added and the precipitate was filtered, washed with ether and dried. Obtained a yellow solid (160 mg, 0.48 mmol, 66%).

$^1$H-NMR (DMSOd$_6$), δ ppm: 2.68 (s, 3H) 4.60 (s, 2H) 7.28-7.49 (m, 6H) 7.89-8.40 (m, 3H).

Example 146

The following compounds are prepared using the techniques described herein:
(5Z)-2-(4-chlorophenyl)-5-(1H-pyrrolo[2,3-b]pyridin-3-yl-methylene)-3,5-dihydro-4H-imidazol-4-one;
(5Z)-2-[3-(hydroxymethyl)phenyl]-5-(1H-pyrrolo[2,3-b]pyridin-3-ylmethylene)-3,5-dihydro-4H-imidazol-4-one;
(5Z)-2-pyridin-4-yl-5-(1H-pyrrolo[2,3-b]pyridin-3-ylmethylene)-3,5-dihydro-4H-imidazol-4-one;
(5Z)-2-pyridin-2-yl-5-(1H-pyrrolo[2,3-b]pyridin-3-ylmethylene)-3,5-dihydro-4H-imidazol-4-one;
(5Z)-2-{3-[(1-methylpiperidin-4-yl)oxy]phenyl}-5-(1H-pyrrolo[2,3-b]pyridin-3-ylmethylene)-3,5-dihydro-4H-imidazol-4-one;
(5Z)-2-(4-morpholin-4-ylphenyl)-5-(1H-pyrrolo[2,3-b]pyridin-3-ylmethylene)-3,5-dihydro-4H-imidazol-4-one;
(5Z)-2-(3-morpholin-4-ylphenyl)-5-(1H-pyrrolo[2,3-b]pyridin-3-ylmethylene)-3,5-dihydro-4H-imidazol-4-one;
(5Z)-2-(propylamino)-5-(1H-pyrrolo[2,3-b]pyridin-3-ylmethylene)-3,5-dihydro-4H-imidazol-4-one;
(5Z)-2-[(2-pyrrolidin-1-ylethyl)amino]-5-(1H-pyrrolo[2,3-b]pyridin-3-ylmethylene)-3,5-dihydro-4H-imidazol-4-one;
(5Z)-2-{[2-(dimethylamino)ethyl]amino}-5-(1H-pyrrolo[2,3-b]pyridin-3-ylmethylene)-3,5-dihydro-4H-imidazol-4-one;
(5Z)-2-[4-(hydroxymethyl)piperidin-1-yl]-5-(1H-pyrrolo[2,3-b]pyridin-3-ylmethylene)-3,5-dihydro-4H-imidazol-4-one;
(5Z)-1-[5-oxo-4-(1H-pyrrolo[2,3-b]pyridin-3-ylmethylene)-4,5-dihydro-1H-imidazol-2-yl]piperidine-4-carboxamide;
(5Z)-N,N-diethyl-1-[5-oxo-4-(1H-pyrrolo[2,3-b]pyridin-3-ylmethylene)-4,5-dihydro-1H-imidazol-2-yl]piperidine-3-carboxamide;
(5Z)-2-(4-hydroxypiperidin-1-yl)-5-(1H-pyrrolo[2,3-b]pyridin-3-ylmethylene)-3,5-dihydro-4H-imidazol-4-one;
(5Z)-2-(3-hydroxypiperidin-1-yl)-5-(1H-pyrrolo[2,3-b]pyridin-3-ylmethylene)-3,5-dihydro-4H-imidazol-4-one;
(5Z)-2-azetidin-1-yl-5-(1H-pyrrolo[2,3-b]pyridin-3-ylmethylene)-3,5-dihydro-4H-imidazol-4-one;
(5Z)-2-(2,5-dihydro-1H-pyrrol-1-yl)-5-(1H-pyrrolo[2,3-b]pyridin-3-ylmethylene)-3,5-dihydro-4H-imidazol-4-one;
(5Z)-2-(3-hydroxypyrrolidin-1-yl)-5-(1H-pyrrolo[2,3-b]pyridin-3-ylmethylene)-3,5-dihydro-4H-imidazol-4-one;
(5Z)-2-pyrazolidin-1-yl-5-(1H-pyrrolo[2,3-b]pyridin-3-ylmethylene)-3,5-dihydro-4H-imidazol-4-one;
(5Z)-1-[5-oxo-4-(1H-pyrrolo[2,3-b]pyridin-3-ylmethylene)-4,5-dihydro-1H-imidazol-2-yl]prolinamide;
(5Z)-2-(4-allylpiperazin-1-yl)-5-(1H-pyrrolo[2,3-b]pyridin-3-ylmethylene)-3,5-dihydro-4H-imidazol-4-one;
(5Z)-2-(4-ethylpiperazin-1-yl)-5-(1H-pyrrolo[2,3-b]pyridin-3-ylmethylene)-3,5-dihydro-4H-imidazol-4-one;
(5Z)-2-[4-(2-oxo-2-pyrrolidin-1-ylethyl)piperazin-1-yl]-5-(1H-pyrrolo[2,3-b]pyridin-3-ylmethylene)-3,5-dihydro-4H-imidazol-4-one;
(5Z)-N-isopropyl-2-{4-[5-oxo-4-(1H-pyrrolo[2,3-b]pyridin-3-ylmethylene)-4,5-dihydro-1H-imidazol-2-yl]piperazin-1-yl}acetamide;
(5Z)-2-[4-(4-hydroxyphenyl)piperazin-1-yl]-5-(1H-pyrrolo[2,3-b]pyridin-3-ylmethylene)-3,5-dihydro-4H-imidazol-4-one;
(5Z)-5-(1H-pyrrolo[2,3-b]pyridin-3-ylmethylene)-2-[4-(tetrahydrofuran-2-ylcarbonyl)piperazin-1-yl]-3,5-dihydro-4H-imidazol-4-one;
(5Z)-5-(1H-pyrrolo[2,3-b]pyridin-3-ylmethylene)-2-[(1S,2R,4S)-1,3,3-trimethylbicyclo[2.2.1]hept-2-yl]amino}-3,5-dihydro-4H-imidazol-4-one;
(5Z)-5-(1H-pyrrolo[2,3-b]pyridin-3-ylmethylene)-2-{[(1S,2R,4R)-1,7,7-trimethylbicyclo[2.2.1]hept-2-yl]amino}-3,5-dihydro-4H-imidazol-4-one;
(5Z)-2-[(1-phenylcyclopropyl)amino]-5-(1H-pyrrolo[2,3-b]pyridin-3-ylmethylene)-3,5-dihydro-4H-imidazol-4-one;
(5Z)-2-[(2-morpholin-4-ylethyl)amino]-5-(1H-pyrrolo[2,3-b]pyridin-3-ylmethylene)-3,5-dihydro-4H-imidazol-4-one;
(5Z)-2-[(2-pyrrolidin-1-ylethyl)amino]-5-(1H-pyrrolo[2,3-b]pyridin-3-ylmethylene)-3,5-dihydro-4H-imidazol-4-one;
(5Z)-1-methyl-N-{3-[(5-oxo-2-phenyl-1,5-dihydro-4H-imidazol-4-ylidene)methyl]-1H-pyrrolo[2,3-b]pyridin-5-yl}piperidine-4-carboxamide;
(5Z)-N$_3$-,N$_3$-dimethyl-N$_1$-{3-[(5-oxo-2-phenyl-1,5-dihydro-4H-imidazol-4-ylidene)methyl]-1H-pyrrolo[2,3-b]pyridin-5-yl}-beta-alaninamide;
(5Z)-3-(4-methylpiperazin-1-yl)-N-{3-[(5-oxo-2-phenyl-1,5-dihydro-4H-imidazol-4-ylidene)methyl]-1H-pyrrolo[2,3-b]pyridin-5-yl}benzamide;
(5Z)4-(4-methylpiperazin-1-yl)-N-{3-[(5-oxo-2-phenyl-1,5-dihydro-4H-imidazol-4-ylidene)methyl]-1H-pyrrolo[2,3-b]pyridin-5-yl}benzamide;
(5Z)-N-(3-{[2-(benzylamino)-5-oxo-1,5-dihydro-4H-imidazol-4-ylidene]methyl}-1H-pyrrolo[2,3-b]pyridin-5-yl)-1-methylpiperidine-4-carboxamide;
(5Z)-1-methyl-N-[3-({5-oxo-2-[(1-phenylethyl)amino]-1,5-dihydro-4H-imidazol-4-ylidene}methyl)-1H-pyrrolo[2,3-b]pyridin-5-yl]piperidine-4-carboxamide;
(5Z)-N-(3-{[2-(cyclohexylamino)-5-oxo-1,5-dihydro-4H-imidazol-4-ylidene]methyl}-1H-pyrrolo[2,3-b]pyridin-5-yl)-1-methylpiperidine-4-carboxamide;
(5Z)-N-(3-{[2-(bicyclo[2.2.1]hept-2-ylamino)-5-oxo-1,5-dihydro-4H-imidazol-4-ylidene]methyl}-1H-pyrrolo[2,3-b]pyridin-5-yl)-1-methylpiperidine-4-carboxamide
(5Z)-N-(3-{[2-(1-adamantylamino)-5-oxo-1,5-dihydro-4H-imidazol-4-ylidene]methyl}-1H-pyrrolo[2,3-b]pyridin-5-yl)-1-methylpiperidine-4-carboxamide;
(5Z)-1-methyl-N-[3-({5-oxo-2-[(1,7,7-trimethylbicyclo[2.2.1]hept-2-yl)amino]-1,5-dihydro-4H-imidazol-4-ylidene}methyl)-1H-pyrrolo[2,3-b]pyridin-5-yl]piperidine-4-carboxamide;

(5Z)-N-(3-{[2-(1-azabicyclo[2.2.2]oct-3-ylamino)-5-oxo-1,5-dihydro-4H-imidazol-4-ylidene]methyl}-1H-pyrrolo[2,3-b]pyridin-5-yl)-1-methylpiperidine-4-carboxamide;

(5Z)-1-methyl-N-[3-({5-oxo-2-[(1-phenyl-2-pyrrolidin-1-ylethyl)amino]-1,5-dihydro-4H-imidazol-4-ylidene}methyl)-1H-pyrrolo[2,3-b]pyridin-5-yl]piperidine-4-carboxamide;

(5Z)-$N_1$-(3-{[2-benzylamino)-5-oxo-1,5-dihydro-4H-imidazol-4-ylidene]methyl}-1H-pyrrolo[2,3-b]pyridin-5-yl)-$N_3$,$N_3$-dimethyl-beta-alaninamide;

(5Z)-$N_3$,$N_3$-dimethyl-$N_1$-[3-({5-oxo-2-[(1-phenylethyl)amino]-1,5-dihydro-4H-imidazol-4-ylidene 3 methyl)-1H-pyrrolo[2,3-b]pyridin-5-yl]-beta-alaninamide;

(5Z)-$N_1$-(3-{[2-(cyclohexylamino)-5-oxo-1,5-dihydro-4H-imidazol-4-ylidene]methyl3-1H-pyrrolo[2,3-b]pyridin-5-yl)-$N_3$, $N_3$-dimethyl-beta-alaninamide;

(5Z)-$N_1$-(3-{[2-(bicyclo[2.2.1]hept-2-ylamino)-5-oxo-1,5-dihydro-4H-imidazol-4-ylidene]methyl}-1H-pyrrolo[2,3-b]pyridin-5-yl)-$N_3$, $N_3$-dimethyl-beta-alaninamide;

(5Z)-N-(3-{[2-(1-azabicyclo[2.2.2]oct-3-ylamino)-5-oxo-1,5-dihydro-4H-imidazol-4-ylidene]methyl}-1H-pyrrolo[2,3-b]pyridin-5-yl)butanamide;

(5Z)-N-(3-{[2-(benzylamino)-5-oxo-1,5-dihydro-4H-imidazol-4-ylidene]methyl}-1H-pyrrolo[2,3-b]pyridin-5-yl)-3-(4-methylpiperazin-1-yl)benzamide;

(5Z)-3-(4-methylpiperazin-1-yl)-N-[3-({5-oxo-2-[(1-phenylethyl)amino]-1,5-dihydro-4H-imidazol-4-ylidene}methyl)-1H-pyrrolo[2,3-b]pyridin-5-yl]benzamide;

(5Z)-N-(3-{[2-(cyclohexylamino)-5-oxo-1,5-dihydro-4H-imidazol-4-ylidene]methyl}-1H-pyrrolo[2,3-b]pyridin-5-yl)-3-(4-methylpiperazin-1-yl)benzamide;

(5Z)-N-(3-{[2-(bicyclo[2.2.1]hept-2-ylamino)-5-oxo-1,5-dihydro-4H-imidazol-4-ylidene]methyl}-1H-pyrrolo[2,3-b]pyridin-5-yl)-3-(4-methylpiperazin-1-yl)benzamide;

(5Z)-N-(3-{[2-(1-azabicyclo[2.2.2]oct-3-ylamino)-5-oxo-1,5-dihydro-4H-imidazol-4-ylidene]methyl}-1H-pyrrolo[2,3-b]pyridin-5-yl)-2-methylpropanamide;

(5Z)-N-(3-{[2-(benzylamino)-5-oxo-1,5-dihydro-4H-imidazol-4-ylidene]methyl}-1H-pyrrolo[2,3-b]pyridin-5-yl)-4-(4-methylpiperazin-1-yl)benzamide;

(5Z)-4-(4-methylpiperazin-1-yl)-N-[3-({5-oxo-2-[(1-phenylethyl)amino]-1,5-dihydro-4H-imidazol-4-ylidene}methyl)-1H-pyrrolo[2,3-b]pyridin-5-yl]benzamide;

(5Z)-N-(3-{[2-(cyclohexylamino)-5-oxo-1,5-dihydro-4H-imidazol-4-ylidene]methyl}-1H-pyrrolo[2,3-b]pyridin-5-yl)-4-(4-methylpiperazin-1-yl)benzamide;

(5Z)-N-(3-{[2-(bicyclo[2.2.1]hept-2-ylamino)-5-oxo-1,5-dihydro-4H-imidazol-4-ylidene]methyl}-1H-pyrrolo[2,3-b]pyridin-5-yl)-4-(4-methylpiperazin-1-yl)benzamide;

(5Z)-N-(3-{[2-(1-azabicyclo[2.2.2]oct-3-ylamino)-5-oxo-1,5-dihydro-4-4H-imidazol-4-ylidene]methyl}-1H-pyrrolo[2,3-b]pyridin-5-yl)-3-methylbutanamide;

Example 147

(5Z)-2-[3-(4-methylpiperazin-1-yl)phenyl]-5-(1H-pyrrolo[2,3-b]pyridin-3-ylmethylene)-3,5-dihydro-4H-imidazol-4-one N-[3-(4-methylpiperazin-1-yl)benzoyl]glycine (a) N-[3-(4-methylpiperazin-1-yl)benzoyl]glycine A solution of 3-F-benzonitrile (8.2 g, 68 mmol) and N-methylpiperazine (41.5 mL, 374 mmol) in anhydrous DMSO (60 mL) was warmed at 100° C. with stirring for 28 h. After cooling the reaction mixture was poured into water (600 mL) and was extracted with diethylether (3×500 mL). The organic phase was washed with brine, dried over sodium sulfate and concentrated to give 3-(4-methylpiperazin-1-yl)benzonitrile as an oil (10.3 g, 51.2 mmol, 75%). The crude compound was treated with 37% HCl (50 mL) at reflux for 50 min., concentrated to dryness, by stripping three times with toluene. The crude product was crystallized from methanol/diethylether. Obtained 3-(4-methylpiperazin-1-yl)benzoic acid dihydrochloride(10.2 g, 34.7 mmol, 51% yield).

To the acid (0.58 g, 2 mmol), suspended in dry dichloromethane (50 mL) with two drops of DMF, oxalylchloride (0.9 mL, 10 mmol) was added dropwise and the mixture was refluxed for 2 h. The reaction mixture was thoroughly concentrated and the residue was dissolved in dry THF (7 mL), t-butylglycinate (0.28 g, 2.1 mmol) and dry TEA (3 mmol) were added and the mixture was stirred overnight at room temperature. After concentration crude tert-butyl N-[3-(4-methylpiperazin-1-yl)benzoyl]glycinate was obtained (0.6 g, 1.8 mmol, 90%). A solution of the glycinate (0.1 g, 0.3 mmol) in dichloromethane (4 mL) and trifluoroacetic acid (3 mL) was stirred at room temperature for a few hours. After multiple strippings with toluene, the desired N-[3-(4-methylpiperazin-1-yl)benzoyl]glycine ditrifluoroacetate was isolated in 78% yield.

$^1$H-NMR (DMSOd$_6$), δ ppm: 2.2 (s, 3H) 2.5 (m, 4H) 3.2 (m, 4H) 4.1 (s, 2H) 6.8-7.5 (m, 4H).

(b) (5Z)-2-[3-(4-methylpiperazin-1-yl)phenyl]-5-(1H-pyrrolo[2,3-b]pyridin-3-ylmethylene)-3,5-dihydro-4H-imidazol-4-one N-[3-(4-methylpiperazin-1-yl)benzoyl]glycine The acid is then reacted as described in Example 1 to afford the title compound.

The dihydrochloride is obtained by suspending the product thus formed in methanol. Excess 4M HCl in dioxane is added, and the mixture is stirred at room temperature for 30 minutes. The precipitate formed is filtered, and united first with methanol and then with diethyl ether to yield the dihydrochloride.

The above preferred embodiments and examples were given to illustrate the scope and spirit of the present invention. Theses embodiments and examples will make apparent to those skilled in the art other embodiments and examples. These other embodiments and examples are within the contemplation of the present invention. Therefore, the present invention should be limited only by the appended claims.

What is claimed is:

1. A compound of the formula:

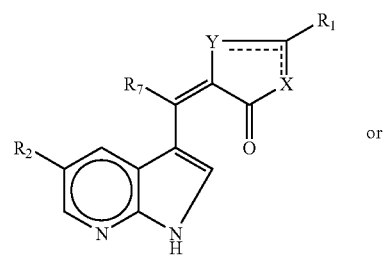

or

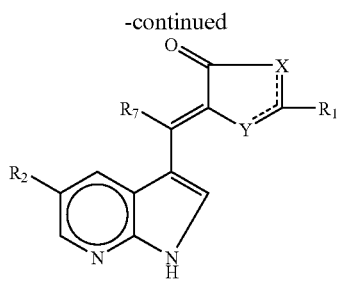

or pharmaceutically acceptable salts thereof,
wherein
$R_1$ is optionally substituted aryl, optionally substituted heteroaryl, $SR_5$, or $NR_3R_4$;
$R_3$ and $R_4$ are independently hydrogen, optionally substituted $C_1$-$C_8$ alkyl, optionally substituted $C_1$-$C_8$ hydroxyalkyl, optionally substituted $C_1$-$C_8$ alkoxy $C_1$-$C_8$ alkyl, optionally substituted $C_1$-$C_8$ alkylamino $C_1$-$C_8$ alkyl, optionally substituted $C_1$-$C_8$ dialkylamino $C_1$-$C_8$ alkyl, optionally substituted saturated or unsaturated $C_3$-$C_{12}$ cycloalkyl, optionally substituted saturated or unsaturated $C_3$-$C_{12}$ cycloalkyl $C_1$-$C_8$ alkyl, optionally substituted $C_2$-$C_8$ alkenyl group, optionally substituted aryl, optionally substituted aryl $C_1$-$C_8$ alkyl, optionally substituted heterocyclyl, or optionally substituted heterocyclyl $C_1$-$C_8$ alkyl; or
$R_3$ and $R_4$ taken together with the nitrogen atom to which they are attached to form a heterocyclic ring containing 1 ring nitrogen atom and up to 1 or 2 additional ring heteroatoms selected from oxygen, nitrogen and sulfur;
$R_5$ is optionally substituted $C_1$-$C_8$ alkyl, optionally substituted saturated or unsaturated $C_3$-$C_{12}$ cycloalkyl, optionally substituted saturated or unsaturated $C_3$-$C_{12}$ cycloalkyl $C_1$-$C_{18}$ alkyl, optionally substituted aryl, optionally substituted aryl $C_1$-$C_8$ alkyl, optionally substituted heterocyclyl, optionally substituted heterocyclyl $C_1$-$C_8$ alkyl, optionally substituted aryloxy $C_1$-$C_8$ alkyl, or optionally substituted $C_1$-$C_8$ alkyloxy $C_1$-$C_8$ alkyl;
$R_2$ is hydrogen, nitro, amino or —NH-Z-$R_6$;
Z is CO, $SO_2$, or $CH_2$;
$R_6$ is optionally substituted $C_1$-$C_8$ alkyl, optionally substituted aryl, optionally substituted aryl $C_1$-$C_8$ alkyl, optionally substituted heterocyclyl, optionally substituted heterocyclyl $C_1$-$C_8$ alkyl, optionally substituted $C_1$-$C_8$ hydroxyalkyl, optionally substituted $C_1$-$C_8$ alkoxy $C_1$-$C_8$ alkyl, optionally substituted $C_1$-$C_8$ dialkylamino $C_1$-$C_8$ alkyl, optionally substituted $C_1$-$C_8$ alkyl amino $C_1$-$C_8$ alkyl, optionally substituted $C_1$-$C_8$ alkylamino, optionally substituted $C_1$-$C_8$ dialkylamino, amino group, optionally substituted $C_1$-$C_8$ alkyloxy, optionally substituted aryl $C_1$-$C_8$ alkyloxy, optionally substituted arylamino, optionally substituted aryloxy, or optionally substituted aryl $C_1$-$C_8$ alkylamino;
$R_7$ is hydrogen or optionally substituted $C_1$-$C_8$ alkyl;
X is N;
Y is N; and the dotted lines between the carbon atom with the $R_1$ substituent and X and Y represents a single or double bond, provided that the carbon atom having the $R_1$ substituent does not have a double bond between X and Y simultaneously, wherein the alkyl, aryl, cycloalkyl, heteroaryl or heterocyclic group, when used alone or in combination, are each independently optionally substituted with halogen, amino, mercapto, thio $C_1$-$C_8$ alkyl, $C_1$-$C_8$ alkyl amino, di $C_1$-$C_8$ alkyl amino, $C_1$-$C_8$ alkyl carbonylamino, $C_1$-$C_8$ alkoxy, $C_1$-$C_8$ hydroxy $C_1$-$C_8$ alkyl, halo $C_1$-$C_8$ alkyl, hydoxy $C_1$-$C_8$ alkyl, hydroxy, $C_1$-$C_8$ alkoxy, $C_1$-$C_8$ alkoxy $C_1$-$C_8$ alkyl, aryl, aryl $C_1$-$C_8$ alkyl, aryloxy, aryl $C_1$-$C_8$ alkoxy, heterocyclic $C_1$-$C_8$ alkyl, carbamoyl, $C_3$-$C_{12}$ saturated or unsaturated cycloalkyl, $C_3$-$C_{12}$ satruated or unsaturated cycloalkyl $C_1$-$C_8$ alkyl, $C_3$-$C_{12}$ saturated or unsaturated cycloalkoxy, $C_1$-$C_8$ alkyl amino carbonyl $C_1$-$C_8$ alkyl, di $C_1$-$C_8$ alkyl amino carbonyl $C_1$-$C_8$ alkyl, heterocyclic carbonyl, aryl carbonyl, $C_1$-$C_8$ alkyl amino carbonyl, di $C_1$-$C_8$ alkyl amino carbonyl, $C_1$-$C_8$ alkyl carbonyl or $C_2$-$C_8$ alkenyl.

2. The compound according to claim 1 wherein $R_1$ is optionally substituted aryl, optionally substituted heteroaryl or —$NR_3R_4$.

3. The compound according to claim 2, wherein $R_3$ and $R_4$ are independently hydrogen, optionally substituted saturated or unsaturated $C_3$-$C_{12}$ cycloalkyl, optionally substituted saturated or unsaturated $C_3$-$C_{12}$ cycloalkyl $C_1$-$C_8$ alkyl, optionally substituted aryl, optionally substituted aryl $C_1$-$C_8$ alkyl, optionally substituted heteroaryl, optionally substituted $C_1$-$C_8$ alkyl or $C_1$-$C_8$ alkyl or $R_3$ and $R_4$ taken together with the nitrogen atom to which they are attached from an optionally substituted nitrogen containing heterocyclic ring.

4. The compound according to any one of claim 1 or 2 when $R_2$ is hydrogen.

5. The compound according to claim 1 or 2 wherein $R_7$ is hydrogen.

6. The compound according to claim 1 wherein X is NH or N and Y is N or NH.

7. The compound according to claim 5 when $R_2$ and $R_7$ are hydrogen, X is NH or N, and Y is N or NH.

8. The compound according to claim 1 wherein $R_1$ is aryl or heteroaryl or $NR_3R_4$, $R_4$ is hydrogen and $R_3$ is optionally substituted saturated or unsaturated $C_3$-$C_{12}$ cycloalkyl, optionally substituted saturated or unsaturated $C_3$-$C_{12}$ cycloalkyl $C_1$-$C_8$ alkyl, optionally substituted aryl, optionally substituted aryl $C_1$-$C_8$ alkyl, optionally substituted heterocyclic or optionally substituted heterocyclic $C_1$-$C_8$ alkyl.

9. The compound according to claim 1 wherein $R_2$ is hydrogen or NHZ $R_6$, Z is CO and $R_6$ is optionally substituted $C_1$-$C_8$ alkyl, optionally substituted aryl, optionally substituted heterocyclic, or optionally substituted di ($C_1$-$C_8$) alkyl amino $C_1$-$C_8$ alkyl.

10. The compound according to claim 2 wherein $R_2$ is hydrogen or NHZ $R_6$, Z is CO, $R_6$ is optionally substituted $C_1$-$C_8$ alkyl, optionally substituted aryl, optionally substituted heterocyclic, optionally substituted heterocyclic $C_1$-$C_8$ loweralkyl, optionally substituted di ($C_1$-$C_8$) alkyl amino $C_1$-$C_8$ alkyl, $R_7$ is H, X is NH or N, and Y is N or S or NH or NMe.

11. The compound according to claim 1 wherein Z is CO or $SO_2$, and $R_6$ is amino, optionally substituted $C_1$-$C_8$ alkyl amino, optionally substituted $C_1$-$C_8$ di alkyl amino, optionally substituted $C_1$-$C_8$ alkoxy, optionally substituted aryloxy, optionally substituted aryl $C_1$-$C_8$ alkoxy, optionally substituted aryl amino or optionally substituted aryl $C_1$-$C_8$ alkyl amino.

12. The compound according to claim 1 having the formula

13. The compound according to claim 1 having the formula

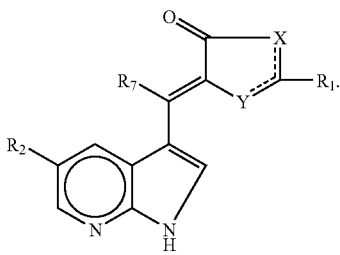

14. The compound according to claim 1 having the formula

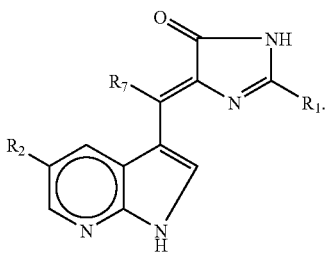

wherein $R_2$ is H and $R_1$ is optionally substituted heteroaryl or optionally substituted aryl.

15. The compound according to claim 1 wherein $R_2$ is H, and $R_1$ is $NHR_3$, wherein $R_3$ is arylalkyl, alkyl, cycloalkyl, heterocyclic, or heterocyclic alkyl which $R_3$ is unsubstituted or substituted with halo, hydroxyl $C_1$-$C_8$ alkyl, heterocyclic, $C_1$-$C_8$ alkoxy or aryl or cycloalkyl.

16. The compound according to claim 15 wherein $R_3$ is benzyl, $C_1$-$C_6$ alkyl, or furylmethyl, cyclohexyl, bicyclo[2.2.2] heptyl or azabicyclo[2.2.2] octyl which $R_3$ is unsubstituted or substituted with $C_1$-$C_6$ alkyl, thienyl, piperidenyl, or hydroxyl or 2-OH ethyl, or pyrrolidinyl, methyl.

17. The compound according to claim 1 wherein $R_2$ is H and $R_1$ is $NR_3R_4$ wherein $R_3$ and $R_4$ taken together with the nitrogen atom to which they are attached form a 5- or 6-membered heterocyclic ring containing 1 nitrogen and optionally one or two additional ring heteroatoms selected from oxygen, nitrogen or sulfur and the remaining ring atoms are carbon atoms, which is unsubstituted or substituted with $C_1$-$C_6$ alkyl.

18. The compound according to claim 1 wherein $R_3$ and $R_4$ taken together form a pyridyl, morpholinyl, piperidinyl, or pyrrolidino, which is unsubstituted or substituted with $C_1$-$C_6$ alkyl.

19. The compound according to claim 1 where $R_2$ is H and $R_1$ is aryl, arylalkyl, heteroaryl, or heteroarylalkyl, which is unsubstituted or substituted with alkyl or hydroxylalkyl.

20. The compound according to claim 19 where $R_1$ is phenyl, benzyl, furylmethyl or which is unsubstituted or substituted with $C_1$-$C_6$ alkyl or hydroxyl $C_1$-$C_6$ alkyl.

21. The compound according to claim 1 wherein $R_1$ is NHAD, wherein A is $(CHR_{10})_m$—$(CH_2)_n$, n is O-5, m is O-5, is $C_1$-$C_8$ alkyl, aryl or aryl $C_1$-$C_8$ alkyl, and D is optionally substituted alkyl, optionally substituted cycloalkyl, optionally substituted aryl or optionally substituted heterocyclic wherein the optional substituents on alkyl, cycloalkyl, aryl, and heterocyclic are halogen, hydroxy, $C_1$-$C_8$ alkyl, amino, $C_1$-$C_8$ alkyl amino, di $C_1$-$C_8$ alkyl amino, $C_1$-$C_8$ alkoxy, halo $C_1$-$C_8$ alkyl, aryloxy, aryl $C_1$-$C_8$ alkoxy, cycloalkyl, heterocyclic, haloaryl, halocycloalkyl, haloheterocyclic, $C_1$-$C_8$ alkyl aryl, $C_1$-$C_8$ alkyl cycloalkyl, or aklylheterocyclic.

22. The compound according to claim 21 wherein n and m are both O.

23. The compound according to claim 21 wherein D is optionally substituted cycloalkyl wherein cycloalkyl is cyclohexyl, cycloheptyl, bicyclo[2.2.1] heptyl, adamantyl, 1,7,7-trimethylbicyclo[2.2.1]heptyl, indanyl, dihydroindenyl, tetrahydronaphthyl, or dihydronaphthyl; phenyl; optionally substituted heterocyclic, wherein heterocyclic is furyl, thienyl, piperidinyl, morphinyl, tetrahydrofuryl, azabicyclo[2.2.2.]octyl, azabicyclo[3.2.1.]octyl, benzothienyl or piperazinyl; or optionally substituted $C_1$-$C_8$ alkoxy.

24. The compound according to claim 1 wherein $R_1$ is optionally substituted aryl or optionally substituted heteroaryl, wherein aryl is phenyl and heteroaryl is furyl or pyridyl.

25. A composition comprising a compound according to claim 1 and a pharmaceutical carrier therefor.

26. The compound according to claim 1 which is
(5E)-2-phenyl-5-(1H-pyrrolo[2,3-b]pyridin-3-ylmethylene)-3,5-dihydro-4H-imidazol-4-one;
(5Z)-2-phenyl-5-(1H-pyrrolo[2,3-b]pyridin-3-ylmethylene)-3,5-dihydro-4H-imidazol-4-one;
(5Z)-2-(3-methylphenyl)-5-(1H-pyrrolo[2,3-b]pyridin-3-ylmethylene)-3,5-dihydro-4H-imidazol-4-one;
(5Z)-2-(4-methylphenyl)-5-(1H-pyrrolo[2,3-b]pyridin-3-ylmethylene)-3,5-dihydro-4H-imidazol-4-one;
(5Z)-2-(4-bromophenyl)-5-(1H-pyrrolo[2,3-b]pyridin-3-ylmethylene)-3,5-dihydro-4H-imidazol-4-one;
(5Z)-2-(4-fluorophenyl)-5-(1H-pyrrolo[2,3-b]pyridin-3-ylmethylene)-3,5-dihydro-4H-imidazol-4-one hydrochloride;
(5E)-2-(4-acetylaminophenyl)5-(1H-pyrrolo[2,3-b]pyridin-3-ylmethylene-(2-benzylamino)-3,5-dihydro-4-H-imidazol-4-one;
(5Z)-2-(4-acetylaminophenyl)5-(1H-pyrrolo[2,3-b]pyridin-3-ylmethylene-(2-benzylamino)-3,5-dihydro-4-H-imidazol-4-one;
(5Z)-2-[4-(hydroxymethyl)phenyl]-5-(1H-pyrrolo[2,3-b]pyridin-3-ylmethylene)-3,5-dihydro-4H-imidazol-4-one;
(5Z)-2-pyridin-3-yl-5-(1H-pyrrolo[2,3-b]pyridin-3-ylmethylene)-3,5-dihydro-4H-imidazol-4-one;
(5Z)-2-(2-furyl)-5-(1H-pyrrolo[2,3-b]pyridin-3-ylmethylene)-3,5-dihydro-4H-imidazol-4-one;
(5Z)-2-[3-(4-methylpiperazin-1-yl)phenyl]-5-(1H-pyrrolo[2,3-b]pyridin-3-ylmethylene)-3,5-dihydro-4H-imidazol-4-one;
(5E)-2-[4-(4-methylpiperazin-1-yl)phenyl]-5-(1H-pyrrolo[2,3-b]pyridin-3-ylmethylene)-3,5-dihydro-4H-imidazol-4-one dihydrochloride;

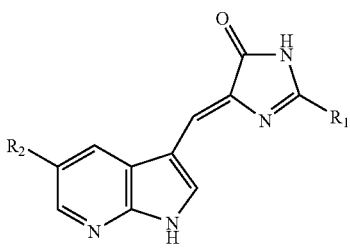

(5Z)-2-[4-(4-methylpiperazin-1-yl)phenyl]-5-(1H-pyrrolo[2,3-b]pyridin-3-ylmethylene)-3,5-dihydro-4H-imidazol-4-one dihydrochloride;

(5Z)-2-{4-[(1-methylpiperidin-4-yl)oxy]phenyl}-5-(1H-pyrrolo[2,3-b]pyridin-3-ylmethylene)-3,5-dihydro-4H-imidazol-4-one dihydrochloride;

(5Z)-2-morpholin-4-yl-5-(1H-pyrrolo[2,3-b]pyridin-3-ylmethylene)-3,5-dihydro-4H-imidazol-4-one dihydrochloride;

(5Z)-2-(4-methylpiperazin-1-yl)-5-(1H-pyrrolo[2,3-b]pyridin-3-ylmethylene)-3,5-dihydro-4H-imidazol-4-one dihydrochloride;

(5Z)-2-(4-phenylpiperazin-1-yl)-5-(1H-pyrrolo[2,3-b]pyridin-3-ylmethylene)-3,5-dihydro-4H-imidazol-4-one trihydrochloride;

(5Z)-2-piperidin-1-yl-5-(1H-pyrrolo[2,3-b]pyridin-3-ylmethylene)-3,5-dihydro-4H-imidazol-4-one dihydrochloride;

(5Z)-2-[3-(hydroxymethyl)piperidin-1-yl]-5-(1H-pyrrolo[2,3-b]pyridin-3-ylmethylene)-3,5-dihydro-4H-imidazol-4-one dihydrochloride;

(5Z)-2-pyrrolidin-1-yl-5-(1H-pyrrolo[2,3-b]pyridin-3-ylmethylene)-3,5-dihydro-4H-imidazol-4-one dihydrochloride;

(5Z)-2-(4-benzylpiperazin-1-yl)-5-(1H-pyrrolo[2,3-b]pyridin-3-ylmethylene)-3,5-dihydro-4H-imidazol-4-one trihydrochloride;

(5Z)-2-(4-isopropylpiperazin-1-yl)-5-(1H-pyrrolo[2,3-b]pyridin-3-ylmethylene)-3,5-dihydro-4H-imidazol-4-one dihydrochloride;

(5Z)-5-(1H-pyrrolo[2,3-b]pyridin-3-ylmethylene)-2-[4-(tetrahydrofuran-2-ylmethyl)piperazin-1-yl]-3,5-dihydro-4H-imidazol-4-one dihydrochloride;

(5Z)-2-[4-(2-hydroxyethyl)piperazin-1-yl]-5-(1H-pyrrolo[2,3-b]pyridin-3-ylmethylene)-3,5-dihydro-4H-imidazol-4-one dihydrochloride;

(5Z)-2-(4-phenylpiperidin-1-yl)-5-(1H-pyrrolo[2,3-b]pyridin-3-ylmethylene)-3,5-dihydro-4H-imidazol-4-one ditrifluoroacetate;

(5Z)-2-(1,4'-bipiperidin-1'-yl)-5-(1H-pyrrolo[2,3-b]pyridin-3-ylmethylene)-3,5-dihydro-4H-imidazol-4-one trihydrochloride;

(5Z)-2-azepan-1-yl-5-(1H-pyrrolo[2,3-b]pyridin-3-ylmethylene)-3,5-dihydro-4H-imidazol-4-one dihydrochloride;

(5Z)-1-[5-oxo-4-(1H-pyrrolo[2,3-b]pyridin-3-ylmethylene)-4,5-dihydro-1H-imidazol-2-yl]piperidine-3-carboxamide ditrifluoroacetate;

(5Z)-2-(piperazin-1-yl)-5-(1H-pyrrolo[2,3-b]pyridin-3-ylmethylene)-3,5-dihydro-4H-imidazol-4-one tritrifluoroacetate;

(5Z)-2-[4-(2-furoyl)piperazin-1-yl]-5-(1H-pyrrolo[2,3-b]pyridin-3-ylmethylene)-3,5-dihydro-4H-imidazol-4-one dihydrochloride;

(5Z)-2-(1,3-dihydro-2H-isoindol-2-yl)-5-(1H-pyrrolo[2,3-b]pyridin-3-ylmethylene)-3,5-dihydro-4H-imidazol-4-one dihydrochloride;

(5Z)-2-(2-methylmorpholin-4-yl)-5-(1H-pyrrolo[2,3-b]pyridin-3-ylmethylene)-3,5-dihydro-4H-imidazol-4-one dihydrochloride;

(5Z)-2-(4-propylpiperazin-1-yl)-5-(1H-pyrrolo[2,3-b]pyridin-3-ylmethylene)-3,5-dihydro-4H-imidazol-4-one dihydrochloride;

(5Z)-2-(4-methylpiperidin-1-yl)-5-(1H-pyrrolo[2,3-b]pyridin-3-ylmethylene)-3,5-dihydro-4H-imidazol-4-one dihydrochloride;

(5Z)-2-(2,6-dimethylmorpholin-4-yl)-5-(1H-pyrrolo[2,3-b]pyridin-3-ylmethylene)-3,5-dihydro-4H-imidazol-4-one dihydrochloride;

(5Z)-2-(3,5-dimethylpiperidin-1-yl)-5-(1H-pyrrolo[2,3-b]pyridin-3-ylmethylene)-3,5-dihydro-4H-imidazol-4-one ditrifluoroacetate;

(5Z)-2-[4-(cyclohexylmethyl)piperazin-1-yl]-5-(1H-pyrrolo[2,3-b]pyridin-3-ylmethylene)-3,5-dihydro-4H-imidazol-4-one trihydrochloride;

(5Z)-2-(4-benzylpiperidin-1-yl)-5-(1H-pyrrolo[2,3-b]pyridin-3-ylmethylene)-3,5-dihydro-4H-imidazol-4-one dihydrochloride;

(5Z)-2-(4-pyrrolidin-1-ylpiperidin-1-yl)-5-(1H-pyrrolo[2,3-b]pyridin-3-ylmethlene)-3,5-dihydro-4H-imidazol-4-one trihydrochloride;

(5Z)-2-(1,4-diazepan-1-yl)-5-(1H-pyrrolo[2,3-b]pyridin-3-ylmethylene)-3,5-dihydro-4H-imidazol-4-one trihydrochloride;

(5Z)-2-[4-(3,4-dichlorophenyl)piperazin-1-yl]-5-(1H-pyrrolo[2,3-b]pyridin-3-ylmethylene)-3,5-dihydro-4H-imidazol-4-one trihydrochloride;

(5Z)-(2-[4-(2-fluorophenyl)piperazin-1-yl]-5-(1H-pyrrolo[2,3-b]pyridin-3-ylmethylene)-3,5-dihydro-4H-imidazol-4-one trihydrochloride;

(5Z)-2-[4-(2-methoxyethyl)piperazin-1-yl]-5-(1H-pyrrolo[2,3-b]pyridin-3-ylmethylene)-3,5-dihydro-4H-imidazol-4-one trihydrochloride;

(5Z)-2-[4-(4-fluorophenyl)piperazin-1-yl]-5-(1H-pyrrolo[2,3-b]pyridin-3-ylmethylene)-3,5-dihydro-4H-imidazol-4-one trihydrochloride;

(5Z)-2-[(2R)-2-benzylmorpholin-4-yl]-5-(1H-pyrrolo[2,3-b]pyridin-3-ylmethylene)-3,5-dihydro-4H-imidazol-4-one hydrochloride trifluoroacetate;

(5Z)-2-(cyclohexylamino)-5-(1H-pyrrolo[2,3-b]pyridin-3-ylmethylene)-3,5-dihydro-4H-imidazol-4-one hydrochloride;

(5Z)-2-[(1-benzylpiperidin-4-yl)amino]-5-(1H-pyrrolo[2,3-b]pyridin-3-ylmethylene)-3,5-dihydro-4H-imidazol-4-one trihydrochloride;

(5Z)-2-(benzylamino)-5-(1H-pyrrolo[2,3-b]pyridin-3-ylmethylene)-3,5-dihydro-4H-imidazol-4-one hydrochloride;

(5Z)-2-[(2-hydroxyethyl)amino]-5-(1H-pyrrolo[2,3-b]pyridin-3-ylmethylene)-3,5-dihydro-4H-imidazol-4-one dihydrochloride;

(5Z)-2-[(3,3-dimethylbutyl)amino]-5-(1H-pyrrolo[2,3-b]pyridin-3-ylmethylene)-3,5-dihydro-4H-imidazol-4-one dihydrochloride;

(5Z)-2-[(2-furylmethyl)amino]-5-(1H-pyrrolo[2,3-b]pyridin-3-ylmethylene)-3,5-dihydro-4H-imidazol-4-one dihydrochloride;

(5Z)-2-(cyclopropylamino)-5-(1H-pyrrolo[2,3-b]pyridin-3-ylmethylene)-3,5-dihydro-4H-imidazol-4-one dihydrochloride;

(5Z)-5-(1H-pyrrolo[2,3-b]pyridin-3-ylmethylene)-2-[(thien-2-ylmethyl)amino]-3,5-dihydro-4H-imidazol-4-one dihydrochloride;

(5Z)-2-(propylamino)-5-(1H-pyrrolo[2,3-b]pyridin-3-ylmethylene)-3,5-dihydro-4H-imidazol-4-one dihydrochloride;

(5Z)-2-[(2-piperidin-1-ylethyl)amino]-5-(1H-pyrrolo[2,3-b]pyridin-3-ylmethylene)-3,5-dihydro-4H-imidazol-4-one dihydrochloride;

(5Z)-2-[(3-furylmethyl)amino]-5-(1H-pyrrolo[2,3-b]pyridin-3-ylmethylene)-3,5-dihydro-4H-imidazol-4-one dihydrochloride;

(5Z)-2-[(2-morpholin-1-ylethyl)amino]-5-(1H-pyrrolo[2,3-b]pyridin-3-ylmethylene)-3,5-dihydro-4H-imidazol-4-one dihydrochloride;

(5Z)-5-(1H-pyrrolo[2,3-b]pyridin-3-ylmethylene)-2-[(tetrahydrofuran-2-ylmethyl)amino]-3,5-dihydro-4H-imidazol-4-one hydrochloride;

(5Z)-2-(pentylamino)-5-(1H-pyrrolo[2,3-b]pyridin-3-ylmethylene)-3,5-dihydro-4H-imidazol-4-one dihydrochloride;

(5Z)-2-(heptylamino)-5-(1H-pyrrolo[2,3-b]pyridin-3-ylmethylene)-3,5-dihydro-4H-imidazol-4-one ditrifluoroacetate;

(5Z)-2-[(cyclohexylmethyl)amino]-5-(1H-pyrrolo[2,3-b]pyridin-3-ylmethylene)-3,5-dihydro-4H-imidazol-4-one dihydrochloride;

(5Z)-2-[(2-methylbutyl)amino]-5-(1H-pyrrolo[2,3-b]pyridin-3-ylmethylene)-3,5-dihydro-4H-imidazol-4-one dihydrochloride;

(5Z)-2-((cyclopropylmethyl)amino)-5-(1H-pyrrolo[2,3-b]pyridin-3-ylmethylene)-3,5-dihydro-4H-imidazol-4-one dihydrochloride;

(5Z)-2-[(3-isopropoxypropyl)amino]-5-(1H-pyrrolo[2,3-b]pyridin-3-ylmethylene)-3,5-dihydro-4H-imidazol-4-one dihydrochloride;

(5Z)-2-(ethylamino)-5-(1H-pyrrolo[2,3-b]pyridin-3-ylmethylene)-3,5-dihydro-4H-imidazol-4-one dihydrochloride;

(5Z)-2-[(2-phenylethyl)amino]-5-(1H-pyrrolo[2,3-b]pyridin-3-ylmethylene)-3,5-dihydro-4H-imidazol-4-one dihydrochloride;

(5Z)-2-[(4-fluorobenzyl)amino]-5-(1H-pyrrolo[2,3-b]pyridin-3-ylmethylene)-3,5-dihydro-4H-imidazol-4-one dihydrochloride;

(5Z)-2-[(3-fluorobenzyl)amino]-5-(1H-pyrrolo[2,3-b]pyridin-3-ylmethylene)-3,5-dihydro-4H-imidazol-4-one dihydrochloride;

(5Z)-2-[(2-fluorobenzyl)amino]-5-(1H-pyrrolo[2,3-b]pyridin-3-ylmethylene)-3,5-dihydro-4H-imidazol-4-one dihydrochloride;

(5Z)-2-[(3-chlorobenzyl)amino]-5-(1H-pyrrolo[2,3-b]pyridin-3-ylmethylene)-3,5-dihydro-4H-imidazol-4-one dihydrochloride;

(5Z)-2-[(4-chlorobenzyl)amino]-5-(1H-pyrrolo[2,3-b]pyridin-3-ylmethylene)-3,5-dihydro-4H-imidazol-4-one dihydrochloride;

(5Z)-2-[(3,4-dichlorobenzyl)amino]-5-(1H-pyrrolo[2,3-b]pyridin-3-ylmethylene)-3,5-dihydro-4H-imidazol-4-one dihydrochloride;

(5Z)-2-[(3-bromobenzyl)amino]-5-(1H-pyrrolo[2,3-b]pyridin-3-ylmethylene)-3,5-dihydro-4H-imidazol-4-one dihydrochloride;

(5Z)-2-[(3-methylbenzyl)amino]-5-(1H-pyrrolo[2,3-b]pyridin-3-ylmethylene)-3,5-dihydro-4H-imidazol-4-one dihydrochloride;

(5Z)-2-[(4-methylbenzyl)amino]-5-(1H-pyrrolo[2,3-b]pyridin-3-ylmethylene)-3,5-dihydro-4H-imidazol-4-one dihydrochloride;

(5Z)-5-(1H-pyrrolo[2,3-b]pyridin-3-ylmethylene)-2-{[4-(trifluoromethyl)benzyl]amino}-3,5-dihydro-4H-imidazol-4-one dihydrochloride;

(5Z)-2-[(4-methoxybenzyl)amino]-5-(1H-pyrrolo[2,3-b]pyridin-3-ylmethylene)-3,5-dihydro-4H-imidazol-4-one dihydrochloride;

(5Z)-2-[(3,4-dimethoxybenzyl)amino]-5-(1H-pyrrolo[2,3-b]pyridin-3-ylmethylene)-3,5-dihydro-4H-imidazol-4-one dihydrochloride;

(5Z)-5-(1H-pyrrolo[2,3-b]pyridin-3-ylmethylene)-2-{[(1R,2R,3R)-2,6,6-trimethylbicyclo[3.1.1]hept-3-yl]amino}-3,5-dihydro-4H-imidazol-4-one dihydrochloride;

(5Z)-2-[(3,4-difluorobenzyl)amino]-5-(1H-pyrrolo[2,3-b]pyridin-3-ylmethylene)-3,5-dihydro-4H-imidazol-4-one dihydrochloride;

(5Z)-2-(cycloheptylamino)-5-(1H-pyrrolo[2,3-b]pyridin-3-ylmethylene)-3,5-dihydro-4H-imidazol-4-one dihydrochloride;

(5Z)-2-[(2-methylcyclohexyl)amino]-5-(1H-pyrrolo[2,3-b]pyridin-3-ylmethylene)-3,5-dihydro-4H-imidazol-4-one dihydrochloride;

(5Z)-2-[(3-methylcyclohexyl)amino]-5-(1H-pyrrolo[2,3-b]pyridin-3-ylmethylene)-3,5-dihydro-4H-imidazol-4-one dihydrochloride;

(5Z)-2-[(2,2'-bithien-5-ylmethyl)amino]-5-(1H-pyrrolo[2,3-b]pyridin-3-ylmethylene)-3,5-dihydro-4H-imidazol-4-one dihydrochloride;

(5Z)-2-{[(3-methylthien-2-yl)methyl]amino}-5-(1H-pyrrolo[2,3-b]pyridin-3-ylmethylene)-3,5-dihydro-4H-imidazol-4-one dihydrochloride;

(5Z)-5-(1H-pyrrolo[2,3-b]pyridin-3-ylmethylene)-2-(1,2,3,4-tetrahydronaphthalen-1-ylamino)-3,5-dihydro-4H-imidazol-4-one dihydrochloride;

(5Z)-2-{[(5-pyridin-2-ylthien-2-yl)methyl]amino}-5-(1H-pyrrolo[2,3-b]pyridin-3-ylmethylene)-3,5-dihydro-4H-imidazol-4-one dihydrochloride;

(5Z)-2-[(4-tert-butylcyclohexyl)amino]-5-(1H-pyrrolo[2,3-b]pyridin-3-ylmethylene)-3,5-dihydro-4H-imidazol-4-one dihydrochloride;

(5Z)-5-(1H-pyrrolo[2,3-b]pyridin-3-ylmethylene)-2-{[(1R,2S,4R)-1,7,7-trimethylbicyclo[2.2.1]hept-2-yl]amino}-3,5-dihydro-4H-imidazol-4-one dihydrochloride;

2-(cyclopentylamino)-5-(1H-pyrrolo[2,3-b]pyridin-3-ylmethylene)-3,5-dihydro-4H-imidazol-4-one dihydrochloride;

(5Z)-2-[(4-methylcyclohexyl)amino]-5-(1H-pyrrolo[2,3-b]pyridin-3-ylmethylene)-3,5-dihydro-4H-imidazol-4-one dihydrochloride;

(5Z)-2-[(2,3-dimethylcyclohexyl)amino]-5-(1H-pyrrolo[2,3-b]pyridin-3-ylmethylene)-3,5-dihydro-4H-imidazol-4-one dihydrochloride;

(5Z)-2-[(1-phenylethyl)amino]-5-(1H-pyrrolo[2,3-b]pyridin-3-ylmethylene)-3,5-dihydro-4H-imidazol-4-one dihydrochloride;

(5Z)-2-{[1-(4-fluorophenyl)ethyl]amino}-5-(1H-pyrrolo[2,3-b]pyridin-3-ylmethylene)-3,5-dihydro-4H-imidazol-4-one dihydrochloride;

(5Z)-2-[(2,3-dihydro-1H-inden-1-ylmethyl)amino]-5-(1H-pyrrolo[2,3-b]pyridin-3-ylmethylene)-3,5-dihydro-4H-imidazol-4-one trifluoroacetate;

(5Z)-2-{[4-(4-methylpiperazin-1-yl)benzyl]amino}-5-(1H-pyrrolo[2,3-b]pyridin-3-ylmethylene)-3,5-dihydro-4H-imidazol-4-one dihydrochloride;

(5Z)-2-[(1-phenylpropyl)amino]-5-(1H-pyrrolo[2,3-b]pyridin-3-ylmethylene)-3,5-dihydro-4H-imidazol-4-one trifluoroacetate;

(5Z)-5-(1H-pyrrolo[2,3-b]pyridin-3-ylmethylene)-2-[(1S)-1,2,3,4-tetrahydronaphthalen-1-ylamino]-3,5-dihydro-4H-imidazol-4-one dihydrochloride;

(5Z)-2-[(4-bromobenzyl)amino]-5-(1H-pyrrolo[2,3-b]pyridin-3-ylmethylene)-3,5-dihydro-4H-imidazol-4-one dihydrochloride;

(5Z)-2-[(2,3-dihydro-1H-inden-2-ylmethyl)amino]-5-(1H-pyrrolo[2,3-b]pyridin-3-ylmethylene)-3,5-dihydro-4H-imidazol-4-one dihydrochloride;

(5Z)-2-[(1-benzothien-2-ylmethyl)amino]-5-(1H-pyrrolo[2,3-b]pyridin-3-ylmethylene)-3,5-dihydro-4H-imidazol-4-one dihydrochloride;

(5Z)-2-{[(1S,2R,5S)-2-isopropyl-5-methylcyclohexyl]amino}-5-(1H-pyrrolo[2,3-b]pyridin-3-ylmethylene)-3,5-dihydro-4H-imidazol-4-one trifluoroacetate;

(5Z)-2-(bicyclo[2.2.1]hept-2-ylamino)-5-(1H-pyrrolo[2,3-b]pyridin-3-ylmethylene)-3,5-dihydro-4H-imidazol-4-one trifluoroacetate;

(5Z)-2-{[3-fluoro-5-(trifluoromethyl)benzyl]amino}-5-(1H-pyrrolo[2,3-b]pyridin-3-ylmethylene)-3,5-dihydro-4H-imidazol-4-one trifluoroacetate;

(5Z)-2-[(1-ethylpropyl)amino]-5-(1H-pyrrolo[2,3-b]pyridin-3-ylmethylene)-3,5-dihydro-4H-imidazol-4-one dihydrochloride;

(5Z)-5-(1H-pyrrolo[2,3-b]pyridin-3-ylmethylene)-2-[(2,2,6,6-tetramethylpiperidin-4-yl)amino]-3,5-dihydro-4H-imidazol-4-one dihydrochloride;

(5Z)-2-(adamantanamino)-5-(1H-pyrrolo[2,3-b]pyridin-3-ylmethylene)-3,5-dihydro-4H-imidazol-4-one dihydrochloride;

(5Z)-2-(isopropylamino)-5-(1H-pyrrolo[2,3-b]pyridin-3-ylmethylene)-3,5-dihydro-4H-imidazol-4-one dihydrochloride;

(5Z)-2-{[3-(dimethylamino)-2,2-dimethylpropyl]amino}-5-(1H-pyrrolo[2,3-b]pyridin-3-ylmethylene)-3,5-dihydro-4H-imidazol-4-one dihydrochloride;

(5Z)-2-[(3R)-1-azabicyclo[2.2.2]oct-3-ylamino]-5-(1H-pyrrolo[2,3-b]pyridin-3-ylmethylene)-3,5-dihydro-4H-imidazol-4-one hydrochloride trifluoroacetate;

(5Z)-2-{[(1R, 5S)-8-methyl-8-azabicyclo[3.2.1]oct-3-yl]amino}-5-(1H-pyrrolo[2,3-b]pyridin-3-ylmethylene)-3,5-dihydro-4H-imidazol-4-one hydrochloride trifluoroacetate;

(5Z)-2-[(3S)-1-azabicyclo[2.2.2]oct-3-ylamino]-5-(1H-pyrrolo[2,3-b]pyridin-3-ylmethylene)-3,5-dihydro-4H-imidazol-4-one hydrochloride trifluoroacetate;

(5Z)-2-{[(1S)-1-phenyl-2-pyrrolidin-1-ylethyl]amino}-5-(1H-pyrrolo[2,3-b]pyridin-3-ylmethylene)-3,5-dihydro-4H-imidazol-4-one hydrochloride trifluoroacetate;

(5Z)-2-[(4-hydroxycyclohexyl)amino]-5-(1H-pyrrolo[2,3-b]pyridin-3-ylmethylene)-3,5-dihydro-4H-imidazol-4-one;

(5Z)-2-{[(2S)-2-hydroxycyclohexyl]amino}-5-(1H-pyrrolo[2,3-b]pyridin-3-ylmethylene)-3,5-dihydro-4H-imidazol-4-one;

(5Z)-2-{[(1S,2S,3R,4R)-3-(hydroxymethyl)bicyclo[2.2.1]hept-2-yl]amino}-5-(1H-pyrrolo[2,3-b]pyridin-3-ylmethylene)-3,5-dihydro-4H-imidazol-4-one dihydrochloride;

(5Z)-2-(adamantylmethylamino)-5-(1H-pyrrolo[2,3-b]pyridin-3-ylmethylene)-3,5-dihydro-4H-imidazol-4-one dihydrochloride;

(5Z)-2-[(1S,2R,4R)-bicyclo[2.2.1]hept-2-ylamino]-5-(1H-pyrrolo[2,3-b]pyridin-3-ylmethylene)-3,5-dihydro-4H-imidazol-4-one dihydrochloride;

(5Z)-2-{[(1R)-1-phenylethyl]amino}-5-(1H-pyrrolo[2,3-b]pyridin-3-ylmethylene)-3,5-dihydro-4H-imidazol-4-one dihydrochloride;

(5Z)-5-(1H-pyrrolo[2,3-b]pyridin-3-ylmethylene)-2-{[(1R,4R)-1,7,7-trimethylene[2.2.1]hept-2-yl]amino}-3,5-dihydro-4H-imidazol-4-one dihydrochloride;

(5Z)-2-{[(1R,2S,3R,4S)-3-(hydroxymethyl)bicyclo[2.2.1]hept-2-yl]amino}-5-(1H-pyrrolo[2,3-b]pyridin-3-ylmethylene)-3,5-dihydro-4H-imidazol-4-one dihydrochloride;

(5Z)-5-(1H-pyrrolo[2,3-b]pyridin-3-ylmethylene)-2-{[(1R,2R,3R,5S)-2,6,6-trimethylbicyclo[3.1.1]hept-3-yl]amino}-3,5-dihydro-4H-imidazol-4-one dihydrochloride;

(5Z)-2-{[(1S)-2-(4-methylpiperazin-1-yl)-1-phenylethyl]amino}-5-(1H-pyrrolo[2,3-b]pyridin-3-ylmethylene)-3,5-dihydro-4H-imidazol-4-one dihydrochloride;

(5Z)-2-{[(1S)-1-phenyl-2-piperidin-1-ylethyl]amino}-5-(1H-pyrrolo[2,3-b]pyridin-3-ylmethylene)-3,5-dihydro-4H-imidazol-4-one dihydrochloride;

(5Z)-2-{[(1S)-2-morpholin-4-yl-1-phenylethyl]amino}-5-(1H-pyrrolo[2,3-b]pyridin-3-ylmethylene)-3,5-dihydro-4H-imidazol-4-one dihydrochloride;

(5Z)-2-{[1-(3-fluorophenyl)ethyl]amino}-5-(1H-pyrrolo[2,3-b]pyridin-3-ylmethylene)-3,5-dihydro-4H-imidazol-4-one dihydrochloride;

(5Z)-2-[(1,2,2,6,6-pentamethylpiperidin-4-yl)amino]-5-(1H-pyrrolo[2,3-b]pyridin-3-ylmethylene)-3,5-dihydro-4H-imidazol-4-one dihydrochloride;

(5Z)-2-[(2-hydroxy-1-phenylethyl)amino]-5-(1H-pyrrolo[2,3-b]pyridin-3-ylmethylene)-3,5-dihydro-4H-imidazol-4-one dihydrochloride;

(5Z)-2-[(3-hydroxy-1-phenylpropyl)amino]-5-(1H-pyrrolo[2,3-b]pyridin-3-ylmethlene)-3,5-dihydro-4H-imidazol-4-one dihydrochloride;

(5Z)-2-{[(1R)-1-phenyl-2-pyrrolidin-1-ylethyl]amino}-5-(1H-pyrrolo[2,3-b]pyridin-3-ylmethylene)-3,5-dihydro-4H-imidazol-4-one;

(5Z)-2-{[(1R)-1-phenylethyl]amino}-5-(1H-pyrrolo[2,3-b]pyridin-3-ylmethylene)-3,5-dihydro-4H-imidazol-4-one dihydrochloride;

(5Z)-2-{[(1S)-1-phenylethyl]amino}-5-(1H-pyrrolo[2,3-b]pyridin-3-ylmethylene)-3,5-dihydro-4H-imidazol-4-one dihydrochloride;

(5Z)-2-(benzylthio)-5-(1H-pyrrolo[2,3-b]pyridin-3-ylmethylene)-3,5-dihydro-4H-imidazol-4-one;

(5Z)-N-(3-{[2-(benzylamino)-5-oxo-1,5-dihydro-4H-imidazol-4-ylidene]methyl}-1H-pyrrolo[2,3-b]pyridin-5-yl)acetamide hydrochloride;

(5E)-N-(3-{[2-(benzylamino)-5-oxo-1,5-dihydro-4H-imidazol-4-ylidene]methyl}-1H-pyrrolo[2,3-b]pyridin-5-yl)acetamide hydrochloride;

(5Z)-2-(benzylamino)-5-[(5-nitro-1H-pyrrolo[2,3-b]pyridin-3-yl)methylene]-3,5-dihydro-4H-imidazol-4-one;

(5E)-2-(benzylamino)-5-[(5-nitro-1H-pyrrolo[2,3-b]pyridin-3-yl)methylene]-3,5-dihydro-4H-imidazol-4-one;

(5Z)-5-[(5-amino-1H-pyrrolo[2,3-b]pyridin-3-yl)methylene]-2-(benzylamino)-3,5-dihydro-4H-imidazol-4-one;

(5E)-5-[(5-amino-1H-pyrrolo[2,3-b]pyridin-3-yl)methylene]-2-(benzylamino)-3,5-dihydro-4H-imidazol-4-one;

(5Z)-2-(benzylamino)-5-[1-(1H-pyrrolo[2,3-b]pyridin-3-yl)ethylidene]-3,5-dihydro-4H-imidazol-4-one hydrochloride;

N-[3-(4-methylpiperazin-1-yl)benzoyl]glycine;

(5Z)-2-(4-chlorophenyl)-5-(1H-pyrrolo[2,3-b]pyridin-3-ylmethylene)-3,5-dihydro-4H-imidazol-4-one;

(5Z)-2-[3-(hydroxymethyl)phenyl]-5-(1H-pyrrolo[2,3-b]pyridin-3-ylmethylene)-3,5-dihydro-4H-imidazol-4-one;

(5Z)-2-pyridin-4-yl-5-(1H-pyrrolo[2,3-b]pyridin-3-ylmethylene)-3,5-dihydro-4H-imidazol-4-one;

(5Z)-2-pyridin-2-yl-5-(1H-pyrrolo[2,3-b]pyridin-3-ylmethylene)-3,5-dihydro-4H-imidazol-4-one;

(5Z)-2-{3-[(1-methylpiperidin-4-yl)oxy]phenyl}-5-(1H-pyrrolo[2,3-b]pyridin-3-ylmethylene)-3,5-dihydro-4H-imidazol-4-one;

(5Z)-2-(4-morpholin-4-ylphenyl)-5-(1H-pyrrolo[2,3-b]pyridin-3-ylmethylene)-3,5-dihydro-4H-imidazol-4-one;

(5Z)-2-(3-morpholin-4-ylphenyl)-5-(1H-pyrrolo[2,3-b]pyridin-3-ylmethylene)-3,5-dihydro-4H-imidazol-4-one;

(5Z)-2-(propylamino)-5-(1H-pyrrolo[2,3-b]pyridin-3-ylmethylene)-3,5-dihydro-4H-imidazol-4-one;

(5Z)-2-[(2-pyrrolidin-1-ylethyl)amino]-5-(1H-pyrrolo[2,3-b]pyridin-3-ylmethylene)-3,5-dihydro-4H-imidazol-4-one;

(5Z)-2-{[2-(dimethylamino)ethyl]amino}-5-(1H-pyrrolo[2,3-b]pyridin-3-ylmethylene)-3,5-dihydro-4H-imidazol-4-one;

(5Z)-2-[4-(hydroxymethyl)piperidin-1-yl]-5-(1H-pyrrolo[2,3-b]pyridin-3-ylmethylene)-3,5-dihydro-4H-imidazol-4-one;

(5Z)-1-[5-oxo-4-(1H-pyrrolo[2,3-b]pyridin-3-ylmethylene)-4,5-dihydro-1H-imidazol-2-yl]piperidine-4-carboxamide;

(5Z)-N,N-diethyl-1-[5-oxo-4-(1H-pyrrolo[2,3-b]pyridin-3-ylmethylene)-4,5-dihydro-1H-imidazol-2-yl]piperidine-3-carboxamide;

(5Z)-2-(4-hydroxypiperidin-1-yl)-5-(1H-pyrrolo[2,3-b]pyridin-3-ylmethylene)-3,5-dihydro-4H-imidazol-4-one;

(5Z)-2-(3-hydroxypiperidin-1-yl)-5-(1H-pyrrolo[2,3-b]pyridin-3-ylmethylene)-3,5-dihydro-4H-imidazol-4-one;

(5Z)-2-azetidin-1-yl-5-(1H-pyrrolo[2,3-b]pyridin-3-ylmethylene)-3,5-dihydro-4-one (5Z)-2-(2,5-dihydro-1H-pyrrol-1-yl)-5-(1H-pyrrolo[2,3-b]pyridin-3-ylmethylene)-3,5-dihydro-4H-imidazol-4-one;

(5Z)-2-(3-hydroxypyrrolidin-1-yl)-5-(1H-pyrrolo[2,3-b]pyridin-3-ylmethylene)-3,5-dihydro-4H-imidazol-4-one;

(5Z)-2-pyrazolidin-1-yl-5-(1H-pyrrolo[2,3-b]pyridin-3-yl methylene)-3,5-dihydro-4H-imidazol-4-one;

(5Z)-1-[5-oxo-4-(1H-pyrrolo[2,3-b]pyridin-3-ylmethylene)-4,5-dihydro-1H-imidazol-2-yl]prolinamide;

(5Z)-2-(4-allylpiperazin-1-yl)-5-(1H-pyrrolo[2,3-b]pyridin-3-ylmethylene)-3,5-dihydro-4H-imidazol-4-one;

(5Z)-2-(4-ethylpiperazin-1-yl)-5-(1H-pyrrolo[2,3-b]pyridin-3-ylmethylene)-3,5-dihydro-4H-imidazol-4-one;

(5Z)-2-[4-(2-oxo-2-pyrrolidin-1-ylethyl)piperazin-1-yl]-5-(1H-pyrrolo[2,3-b]pyridin-3-ylmethylene)-3,5-dihydro-4H-imidazol-4-one;

(5Z)-N-isopropyl-2-{4-[5-oxo-4-(1H-pyrrolo[2,3-b]pyridin-3-ylmethylene)-4,5-dihydro-1H-imidazol-2-yl]piperazin-1-yl}acetamide;

(5Z)-2-[4-(4-hydroxyphenyl)piperazin-1-yl]-5-(1H-pyrrolo[2,3-b]pyridin-3-ylmethlene)-3,5-dihydro-4H-imidazol-4-one;

(5Z)-5-(1H-pyrrolo[2,3-b]pyridin-3-ylmethylene)-2-[4-(tetrahydrofuran-2-ylcarbonyl)piperazin-1-yl]-3,5-dihydro-4H-imidazol-4-one;

(5Z)-5-(1H-pyrrolo[2,3-b]pyridin-3-ylmethylene)-2-{[(1S,2R,4S)-1,3,3-trimethylbicyclo[2.2.1]hept-2-yl]amino}-3,5-dihydro-4H-imidazol-4-one;

(5Z)-5-(1H-pyrrolo[2,3-b]pyridin-3-ylmethylene)-2-{[(1S,2R,4R)-1,7,7-trimethylbicyclo[2.2.1]hept-2-yl]amino}-3,5-dihydro-4H-imidazol-4-one;

(5Z)-2-[(1-phenylcyclopropyl)amino]-5-(1H-pyrrolo[2,3-b]pyridin-3-ylmethylene)-3,5-dihydro-4H-imidazol-4-one;

(5Z)-2-[(2-morpholin-4-ylethyl)amino]-5-(1H-pyrrolo[2,3-b]pyridin-3-ylmethylene)-3,5-dihydro-4H-imidazol-4-one;

(5Z)-2-[(2-pyrrolidin-1-ylethyl)amino]-5-(1H-pyrrolo[2,3-b]pyridin-3-ylmethylene)-3,5-dihydro-4H-imidazol-4-one;

(5Z)-1-methyl-N-{3-[(5-oxo-2-phenyl-1,5-dihydro-4H-imidazol-4-ylidene)methyl]-1H-pyrrolo[2,3-b]pyridin-5-yl}piperidine-4-carboxamide;

(5Z)-$N_3$-,$N_3$-dimethyl-$N_1$-{3-[(5-oxo-2-phenyl-1,5-dihydro-4H-imidazol-4-ylidene)methyl]-1H-pyrrolo[2.3-b]pyridin-5-yl}-beta-alaninamide;

(5Z)-3-(4-methylpiperazin-1-yl)-N-{3-[(5-oxo-2-phenyl-1,5-dihydro-4H-imidazol-4-ylidene)methyl]-1H-pyrrolo[2,3-b]pyridin-5-yl}benzamide;

(5Z)-4-(4-methylpiperazin-1-yl)-N-{3-[(5-oxo-2-phenyl-1,5-dihydro-4H-imidazol-4-ylidene)methyl]-1H-pyrrolo[2,3-b]pyridin-5-yl}benzamide;

(5Z)-N-(3-{[2-(benzylamino)-5-oxo-1,5-dihydro-4H-imidazol-4-ylidene]methyl}-1H -pyrrolo[2,3-b]pyridin-5-yl)-1-methylpiperidene-4-carboxamide;

(5Z)-1-methyl-N-[3-({5-oxo-2-[(1-phenylethyl)amino]-1,5-dihydro-4H-imidazol-4-ylidene}methyl)-1H-pyrrolo[2,3-b]pyridin-5-yl]piperidine-4-carboxamide;

(5Z)-N-(3-{[2-(cyclohexylamino)-5-oxo-1,5-dihydro-4H-imidazol-4-ylidene]methyl}-1H-pyrrolo[2,3-b]pyridin-5-yl)-1-methylpiperidine-4-carboxamide;

(5Z)-N-(3-{[2-(bicyclo[2.2.1]hept-2-ylamino)-5-oxo-1,5-dihydro-4H-imidazol-4-ylidene]methyl}-1H-pyrrolo[2,3-b]pyridin-5-yl)-1-methylpiperidine-4-carboxamide;

(5Z)-N-(3-{[2-(1-adamantylamino)-5-oxo-1,5-dihydro-4H-imidazol-4-ylidene]methyl}-1H-pyrrolo[2,3-b]pyridin-5-yl)-1-methylpiperidine-4-carboxamide;

(5Z)-1-methyl-N-[3-({5-oxo-2-[(1,7,7-trimethylbicyclo[2.2.1]hept-2-yl)amino]-1,5-dihydro-4H-imidazol-4-ylidene}methyl)-1H-pyrrolo[2,3-b]pyridin-5-yl]piperidine-4-carboxamide;

(5Z)-N-(3-{[2-(1-azabicyclo[2.2.2]oct-3-ylamino)-5-oxo-1,5-dihydro-4H-imidazol-4-ylidene]methyl}-1H-pyrrolo[2,3-b]pyridin-5-yl)-1-methylpiperidine-4-carboxamide;

(5Z)-1-methyl-N-[3-({5-oxo-2-[(1-phenyl-2-pyrrolidin-1-ylethyl)amino]-1,5-dihydro-4H-imidazol-4-ylidene}methyl)-1H-pyrrolo[2,3-b]pyridin-5-yl]piperidine-4-carboxamide;

(5Z)-$N_1$-(3-{[2-benzylamino-5-oxo-1,5-dihydro-4H-imidazol-4-ylidene]methyl}-1H-pyrrolo[2,3-b]pyridin-5-yl)-$N_3$,$N_3$-dimethyl-beta-alaninamide;

(5Z)-$N_3$,$N_3$-dimethyl-$N_1$-[3-({5-oxo-2-[(1-phenylethyl)amino]-1,5-dihydro-4-ylidene 3 methyl)-1H-pyrrolo[2,3-b]pyridin-5-yl}-beta-alaninamide;

(5Z)-$N_1$-{[2-(cyclohexylamino)-5-oxo-1,5-dihydro-4H-imidazol-4-ylidene]methyl3-1H-pyrrolo[2,3-b]pyridin-5-yl)-$N_3$, $N_3$-dimethyl-beta-alaninamide;

(5Z)-$N_1$-(3-{[2-(bicyclo[2.2.1]hept-2-ylamino)-5-oxo-1,5-dihydro-4H-imidazol-4-ylidene]methyl}-1H-pyrrolo[2,3-b]pyridin-5-yl)-$N_3$,$N_3$-dimethyl-beta-alaninamide;

(5Z)-N-(3-{[2-(1-azabicyclo[2.2.2]oct-3-ylamino)-5-oxo-1,5-dihydro-4H-imidazol-4-ylidene]methyl}-1H-pyrrolo[2,3-b]pyridin-5-yl)butanamide;

(5Z)-N-(3-{[2-(benzylamino)-5-oxo-1,5-dihydro-4H-imidazol-4-ylidene]methyl}-1H-pyrrolo[2,3-b]pyridin-5-yl)-3-(4-methylpiperazin-1-yl)benzamide;

(5Z)-3-(4-methylpiperazin-1-yl)-N-[3-({5-oxo-2-[(1-phenylethyl)amino]-1,5-dihydro-4H-imidazol-4-ylidene}methyl)-1H-pyrrolo[2,3-b]pyridin-5-yl]benzamide;

(5Z)-N-(3-{[2-(cyclohexylamino)-5-oxo-1,5-dihydro-4H-imidazol-4-ylidene]methyl}-1H-pyrrolo[2,3-b]pyridin-5-yl)-3-(4-methylpiperazin-1-yl)benzamide;

(5Z)-N-(3-{[2-(bicyclo[2.2.1]hept-2-ylamino)-5-oxo-1,5-dihydro-4H-imidazol-4-ylidene]methyl}-1H-pyrrolo[2,3-b]pyridin-5-yl)-3-(4-methylpiperazin-1-yl)benzamide;

(5Z)-N-(3-{[2-(1-azabicyclo[2.2.2]oct-3-ylamino)-5-oxo-1,5-dihydro-4H-imidazol-4-ylidene]methyl}-1H-pyrrolo[2,3-b]pyridin-5-yl)-2-methylpropanamide;

(5Z)-N-(3-{[2-(benzylamino)-5-oxo-1,5-dihydro-4H-imidazol-4-ylidene]methyl}-1H-pyrrolo[2,3-b]pyridin-5-yl)-4-(4-methylpiperazin-1-yl)benzamide;

(5Z)-4-(4-methylpiperazin-1-yl)-N-[3-({5-oxo-2-[(1-phenylethyl)amino]-1,5-dihydro-4H-imidazol-4-ylidene}methyl)-1H-pyrrolo[2,3-b]pyridin-5-yl]benzamide;

(5Z)-N-(3-{[2-(cyclohexylamino)-5-oxo-1,5-dihydro-4H-imidazol-4-ylidene]methyl}-1H-pyrrolo[2,3-b]pyridin-5-yl)-4-(4-methylpiperazin-1-yl)benzamide;

(5Z)-N-(3-{[2-(bicyclo[2.2.1]hept-2-ylamino)-5-oxo-1,5-dihydro-4H-imidazol-4-ylidene]methyl}-1H-pyrrolo[2,3-b]pyridin-5-yl)-4-(4-methylpiperazin-1-yl)benzamide; or (5Z)-N-(3-{[2-(1-azabicyclo[2.2.2]oct-3-ylamino)-5-oxo-1,5-dihydro-4H-imidazol-4-ylidene]methyl}-1H-pyrrolo[2,3-b]pyridin-5-yl)-3-methylbutanamide.

27. A composition comprising compound according to claim 26 and a pharmaceutical carrier therefor.

* * * * *